United States Patent
Lin et al.

(10) Patent No.: US 9,958,443 B2
(45) Date of Patent: May 1, 2018

(54) SIGNAL ENHANCEMENT MECHANISM FOR DUAL-GATE ION SENSITIVE FIELD EFFECT TRANSISTOR IN ON-CHIP DISEASE DIAGNOSTIC PLATFORM

(71) Applicant: Taiwan Semiconductor Manufacturing Company, Ltd., Hsinchu (TW)

(72) Inventors: Ching-Hui Lin, Tiachung (TW); Chun-Ren Cheng, Hsin-Chu (TW); Shih-Fen Huang, Jhubei (TW); Yi-Hsien Chang, Changhua County (TW)

(73) Assignee: TAIWAN SEMICONDUCTOR MANUFACTURING COMPANY, LTD., Hsin-Chu (TW)

( * ) Notice: Subject to any disclaimer, the term of this patent is extended or adjusted under 35 U.S.C. 154(b) by 0 days. days.

(21) Appl. No.: 15/581,673

(22) Filed: Apr. 28, 2017

(65) Prior Publication Data
US 2017/0227533 A1  Aug. 10, 2017

Related U.S. Application Data

(63) Continuation-in-part of application No. 15/356,503, filed on Nov. 18, 2016, which is a
(Continued)

(51) Int. Cl.
*H01L 51/05* (2006.01)
*G01N 27/414* (2006.01)
(Continued)

(52) U.S. Cl.
CPC .......... *G01N 33/5438* (2013.01); *C12Q 1/006* (2013.01); *G01N 27/414* (2013.01);
(Continued)

(58) Field of Classification Search
CPC ........... H01L 29/66484; H01L 29/7831; H01L 29/7832; H01L 51/0093; G01N 27/414;
(Continued)

(56) References Cited

U.S. PATENT DOCUMENTS

| | | | | |
|---|---|---|---|---|
| 7,695,609 B2* | 4/2010 | Soundarrajan | ......... | B82Y 10/00 204/403.01 |
| 8,519,490 B2* | 8/2013 | Bikumandla | ........... | H01L 27/00 204/403.01 |

(Continued)

OTHER PUBLICATIONS

Michael J. Schoning and Arshak Poghossian, "Recent Advances in Biologically Sensitive Field Effect Transistors (BioFETs)", Aug. 16, 2002, 15 pages, a University of Applied Sciences Aachen, Ginsterweg 1, D-52428 Jülich, Germany b Institute of Thin Films and Interfaces, Research Centre Juelich GmbH, D-52425 Jülich, Germany.

(Continued)

*Primary Examiner* — Marcos D Pizarro
*Assistant Examiner* — Christopher M Roland
(74) *Attorney, Agent, or Firm* — Haynes and Boone, LLP

(57) ABSTRACT

Dual-gate ion-sensitive field effect transistors (ISFETs) for disease diagnostics are disclosed herein. An exemplary dual-gate ISFET includes a gate structure and a fluidic gate structure disposed over opposite surfaces of a device substrate. The gate structure is disposed over a channel region defined between a source region and a drain region in the device substrate. The fluidic gate structure includes a sensing well that is disposed over the channel region. The sensing well includes a sensing layer and an electrolyte solution. The electrolyte solution includes a constituent that can react with a product of an enzymatic reaction that occurs when an enzyme-modified detection mechanism detects an analyte. The sensing layer can react with a first ion generated from the enzymatic reaction and a second ion generated (Continued)

from a reaction between the product of the enzymatic reaction and the constituent, such that the dual-gate ISFET generates an enhanced electrical signal.

20 Claims, 41 Drawing Sheets

Related U.S. Application Data continuation-in-part of application No. 13/831,106, filed on Mar. 14, 2013, now Pat. No. 9,689,835, which is a continuation-in-part of application No. 13/480,161, filed on May 24, 2012, now Pat. No. 9,459,234.

(60) Provisional application No. 61/553,606, filed on Oct. 31, 2011.

(51) Int. Cl.
　　*G01N 33/543* (2006.01)
　　*H01L 29/78* (2006.01)
　　*C12Q 1/00* (2006.01)
　　*H01L 51/00* (2006.01)
　　*H01L 29/66* (2006.01)

(52) U.S. Cl.
　　CPC ..... *G01N 27/4145* (2013.01); *G01N 27/4148* (2013.01); *H01L 29/66484* (2013.01); *H01L 29/7831* (2013.01); *H01L 29/7832* (2013.01); *H01L 51/0093* (2013.01); *H01L 51/0512* (2013.01)

(58) Field of Classification Search
　　CPC . G01N 27/4145; G01N 27/4148; C12Q 1/006
　　See application file for complete search history.

(56) References Cited

U.S. PATENT DOCUMENTS

| | | | |
|---|---|---|---|
| 8,878,258 B2 * | 11/2014 | Monfray | G01N 33/54373 257/253 |
| 2002/0006632 A1 | 1/2002 | Ponnampalam et al. | |
| 2004/0238379 A1 * | 12/2004 | Lindsay | G01N 27/4145 205/792 |
| 2006/0102935 A1 * | 5/2006 | Yitzchaik | C07K 17/14 257/253 |
| 2006/0246478 A1 * | 11/2006 | Yoo | G01N 33/54306 435/6.11 |
| 2007/0295988 A1 * | 12/2007 | Yamamoto | G01N 27/4145 257/147 |
| 2009/0008629 A1 * | 1/2009 | Matsumoto | B82Y 10/00 257/24 |
| 2010/0055699 A1 * | 3/2010 | Kahya | G01N 27/4145 435/6.19 |
| 2011/0316565 A1 * | 12/2011 | Guo | G01N 27/4145 257/24 |
| 2012/0021918 A1 * | 1/2012 | Bashir | G01N 27/4148 506/2 |
| 2013/0105868 A1 | 5/2013 | Kalnitsky et al. | |
| 2013/0200438 A1 | 8/2013 | Liu et al. | |
| 2013/0291627 A1 | 11/2013 | Hu et al. | |
| 2014/0151755 A1 * | 6/2014 | Liu | H01L 29/66477 257/252 |
| 2014/0264467 A1 * | 9/2014 | Cheng | G01N 27/4145 257/253 |

OTHER PUBLICATIONS

Jeho Park, et al. "Applications of Field-Effect Transistor (FET)-Type Biosensors", Applied Science and Convergence Technology vol. 23 No. 2, Mar. 2014, pp. 61-71.

Y.-J Huang, et al. "High Performance Dual-Gate ISFET with Non-ideal Effect Reduction Schemes in a SOI-CMOS Bioelectrical SoC", 2015 IEEE International Electron Devices Meeting (IEDM), Dec. 2015, Taiwan Semiconductor Manufacturing Company (TSMC), Hsinchu, Taiwan, pp. 29-2.1-29.2.4 (4 pages).

* cited by examiner

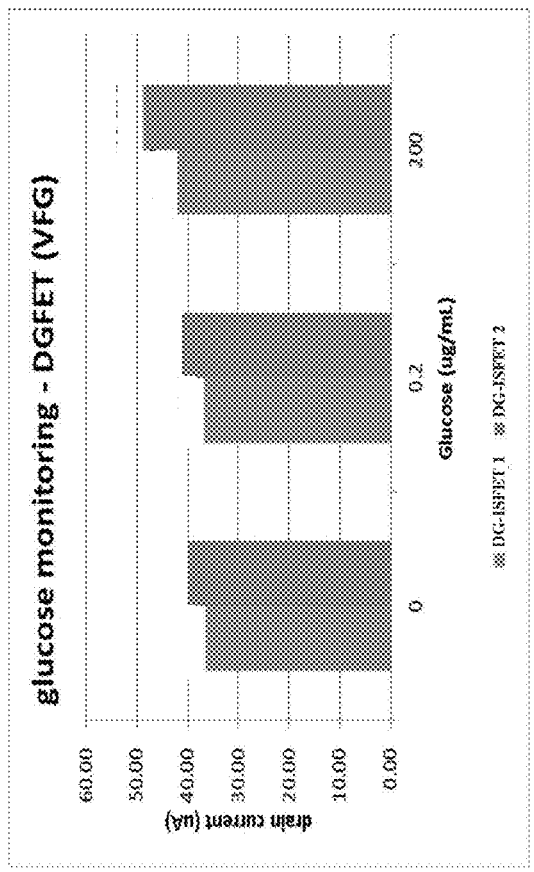
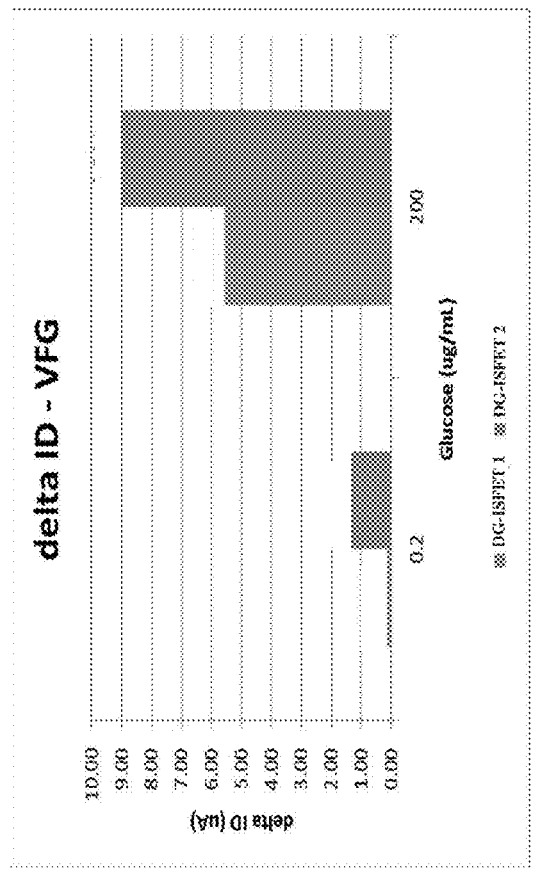
FIG. 39A
FIG. 39B

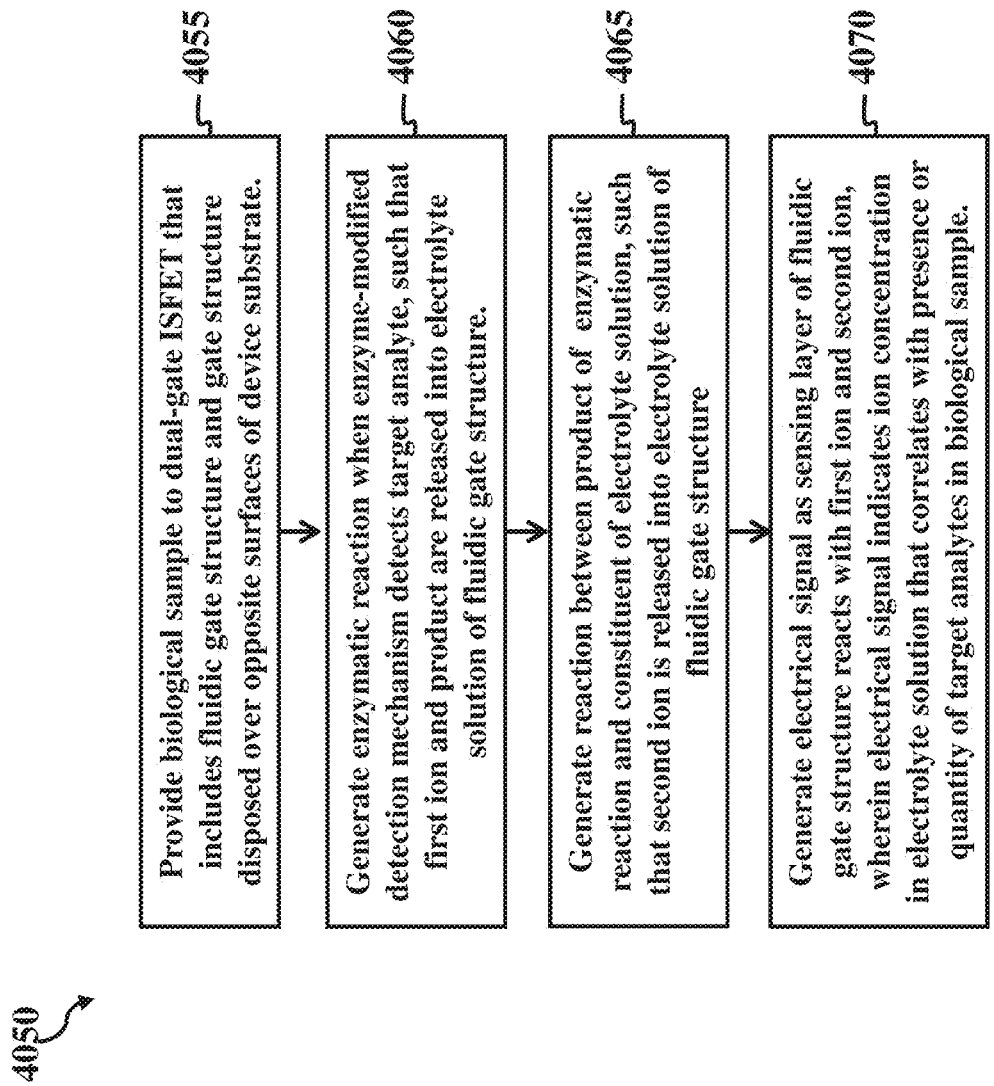

SIGNAL ENHANCEMENT MECHANISM FOR DUAL-GATE ION SENSITIVE FIELD EFFECT TRANSISTOR IN ON-CHIP DISEASE DIAGNOSTIC PLATFORM

PRIORITY DATA

This application is a continuation-in-part application of U.S. patent application Ser. No. 15/356,503, filed Nov. 18, 2016, which is a continuation-in-part application of U.S. patent application Ser. No. 13/831,106, filed Mar. 14, 2013, which is a continuation-in-part application of U.S. patent application Ser. No. 13/480,161, filed May 24, 2012, which claims priority to U.S. Provisional Patent Application Ser. No. 61/553,606, filed Oct. 31, 2011, the entire disclosures of which are incorporated herein by reference.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

BioFETs (biologically sensitive field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, integration of the electrical signals and biological applications, and/or other challenges arising from implementing a large scale integration (LSI) process.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 38A and FIG. 38B, FIG. 39A and FIG. 39B, and FIG. 40A and FIG. 40B compare various detection capabilities of dual-gate ISFETs, such as the dual-gate ISFET depicted in FIG. 37 and the dual-gate ISFET depicted in FIG. 31, according to various aspects of the present disclosure.

FIG. 43 is a flow chart of a method for analyzing a biological sample, which can be implemented by the dual-gate ISFET depicted in FIG. 37 or the dual-gate ISFET depicted in FIG. 41, according to various aspects of the present disclosure.

DETAILED DESCRIPTION

Figure 1:
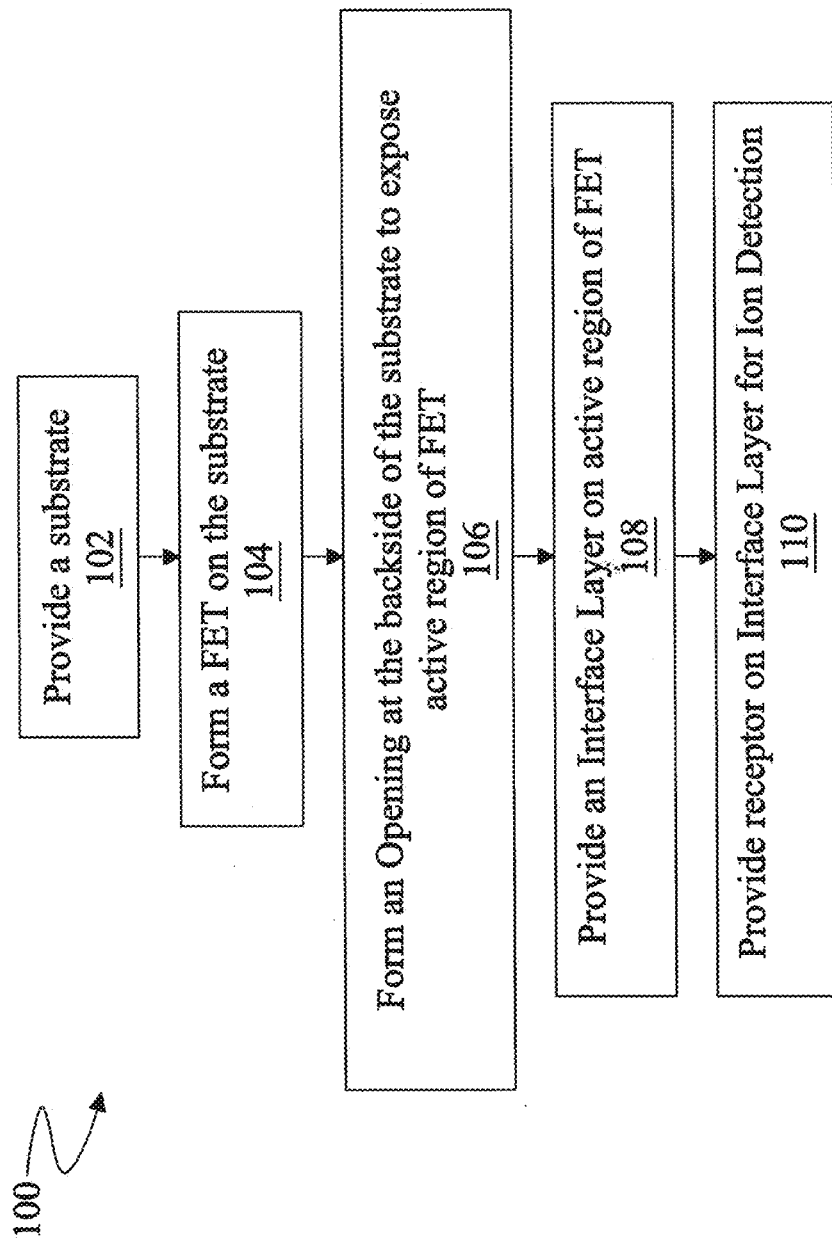
FIG. 1 is a flow chart of an embodiment of a method of fabricating a BioFET device according to one or more aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a BioFET, the gate of a MOSFET (metal-oxide-semiconductor field-effect transistor), which controls the conductance of the semiconductor between its source and drain contacts, is replaced by a bio- or biochemical-compatible layer or a biofunctionalized layer of immobilized probe molecules that act as surface receptors. Essentially, a BioFET is a field-effect biosensor with a semiconductor transducer. A decided advantage of BioFETs is the prospect of label-free operation. Specifically, BioFETs enable the avoidance of costly and time-consuming labeling operations such as the labeling of an analyte with, for instance, fluorescent or radioactive probes.

A typical detection mechanism for BioFETs is the conductance modulation of the transducer due to the binding of a target biomolecule or bio-entity to the gate or a receptor molecule immobilized on the gate of the BioFET. When the target biomolecule or bio-entity is bonded to the gate or the immobilized receptor, the drain current of the BioFET is varied by the gate potential. This change in the drain current can be measured and the bonding of the receptor and the target biomolecule or bio-entity can be identified. A great variety of biomolecules and bio-entities may be used to functionalize the gate of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the gate of the BioFET may be functionalized with immobilized complementary ssDNA strands. Also, to detect various proteins such as tumor markers, the gate of the BioFET may be functionalized with monoclonal antibodies.

One example of a typical biosensor is an ion-sensitive field effect transistor (ISFET) device. While suitable for some purposes, the ISFET has disadvantages. Its construction requires removal of the conductive gate material from the transistor and thus, exposure of the gate dielectric to the surrounding environment where potential-modulating surface reactions may occur. The ISFET device is also challenging to construct due to the multiple levels of metal interconnect layers.

Another device structure that may be formed includes connecting a gate structure with the surrounding environment though a stack of metal interconnect lines and vias (or multi-layer interconnect, MLI). In such an embodiment, the potential-modulating reaction takes place at an outer surface of the final (top) metal layer or a dielectric surface formed on top of the MLI. This embodiment may be disadvantageous however, in that the sensitivity of the device may be decreased due to the presence of parasitic capacitances associated with the MLI.

Figure 5:
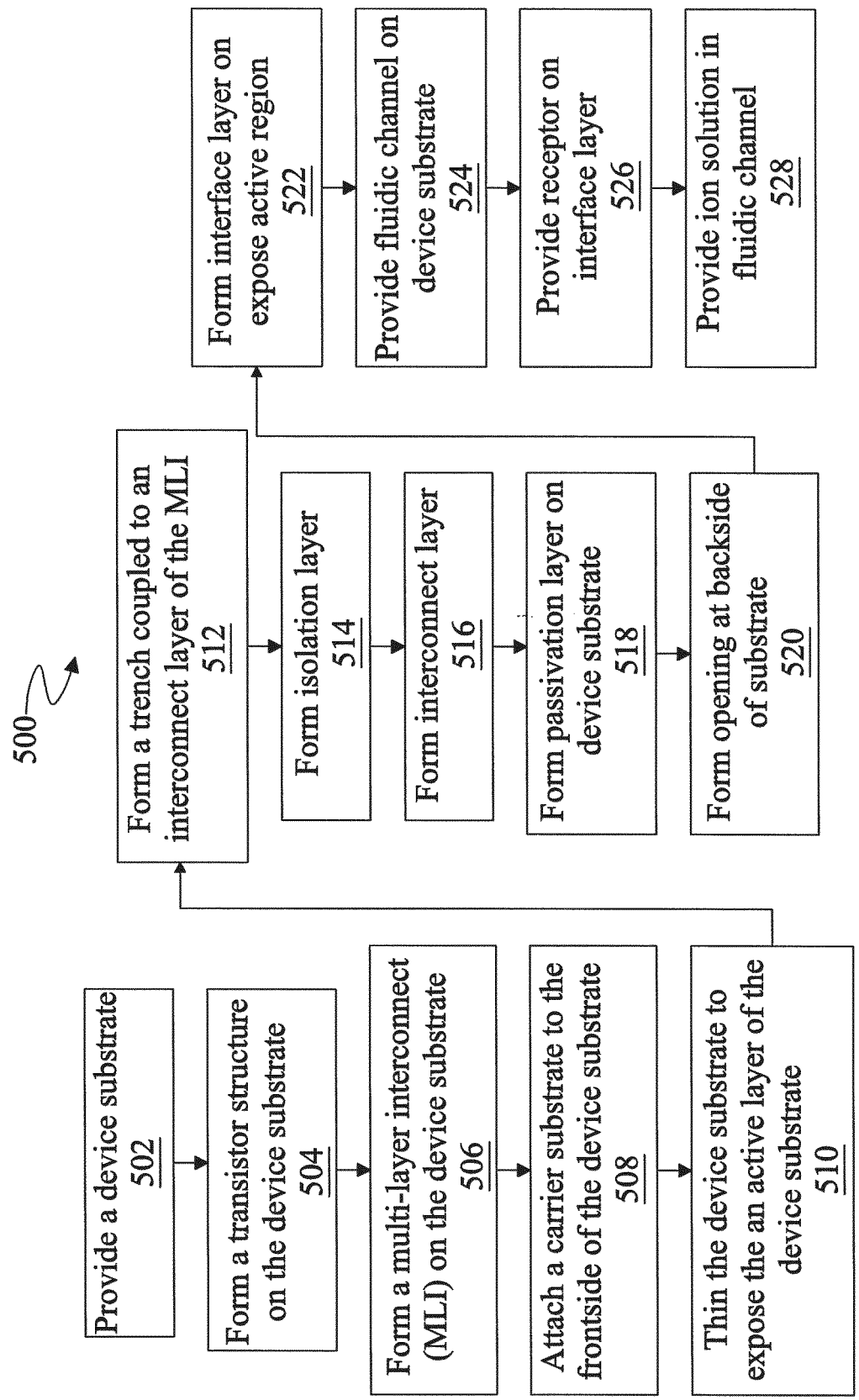
FIG. 5 is a flow chart of a method of fabricating a BioFET device using complementary metal oxide semiconductor (CMOS) compatible process(es).
Figure 18:
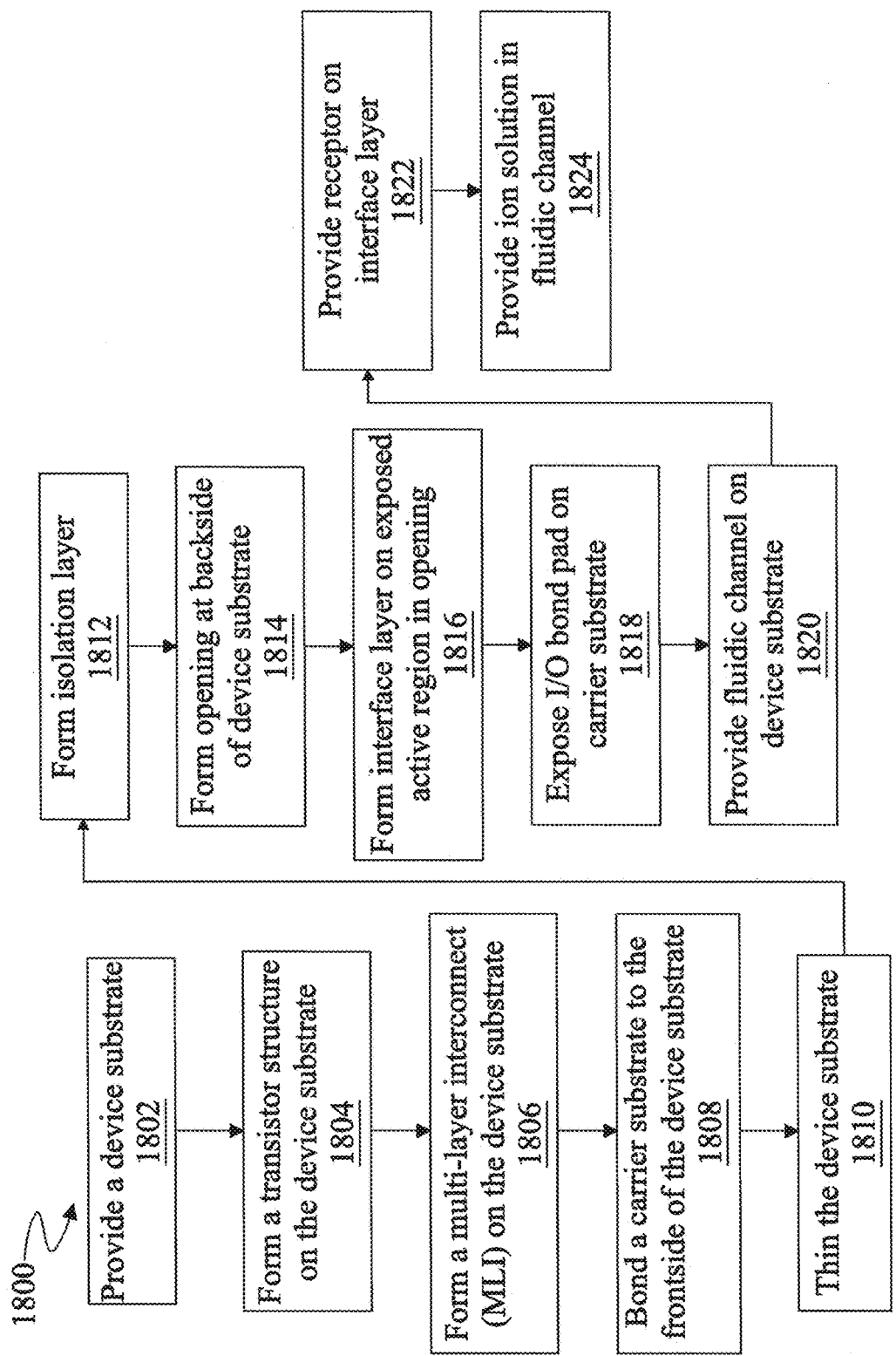
FIG. 18 is a flow chart of another method of fabricating a BioFET device using complementary metal oxide semiconductor (CMOS) compatible process(es).

Illustrated in FIG. 1 is an embodiment of a method 100 of fabricating a bio-organic field effect transistor (BioFET). The method 100 may include forming a BioFET using one or more process steps compatible with or typical to a complementary metal-oxide-semiconductor (CMOS) process. It is understood that additional steps can be provided before, during, and after the method 100, and some of the steps described below can be replaced or eliminated, for additional embodiments of the method. Further, it is understood that the method 100 includes steps having features of a typical CMOS technology process flow and thus, are only described briefly herein. It is also noted that FIGS. 5 and 18 provide further embodiments of the method 100, which may provide additional details applicable to the method 100.

The method 100 begins at block 102 where a substrate is provided. The substrate may be a semiconductor substrate (e.g., wafer). The semiconductor substrate may be a silicon substrate. Alternatively, the substrate may comprise another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the substrate is a semiconductor on insulator (SOI) substrate. The SOI substrate may include a buried oxide (BOX) layer formed by a process such as separation by implanted oxygen (SIMOX), and/or other suitable processes. The substrate may include doped regions, such as p-wells and n-wells.

The method 100 then proceeds to block 104 where a field effect transistor (FET) is formed on the substrate. The FET may include a gate structure, a source region, a drain region, and a channel region interposing the source and drain regions. The source, drain, and/or channel region may be formed on an active region of the semiconductor substrate. The FET may be an n-type FET (nFET) or a p-type FET (pFET). For example, the source/drain regions may comprise n-type dopants or p-type dopants depending on the FET configuration. The gate structure may include a gate dielectric layer, a gate electrode layer, and/or other suitable layers. In an embodiment, the gate electrode is polysilicon. Other exemplary gate electrodes include metal gate electrodes including material such as, Cu, W, Ti, Ta, Cr, Pt, Ag, Au; suitable metallic compounds like TiN, TaN, NiSi, CoSi; combinations thereof; and/or other suitable conductive materials. In an embodiment, the gate dielectric is silicon oxide. Other exemplary gate dielectrics include silicon nitride, silicon oxynitride, a dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($HfO_2$—$Al_2O_3$) alloy, or combinations thereof. The FET may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer deposition (ALD), spin on coating; etching including wet etching, dry etching, and plasma etching; and/or other suitable CMOS processes.

The method 100 then proceeds to block 106 where an opening is formed at the backside of the substrate. The opening may include a trench formed in one or more layers disposed on the backside of the substrate that includes the FET device. The opening may expose a region underlying the gate and body structure (e.g., adjacent the channel of the FET). In an embodiment, the opening exposes an active region (e.g., silicon active region) underlying the gate and active/channel region of the FET device. The opening may be formed using suitable photolithography processes to provide a pattern on the substrate and etching process to remove materials form the backside till the body structure of the FET device exposed. The etching processes include wet etch, dry etch, plasma etch and/or other suitable processes.

The method 100 then proceeds to block 108 where an interface layer is formed in the opening. The interface layer may be formed on the exposed active region underlying the gate structure of the FET. The interface layer may be compatible (e.g., friendly) for biomolecules or bio-entities binding. For example, the interface layer may provide a binding interface for biomolecules or bio-entities. The interface layer may include a dielectric material, a conductive material, and/or other suitable material for holding a receptor. Exemplary interface materials include high-k dielectric films, metals, metal oxides, dielectrics, and/or other suitable materials. As a further example, exemplary interface materials include $HfO_2$, $Ta_2O_5$, Pt, Au, W, Ti, Al, Cu, oxides of such metals, $SiO_2$, $Si_3N_4$, $Al_2O_3$, $TiO_2$, TiN, SnO, $SnO_2$, $SrTiO_3$, $ZrO_2$, $La_2O_3$; and/or other suitable materials. The interface layer may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer deposition (ALD). In embodiments, the interface layer includes a plurality of layers.

The method 100 then proceeds to block 110 where a receptor such as an enzyme, antibody, ligand, peptide, nucleotide, cell of an organ, organism, or piece of tissue is placed on an interface layer for detection of a target biomolecule.

Figure 2:
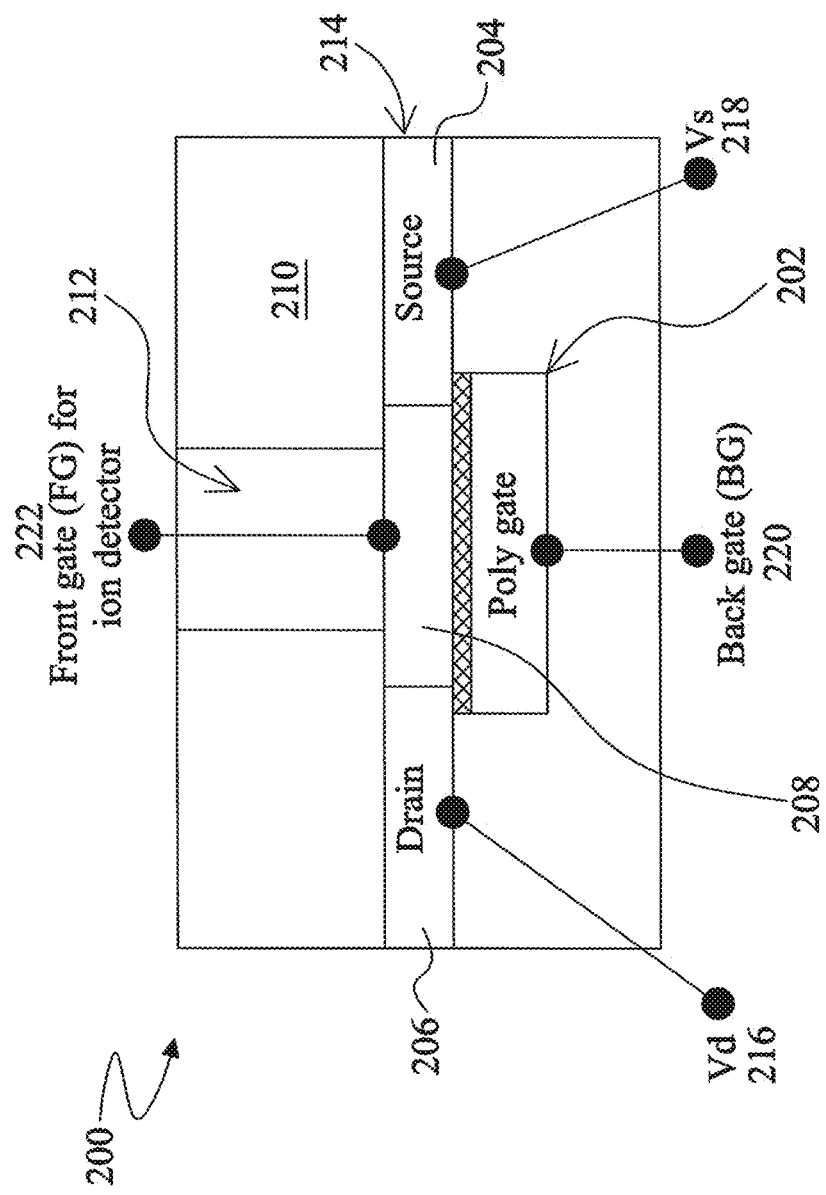
FIG. 2 is a cross-sectional view of an embodiment of a BioFET device according to one or more aspects of the present disclosure.

Referring now to FIG. 2, illustrated is a semiconductor device 200. The semiconductor device 200 may be a BioFET device. The semiconductor device 200 may be formed using one or more aspects of the method 100, described above with reference to FIG. 1.

The semiconductor device 200 includes a gate structure 202 formed on substrate 214. The substrate 214 further includes a source region 204, a drain region 206, and an active region 208 (e.g., including a channel region) interposing the source region 204 and the drain region 206. The gate structure 202, the source region 204, the drain region 206, and the active region 208 may be formed using suitable CMOS process technology. The gate structure 202, the source region 204, the drain region 206, and the active region 208 form a FET. An isolation layer 210 is disposed on the opposing side of the substrate 214, as compared to the gate structure 202 (i.e., backside of the substrate).

An opening 212 is provided in the isolation layer 210. The opening 212 is substantially aligned with the gate structure 202. As described above with reference to block 108 of the method 100 of FIG. 1, an interface layer may be disposed in the opening 212 on the surface of the active region 208. The interface layer may be operable to provide an interface for positioning one or more receptors for detection of biomolecules or bio-entities.

The semiconductor device 200 includes electrical contacts to the source region 206 (Vd 216), the drain region (Vs 218), the gate structure 202 (back gate (BG) 220), and/or the active region 208 (e.g., front gate (FG) 222).

Thus, while a conventional FET uses a gate contact to control conductance of the semiconductor between the source and drain (e.g., the channel), the semiconductor device 200 allows receptors formed on the opposing side of the FET device to control the conductance, while the gate structure 202 (e.g., polysilicon) provides a back gate (e.g., source substrate or body node in a conventional FET). The gate structure 202 provides a back gate that can control the channel electron distribution without a bulk substrate effect. Thus, if the receptors attach to a molecule provided on an interface layer in the opening 212, the resistance of the field-effect transistor channel in the active region 208 is altered. Therefore, the semiconductor device 200 may be used to detect one or more specific biomolecules or bio-entities in the environment around and/or in the opening 212.

The semiconductor device 200 may include additional passive components such as resistors, capacitors, inductors, and/or fuses; and other active components, including P-channel field effect transistors (PFETs), N-channel field effect transistors (NFETs), metal-oxide-semiconductor field effect transistors (MOSFETs), complementary metal-oxide-semiconductor (CMOS) transistors, high voltage transistors, and/or high frequency transistors; other suitable components; and/or combinations thereof. It is further understood that additional features can be added in the semiconductor device 200, and some of the features described below can be replaced or eliminated, for additional embodiments of the semiconductor device 200.

Figure 3:
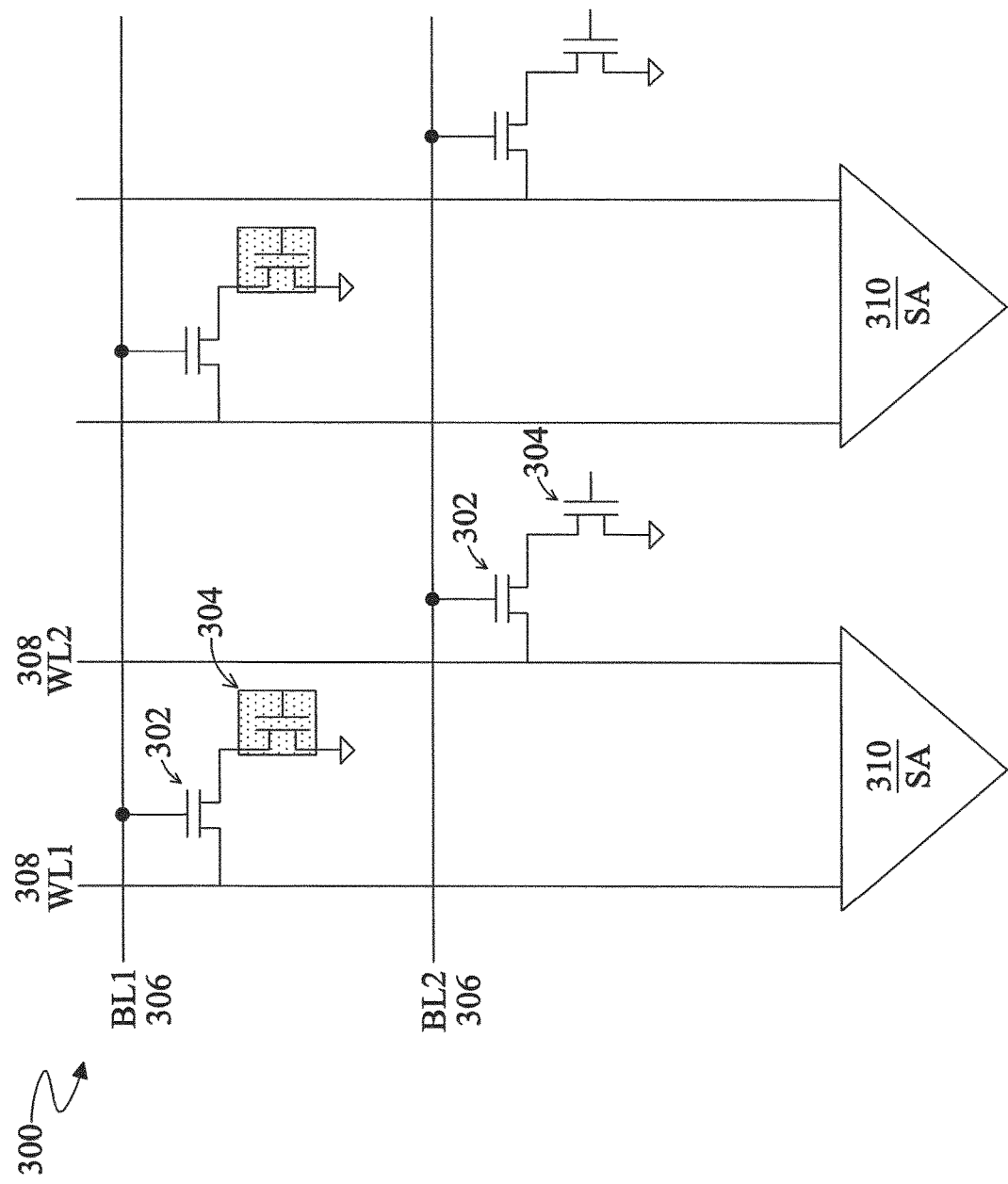
FIG. 3 is a circuit diagram of an embodiment of a plurality of BioFET devices configured in an array arrangement according to one or more aspects of the present disclosure.

Referring now to FIG. 3, illustrated a schematic of a layout 300 of a plurality of semiconductor devices 302 and 304 connected to bit lines 306 and word lines 308. (It is noted that the terms bit lines and word lines are used herein to indicate similarities to array construction in memory devices, however, there is no implication that memory devices or a storage array necessarily be included in the array. However, the layout 300 may have similarities to that employed in other semiconductor devices such as dynamic random access memory (DRAM) arrays. For example, a BioFET such as the semiconductor device 200, described above with reference to FIG. 2, may be formed in a position a capacitor would be found in a traditional DRAM array.) The schematic 300 is exemplary only and one would recognize other configurations are possible.

The semiconductor devices 304 include BioFET devices. The semiconductor devices 304 may be substantially similar to the semiconductor device 200, described above with reference to FIG. 2. The semiconductor devices 302 may include transistors (e.g. control transistors or switching elements) operable to provide connection to the semiconductor device 304 (e.g., BioFET). The semiconductor devices 304 may include a front gate provided by a receptor material formed on a front side of the FET and a back gate provided by a gate structure (e.g., polysilicon).

The schematic 300 includes an array formation that may be advantageous in detecting small signal changes provided by minimal biomolecules or bio-entities introduced to the semiconductor devices 304. Further, this may be accomplished by using a decreased number of input/output pads. The schematic 300 includes sense amplifiers 310. The sense amplifiers 310 may enhance the signal quality and magnification to improve the detection ability of the device having the layout 300. In an embodiment, when particular lines 306 and lines 308 are turned on, the corresponding semiconductor device 302 will be turned on, thus allowing the corresponding semiconductor device 302 to function as in ON-state. When the gate of the associated semiconductor device 304 (e.g., front gate such as gate structure 222 of the semiconductor device 200) is triggered by the bio-molecule presence, the semiconductor device 304 will transfer electrons and induce the field effect charging of the device, thereby modulating the current (e.g., Ids). The change of the current (e.g., Ids) or threshold voltage (Vt) can serve to indicate detection of the relevant biomolecules or bio-entities. Thus, the device having the schematic 300 can achieve a biosensor application including application with differential sensing for enhanced sensitivity.

Figure 4:
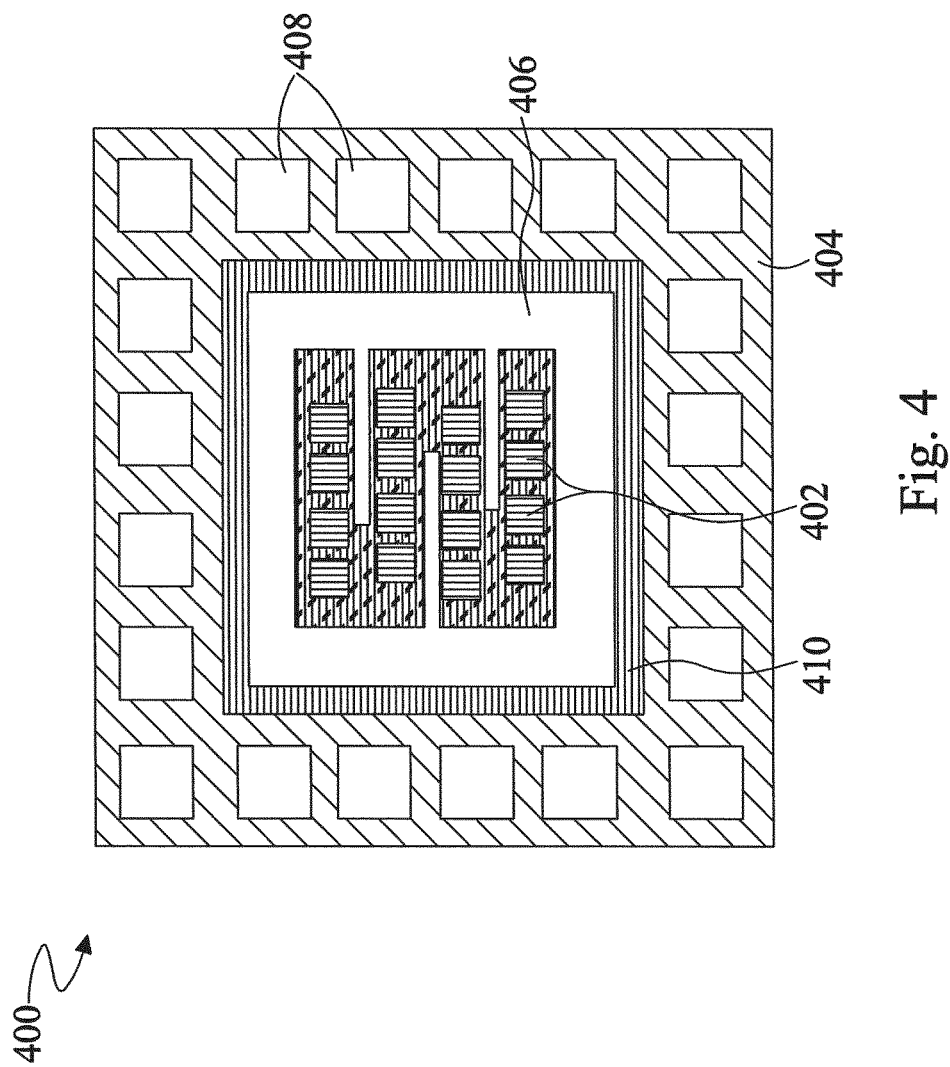
FIG. 4 is a top view of an embodiment of a device including a plurality of BioFET devices formed according to one or more aspects of the present disclosure.
Figure 26:
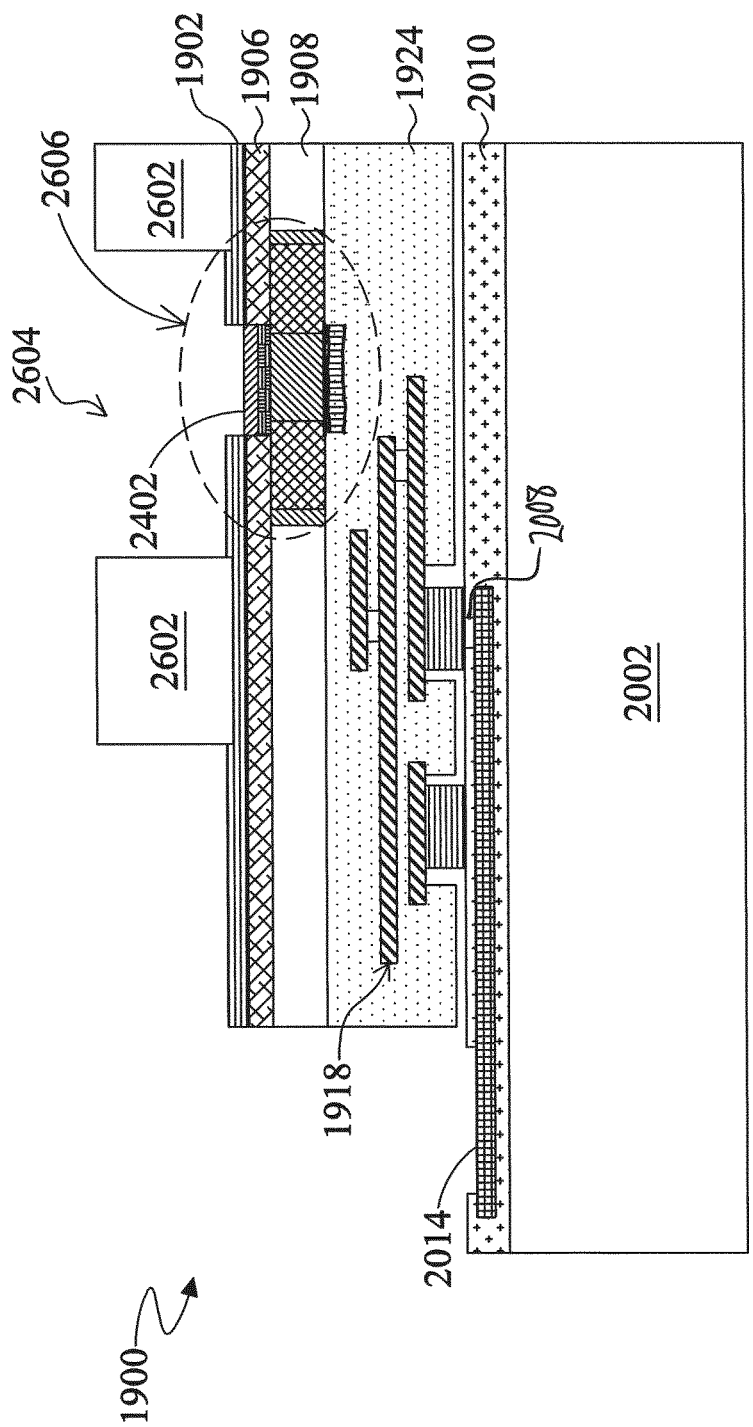

Referring now to FIG. 4, illustrated is a top-view of a semiconductor device 400 for bio-sensing applications. The semiconductor device 400 includes a plurality of BioFETs disposed on a substrate 404. In an embodiment, the semiconductor device 400 may include a layout substantially similar to the layout 300, described above with reference to FIG. 3. The substrate 404 may be a semiconductor substrate and/or a carrier substrate such as discussed with reference to FIG. 1 above, and/or with reference to the detailed description below. The BioFETs may be substantially similar to the semiconductor device 200, described above with reference to FIG. 2, the BioFET 1704, described below with reference to FIG. 17, and/or the BioFET 2606, described below with reference to FIG. 26. An opening is provided in the BioFET devices, such as discussed above with reference to the opening 212 of the semiconductor device 200; this opening may be illustrated as element 402. The opening may also be referred to as a front-gate opening well 402.

A fluidic channel 406 is disposed on the substrate 404. The fluidic channel 406 may provide a channel or container (e.g., reservoir) operable to hold and/or direct a fluid. In an embodiment, the fluidic channel 406 includes polydimethylsiloxane (PDMS) elastomer. However, other embodiments are possible. Typically, the fluidic channel 406 may be fabricated and/or connected or bonded to the device 400 outside of a CMOS process. For example, the fluidic channel 406 may be fabricated and/or connected to the device 400 using processes that are not typical of standard CMOS fabrication. In an embodiment a second entity, separate from the entity fabricating the transistors, may connect the fluidic channel to the substrate 404. The fluid being utilized may be a chemical solution. The fluid may contain target biomolecules or bio-entities.

Peripheral circuitry region 410 surrounds the BioFETs. The peripheral circuitry region 410 may include circuitry to drive and/or sense the variations in the BioFET devices, e.g., including front-gate opening wells 402. The peripheral circuitry may include additional passive components such as resistors, capacitors, inductors, and/or fuses; and other active components, including P-channel field effect transistors (PFETs), N-channel field effect transistors (NFETs), metal-oxide-semiconductor field effect transistors (MOSFETs), complementary metal-oxide-semiconductor transistors (CMOS s), high voltage transistors, and/or other suitable devices.

Figure 12:
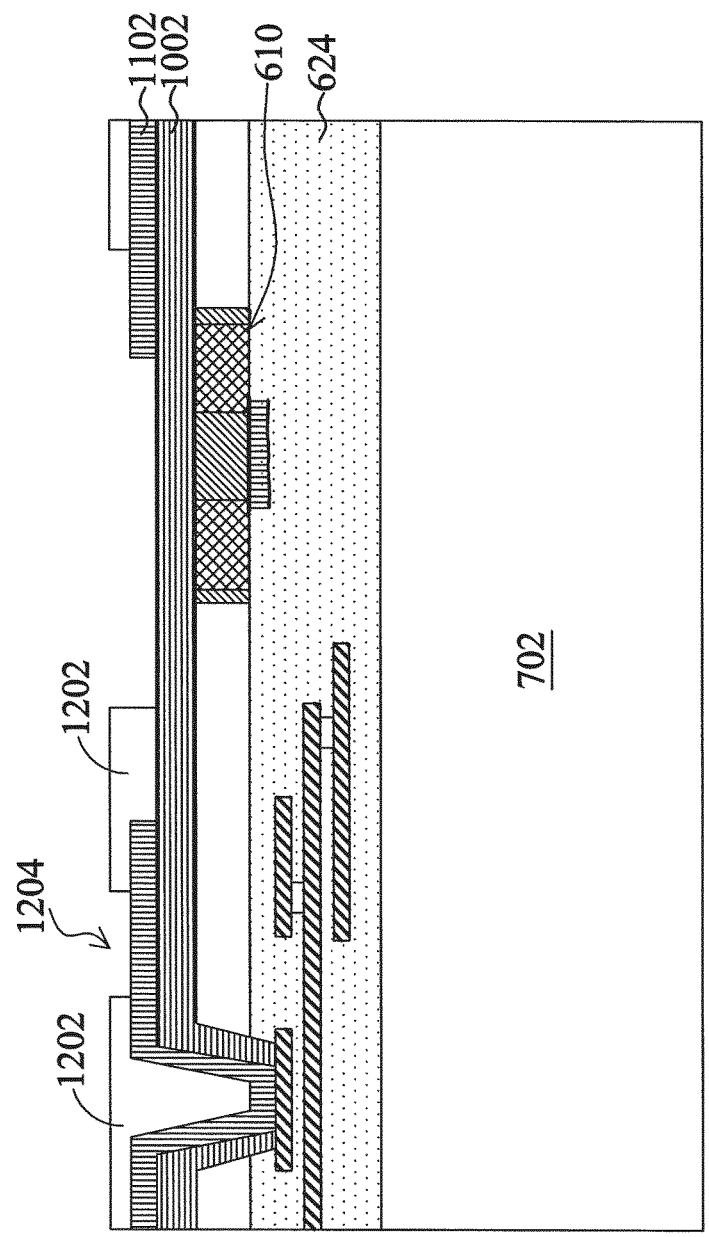

A plurality of bond pads 408 is disposed on the substrate 404. The bond pads 408 may include conductive landings operable to provide a region for wire bonding, ball or bump bonding, and/or other bonding techniques. The bond pads 408 are operable to provide physical and/or electrical connection to other semiconductor devices and/or instrumentations. The bond pads 408 may include any suitable structural material, including copper, aluminum, titanium, tungsten, alloys thereof, composites thereof, combinations thereof, and/or other suitable materials. The bond pads 408 may be substantially similar to the opening 1204 that exposes a conductive pad, described below with reference to FIG. 12 and/or the I/O pad 2014 described below with reference to FIG. 20.

Referring now to FIG. 5, illustrated is a method 500 of fabricating a BioFET device using complementary metal oxide semiconductor (CMOS) compatible process(es). FIGS. 6-17 are cross-sectional views of a semiconductor device 600 according to one embodiment, during various fabrication stages of the method 500. It is understood that additional steps can be provided before, during, and after the method 500, and some of the steps described below can be replaced or eliminated, for additional embodiments of the method. It is further understood that additional features can be added in the semiconductor device 600, and some of the features described below can be replaced or eliminated, for additional embodiments of the semiconductor device 600. The method 500 is one embodiment of the method 100, described above with reference to FIG. 1. Further, the method 500, in whole or in part, may be used to fabricate a semiconductor device such as the semiconductor device 200, described above with reference to FIG. 2, a semiconductor device having the layout 300, described above with reference to FIG. 3, and/or the device 400 described above with reference to FIG. 4.

The method 500 begins at block 502 where a device substrate is provided. Block 502 may be substantially similar to block 102 of the method 100, described above with reference to FIG. 1. The device substrate may be a semiconductor substrate (e.g., wafer). The device substrate may be a silicon substrate. Alternatively, the substrate may comprise another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the device substrate is a semiconductor on insulator (SOI) substrate. The SOI substrate may include a buried oxide (BOX) layer formed by a process such as separation by implanted oxygen (SIMOX), and/or other suitable processes. The device substrate may include doped regions, such as p-wells and n-wells.

Figure 6:
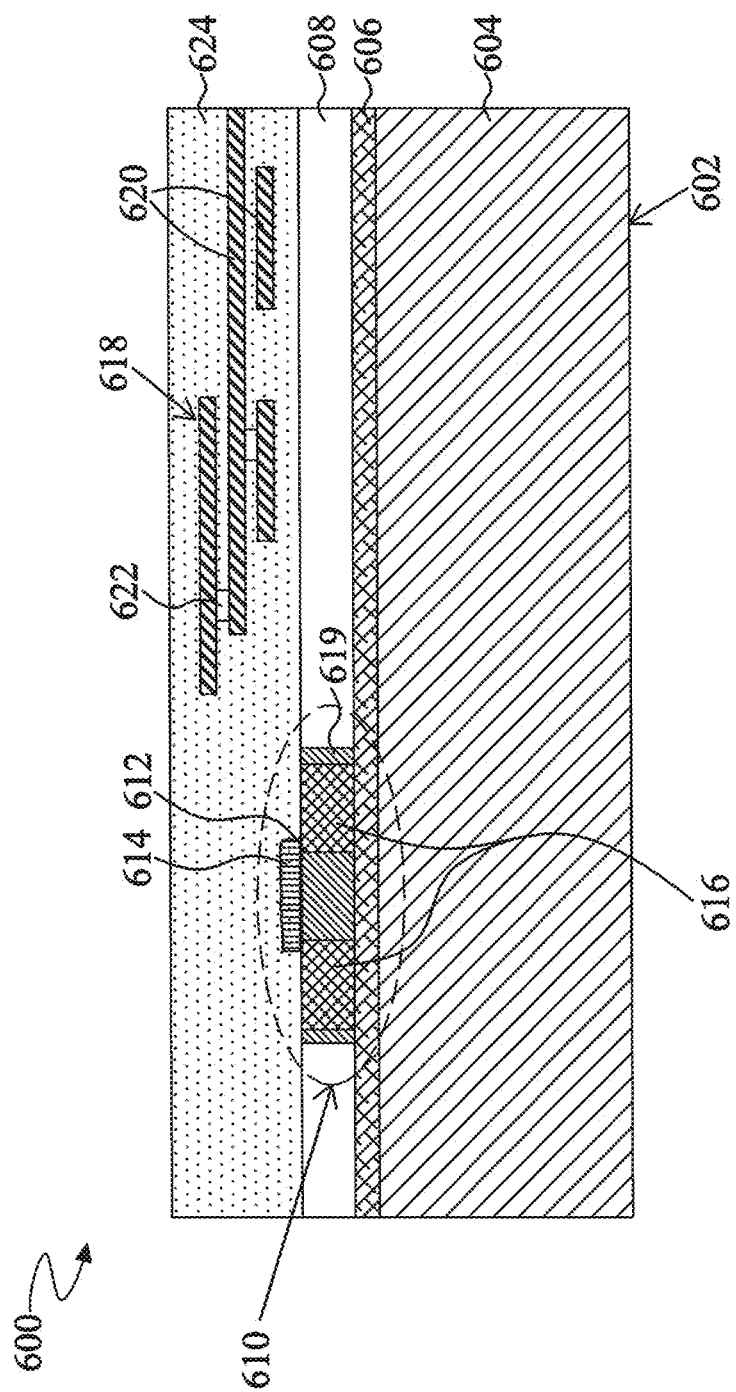
FIGS. 6-17 are cross-sectional views of an embodiment of a BioFET device constructed according to one or more steps of the method of FIG. 5.
Figure 7:
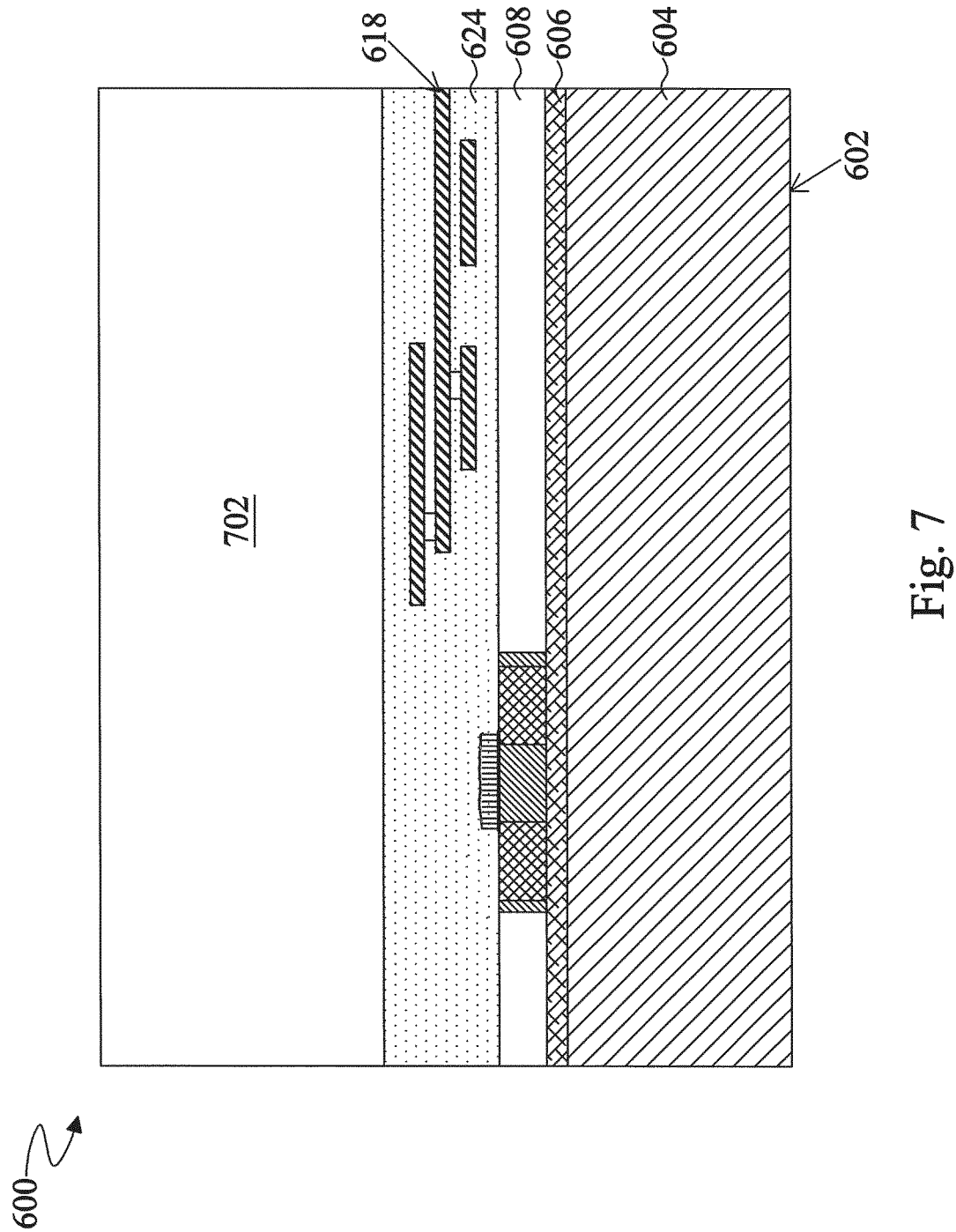

Referring to the example of FIG. 6, a substrate 602 is provided. The substrate 602 is an SOI substrate including a bulk silicon layer 604, an oxide layer 606, and an active layer 608. The oxide layer 606 may be a buried oxide (BOX) layer. In an embodiment, the BOX layer is silicon dioxide ($SiO_2$). The active layer 608 may include silicon. The active layer 608 may be suitably doped with n-type and/or p-type dopants.

The method 500 then proceeds to block 504 where a transistor element is formed on the device substrate. The transistor element may be a field-effect transistor (FET). Block 504 may be substantially similar to block 104 of the method 100, described above with reference to FIG. 1. The transistor element may include a gate structure, a source region, and a drain region. The gate structure includes a gate electrode and an underlying gate dielectric. However, other configurations are possible. In an embodiment, the gate electrode includes polysilicon. Other exemplary compositions of the gate electrode include suitable metals such as, Cu, W, Ti, Ta, Cr, Pt, Ag, Au; suitable metallic compounds like TiN, TaN, NiSi, CoSi; and/or combinations thereof. The gate electrode material may be deposited by physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer deposition (ALD). The deposition may be followed by a photolithography process that patterns the deposited material to form one or more gate structures. The gate dielectric may include dielectric material such as, silicon oxide, silicon nitride, silicon oxynitride, dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($HfO_2$—$Al_2O_3$) alloy, or combinations thereof. The gate dielectric layer may be formed using conventional processes such as, photolithography, oxidation, deposition processes, including those discussed above, etching, and/or a variety of other processes known in the art. The source and/or drain region may be formed by suitable processes such as using photolithography to define a region for ion implantation, diffusion, and/or other suitable processes.

Referring to the example of FIG. 6, a transistor element 610 is disposed on the substrate 602. The transistor element 610 includes a gate dielectric 612, a gate electrode 614, and source/drain regions 616 disposed in a well 618. The source/drain regions 616 and the well 619 may include opposite-type (e.g., n-type, p-type) dopants. In an embodiment, the gate electrode 614 is a polysilicon gate. In an embodiment, the gate dielectric 612 is a gate oxide layer (e.g., $SiO_2$, $HfO_2$).

The method 500 then proceeds to block 506 where a multi-layer interconnect (MLI) structure is formed on the substrate. The MLI structure may include conductive lines, conductive vias, and/or interposing dielectric layers (e.g., interlayer dielectric (ILD)). The MLI structure may provide physical and electrical connection to the transistor, described above with reference to block 504. The conductive lines may comprise copper, aluminum, tungsten, tantalum, titanium, nickel, cobalt, metal silicide, metal nitride, poly silicon, combinations thereof, and/or other materials possibly including one or more layers or linings. The interposing or inter-layer dielectric layers (e.g., ILD layer(s)) may comprise silicon dioxide, fluorinated silicon glass (FGS), SILK (a product of Dow Chemical of Michigan), BLACK DIAMOND (a product of Applied Materials of Santa Clara, Calif.), and/or other insulating materials. The MLI may be formed by suitable processes typical in CMOS fabrication such as CVD, PVD, ALD, plating, spin-on coating, and/or other processes.

Referring to the example of FIG. 6, an MLI structure 618 is disposed on the substrate 602. The MLI structure 618 includes a plurality of conductive lines 620 connected by conductive vias or plugs 622. In an embodiment, the conductive lines 620 include aluminum and/or copper. In an embodiment, the vias 622 include tungsten. In another embodiment, the vias 622 include copper. A dielectric layer 624 is disposed on the substrate 602 including interposing the conductive features of the MLI structure 618. The dielectric layer 624 may be an ILD layer and/or composed of multiple ILD sub-layers. In an embodiment, the dielectric layer 624 includes silicon oxide. The MLI structure 618 may provide electrical connection to the gate 614 and/or the source/drain 616.

The method 500 then proceeds to block 508 where a carrier substrate is attached (e.g., bonded) to the device substrate. The carrier substrate may be attached to the front side of the device substrate. For example, in an embodiment, the carrier substrate is bonded to the ILD layer. In an embodiment, the carrier substrate is bonded to a passivation layer formed on the MLI and/or ILD layers of the substrate. The carrier substrate may be attached to the device substrate using fusion, diffusion, eutectic, and/or other suitable bonding methods. Exemplary compositions for the carrier substrate include silicon, glass, and quartz. Again however, numerous other compositions are possible and within the scope of the present disclosure. Referring to the example of FIG. 7, a carrier substrate 702 is attached to the device substrate 602. In other embodiments, the carrier substrate 702 may include other functionality such as, interconnect features, wafer bonding sites, defined cavities, and/or other suitable features. The carrier substrate may be removed during subsequent processing (e.g., after thinning).

The method 500 then proceeds to block 510 where the device substrate is thinned. The device substrate may be flipped prior to the thinning. The flipped substrate may provide the source/drain regions overlying the gate structure of the transistor described above with reference to block 504. The device substrate may be thinned using wet etch processes, dry etch processes, plasma etch processes, chemical mechanical polish (CMP) processes, and/or other suitable processes for removing portions of the semiconductor substrate. Example etchants suitable for thinning the substrate include HNA (hydrofluoric, nitric, and acetic acid), tetramethylammonium hydroxide (TMAH), KOH, buffered oxide etch (BOE), and/or other suitable etchants compatible with CMOS process technology.

In an embodiment, the device substrate is thinned such that the bulk silicon layer and the buried insulating layer are removed. The device substrate may be thinned in a plurality of process steps, for example, first removing the bulk silicon layer of an SOI wafer followed by removal of a buried insulating layer of the SOI wafer. In an embodiment, a first thinning process includes removal of the bulk silicon using, for example, CMP, HNA, and/or TMAH etching, which stops at the buried oxide layer. The first thinning process may be followed by a second thinning process, such as BOE wet etch, which removes the buried oxide and stops at the silicon of the active layer. The thinning process may expose an active region of the substrate. In an embodiment, a channel region (e.g., active region interposing the source/drain regions and underlying the gate structure) is exposed. The substrate may have a thickness of approximately 500 Angstroms (A) to 1500 A after the thinning process. For example, in one embodiment the active region of an SOI substrate has a thickness of between of approximately 500 A and 1500 A.

In an embodiment, the device substrate is thinned such that the bulk silicon layer is removed, and the buried insulating layer remains on the substrate. The removal of the bulk silicon may be performed using, for example, CMP, HNA, and/or TMAH etching, which stops at the buried insulating layer. The substrate may have a thickness of approximately 500 Angstroms (A) to 1500 A after the thinning process. For example, in one embodiment the active region of an SOI substrate has a thickness of between of approximately 500 A and 1500 A. The buried insulating layer (now providing the surface of the substrate) may perform as an isolation layer such as described below with reference to block 514. Thus, an additional isolation layer does not require deposition.

Figure 8:
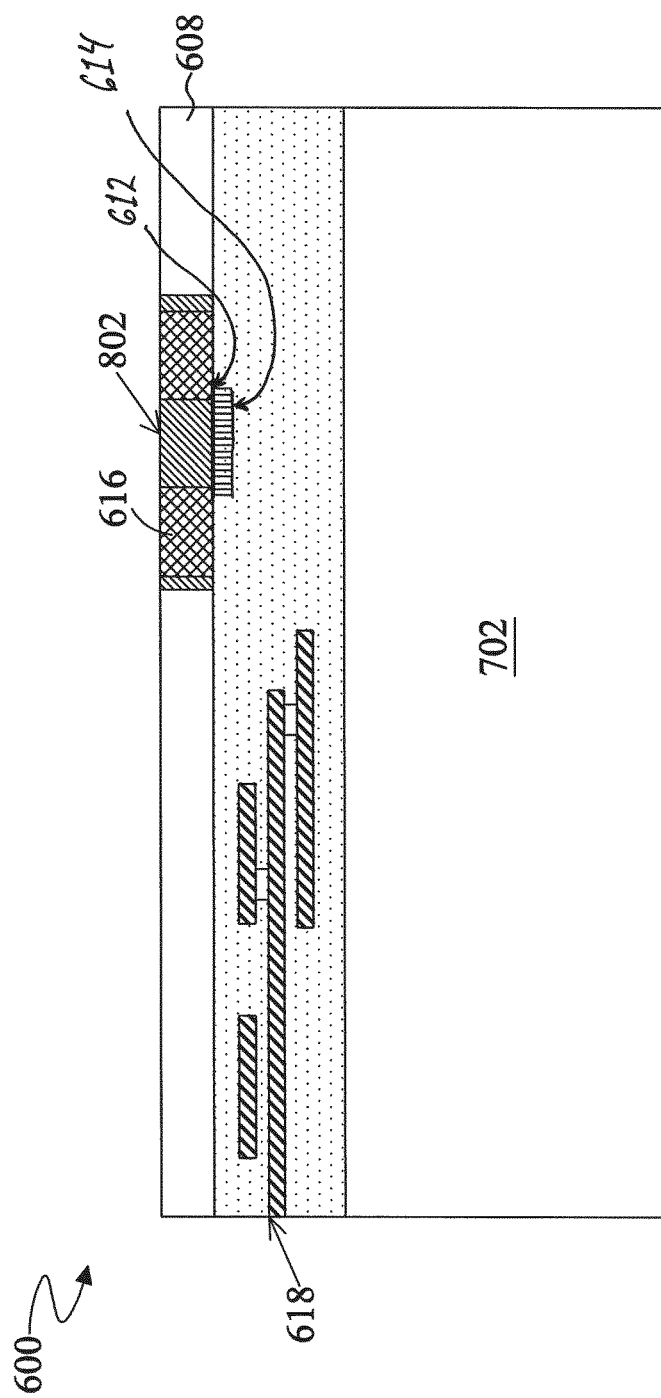
Figure 9:
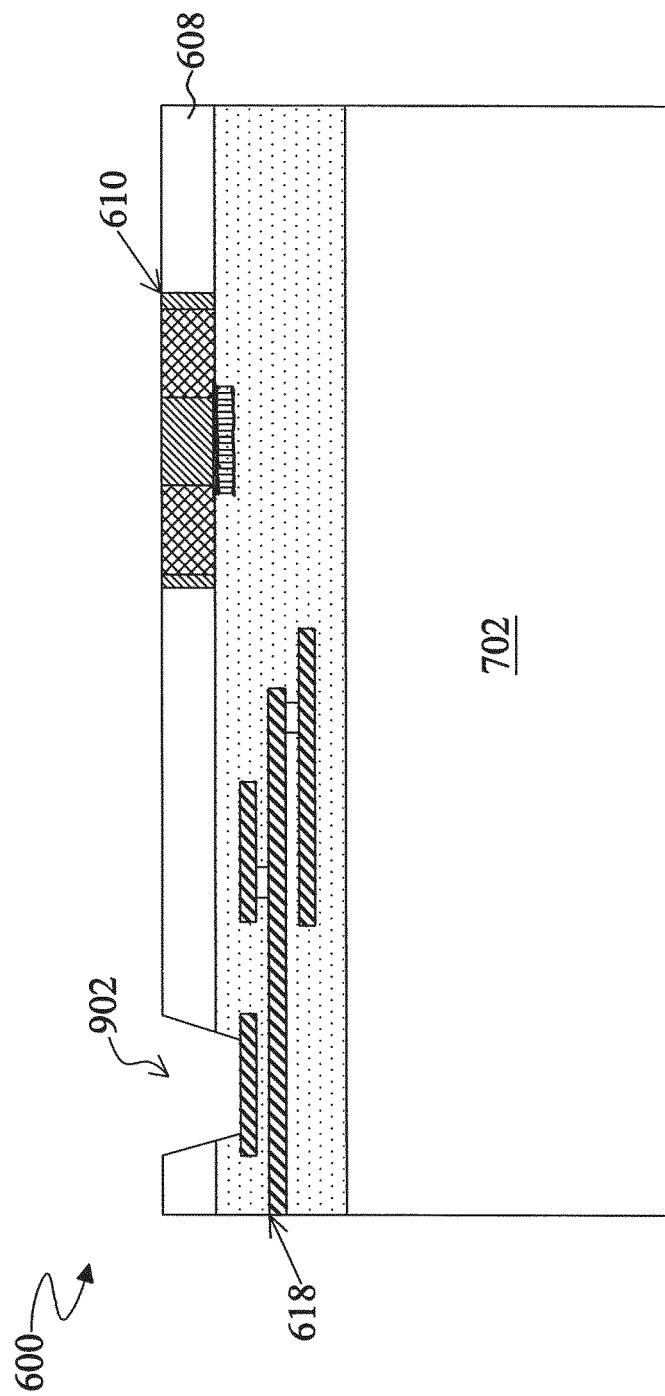
Figure 10:
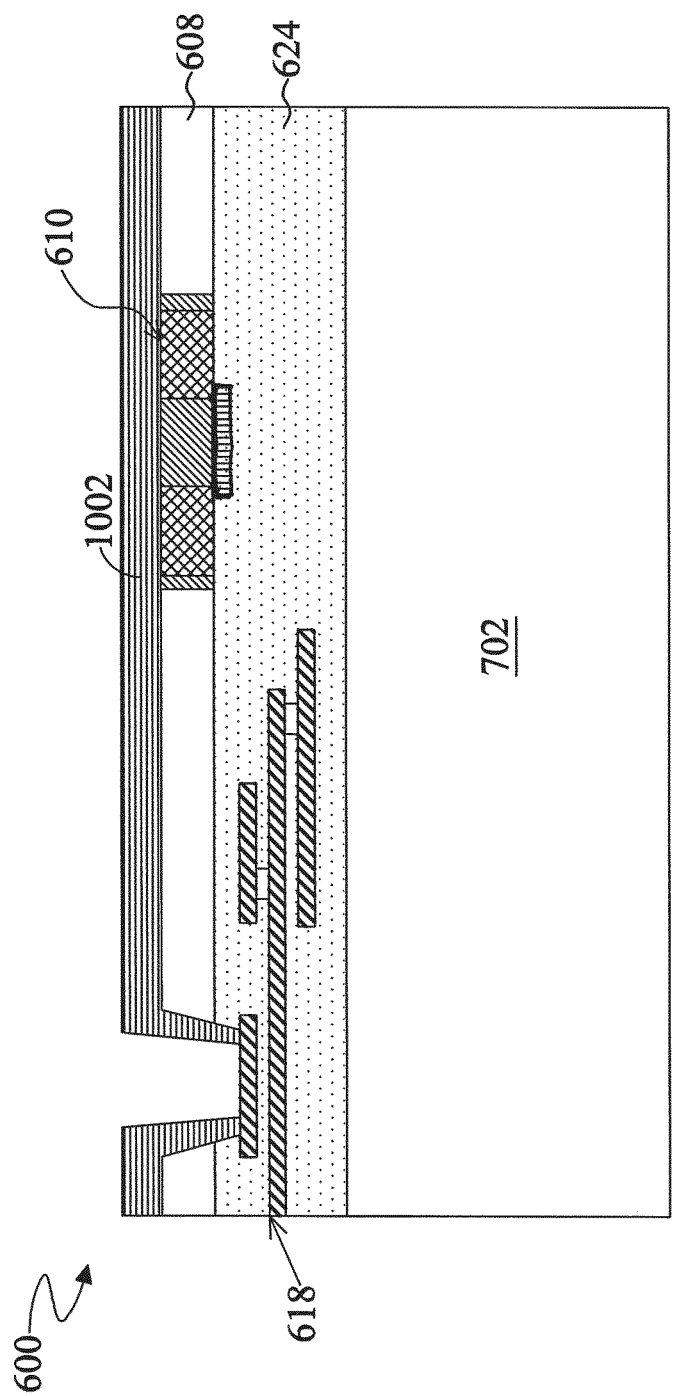
Figure 11:
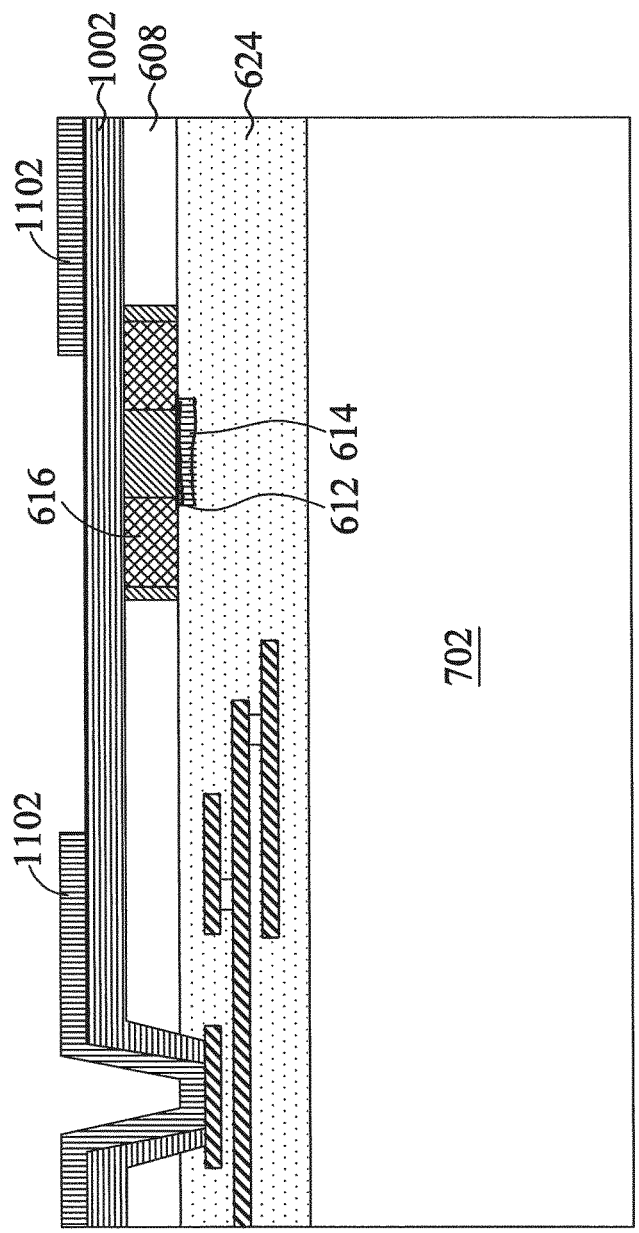

Referring to the example of FIG. 8, the substrate 602 has been thinned removing the bulk silicon layer 604 and the buried oxide layer 606, described above with reference to FIG. 6. The thinning process may include using at least one of the buried oxide layer 606 or the active layer 608 as an etch stop layer. The thinning exposes a channel region 802 (formed in the active layer 608) of the transistor element 610.

In an embodiment, the bulk silicon layer 604 may be removed and the buried oxide layer 606 may remain and function, for example, in addition to or in lieu of an insulating layer 1002, described below.

The method 500 then proceeds to block 512 where a trench is formed on the substrate to expose and provide contact to one or more of the conductive traces of the MLI structure. The trench may be formed by photolithography processes to pattern the trench opening followed by suitable wet, dry or plasma etching processes. In an embodiment, the trench exposes a portion of a metal one (metal 1) layer of the MLI (e.g., the first metal layer formed in the MLI structure after the gate structure is formed). Referring to the example of FIG. 9, a trench 902 is etched in the substrate 602, specifically through the active layer 608, to expose a landing region on a conductive line 620 of the MLI structure 618. Alternatively, the trench may be etched through the isolation region (e.g., oxide).

The method 500 then proceeds to block 514 where an isolation layer is formed on the substrate. The isolation layer may include a dielectric material such as an oxide or nitride. In an embodiment, the isolation layer is silicon oxide. Referring the example of FIG. 10, an isolation layer 1002 is disposed on the active layer 608. In an embodiment, the isolation layer 1002 is silicon dioxide. As discussed above, in an embodiment, an isolation layer is not formed as the insulating layer of the SOI substrate remains on the substrate and functions to replace the need (in whole or in part) for a separate isolation layer.

The method 500 then proceeds to block 516 where an interconnect layer is formed on the isolation layer of described above with reference to block 514. The interconnect layer may provide a connection (e.g., I/O connection) to the MLI structure, described above with reference to block 506. The interconnect layer may provide a connection (e.g., I/O connection) to the transistor 610. The interconnect layer may include a conductive material such as, copper, aluminum, combinations thereof, and/or other suitable conductive material. The interconnect layer may provide functions as a re-distribution layer (RDL). Referring to the example of FIG. 11, an interconnect layer 1102 is disposed on the insulating layer 1002. The interconnect layer 1102 may provide a signal input/output to the transistor 610. In an embodiment, the interconnect layer 1102 includes an aluminum copper alloy.

The method 500 then proceeds to block 518 where a passivation layer is formed on the device substrate. The passivation layer may cover portions of the interconnect layer described above with reference to block 516. The passivation layer may include openings where a bond (e.g., I/O) may be formed. In an embodiment the passivation layer includes silicon dioxide; however, other compositions are possible. The passivation layer may be suitable to provide protection of the device, e.g., the interconnect layer, including from moisture. Referring to the example of FIG. 12, a passivation layer 1202 is formed on the substrate including on the interconnect layer 1102. The passivation layer 1202 includes an opening 1204 where a bond (e.g., wire bond, bump) may provide connection (e.g., I/O connection) to the device 600. In other words, the opening 1204 may expose a conductive 110 pad.

Figure 13:
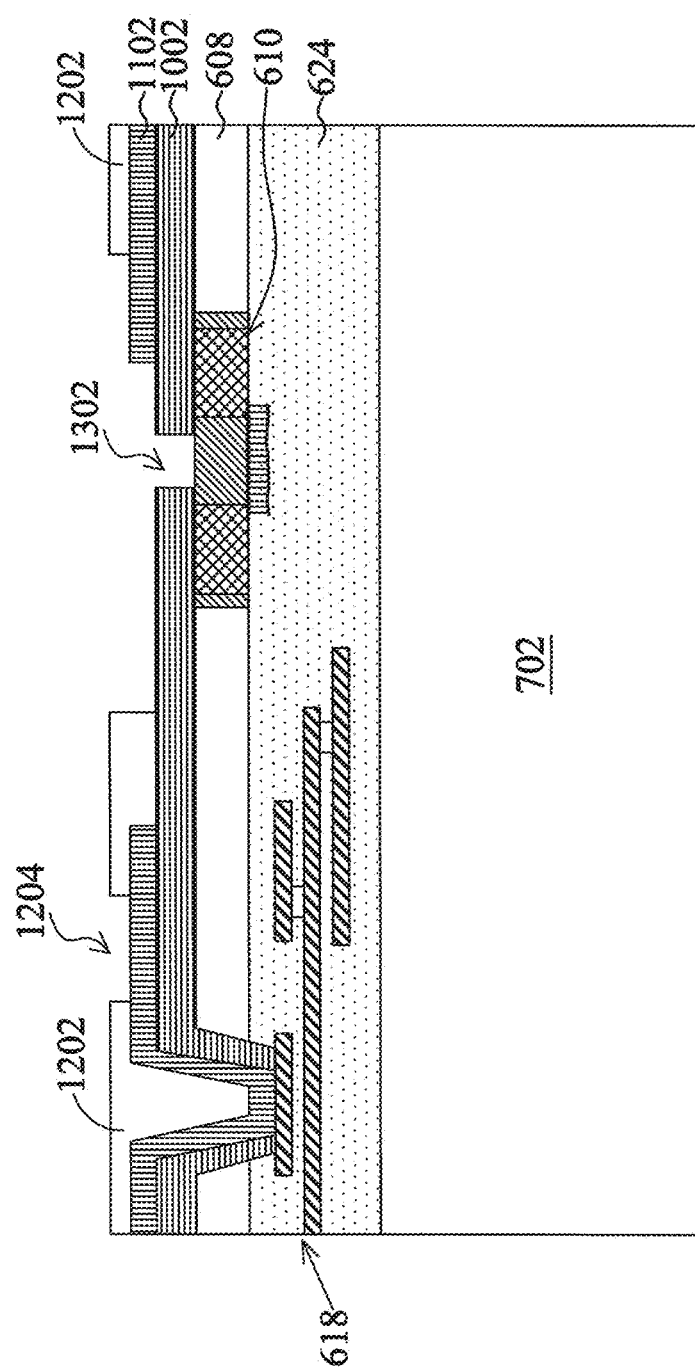
Figure 14:
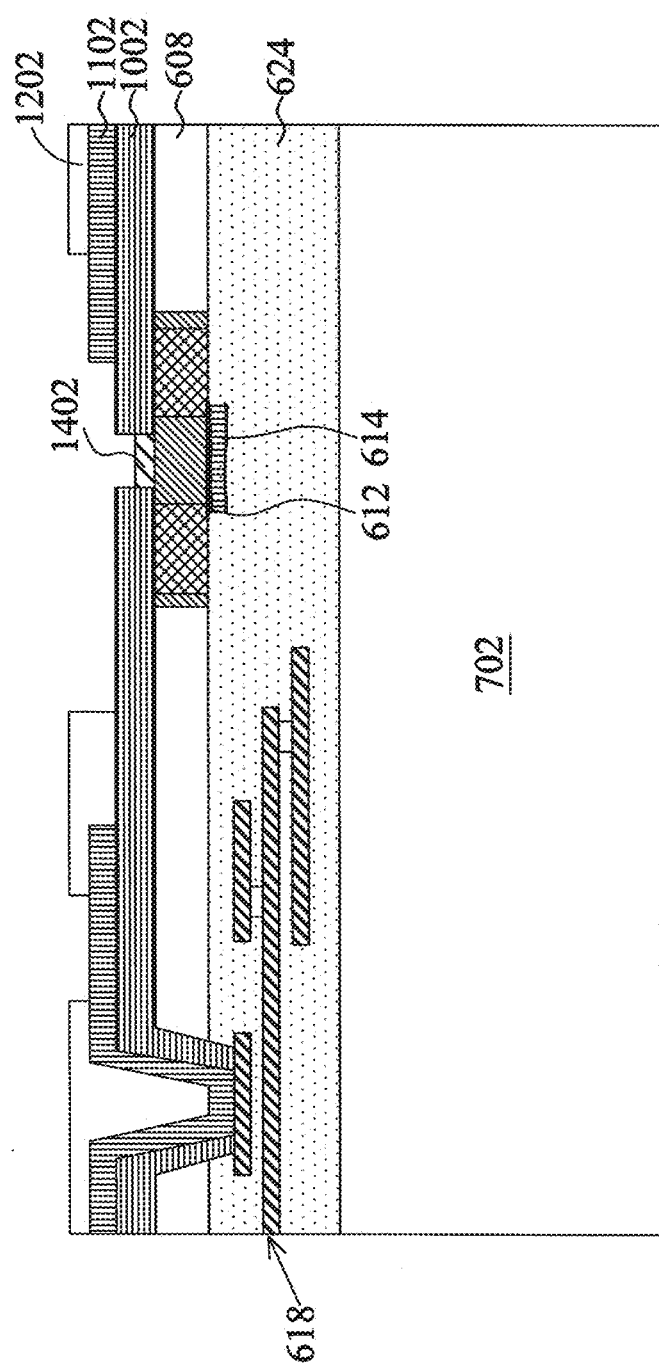
Figure 15:
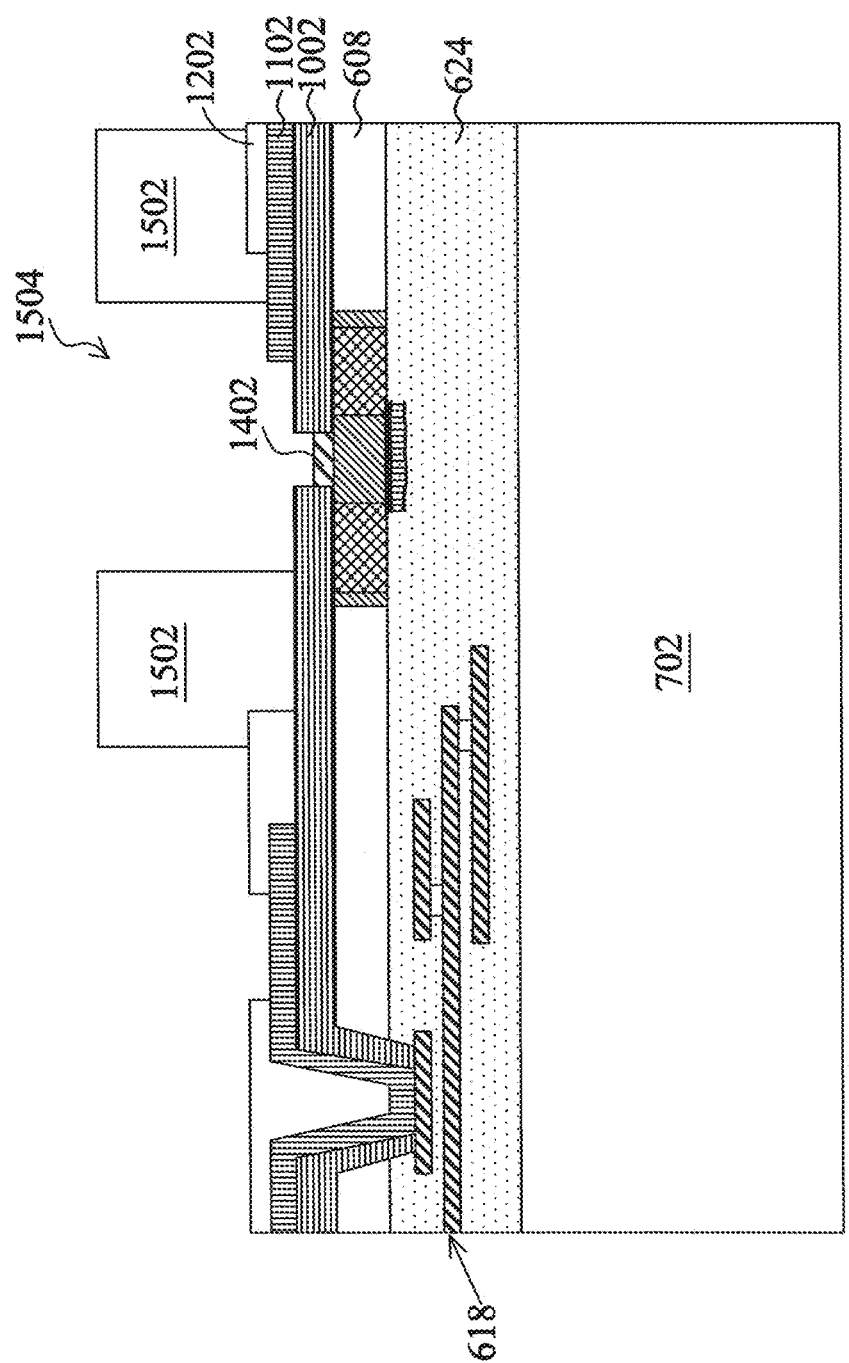

The method 500 then proceeds to block 520 where an opening is formed on the backside of the substrate. The opening may be formed such that a portion of the active region of the substrate underlying the transistor structure (e.g., channel region) is exposed. The opening may be substantially aligned with the gate structure of the transistor. The opening may be formed by suitable photolithography processes followed by an etching process such as a dry etch, wet etch, plasma etch, and/or combinations thereof. In an embodiment, the opening is formed in the isolation layer, described above with reference to block 514. In an embodiment, the opening is formed in the buried insulator layer (of the SOI substrate). Referring to FIG. 13, an opening 1302 is provided. The opening 1302 exposes a portion of the active layer 608. In particular, a channel region 802 of the active layer 608 may be exposed.

The method 500 then proceeds to block 522 where an interface layer is formed on the substrate in the exposed active region provided by the opening. Block 522 may be substantially similar to block 108 of the method 100, described above with reference to FIG. 1. The interface layer may include a material for any specified bio-molecule binding. In an embodiment, the interface layer includes a high-k dielectric material such as, $HfO_2$. In an embodiment, the interface layer includes a metal layer such as Pt, Au, Al, W, Cu, and/or other suitable metal. Other exemplary interface materials include high-k dielectric films, metals, metal oxides, dielectrics, and/or other suitable materials. As a further example, exemplary interface materials include $HfO_2$, $Ta_2O_5$, Pt, Au, W, Ti, Al, Cu, oxides of such metals, $SiO_2$, $Si_3N_4$, $Al_2O_3$, $TiO_2$, TiN, SnO, $SnO_2$; and/or other suitable materials. The interface layer may include a plurality of layers of material. The interface layer may be formed using suitable CMOS processes including CVD, PVD, ALD, and/or other suitable deposition methods. Referring to the example of FIG. 14, an interface layer 1402 is disposed on the active layer 608. The interface layer 1402 can be patterned to be aligned with the gate structure (e.g., is disposed and patterned to remain only in the opening 1302.)

The method 500 then proceeds to block 524 where a fluidic channel is disposed on the device substrate. The fluidic channel may define a region overlying the interface layer such that a solution may be maintained on the interface layer. The fluidic channel may be formed by soft lithography utilizing polydimethylsiloxane (PDMS), wafer bonding methods, and/or other suitable methods. The fluidic channel may be substantially similar to the fluidic channel 406, described above with reference to FIG. 4. Referring to the example of FIG. 15, a fluidic channel 1502 is disposed on the substrate. The fluidic channel 1502 provides a cavity 1504 overlying the interface layer 1402. A solution may be disposed in the cavity 1504, as described in further detail below.

The method 500 then proceeds to block 526 where a receptor is disposed on the interface layer. The receptor may include enzymes, antibodies, ligands, receptors, peptides, nucleotides, cells of organs, organisms and pieces of tissue.

Figure 16:
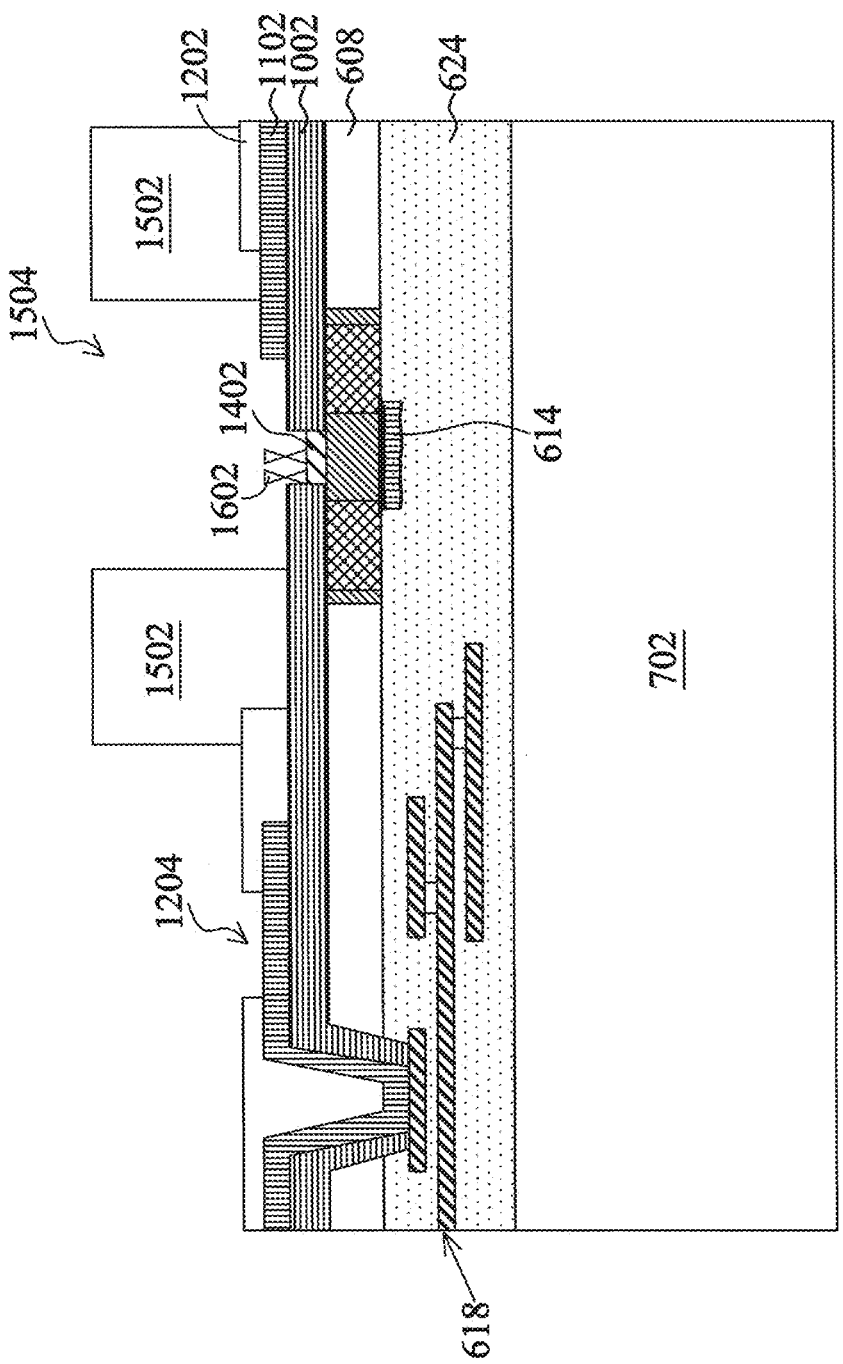

Referring to the example of FIG. 16, a plurality of receptors 1602 is disposed on the interface layer 1042.

The method 500 then proceeds to block 528 where a solution that contains target molecules is provided in the fluidic channel.

Figure 17:
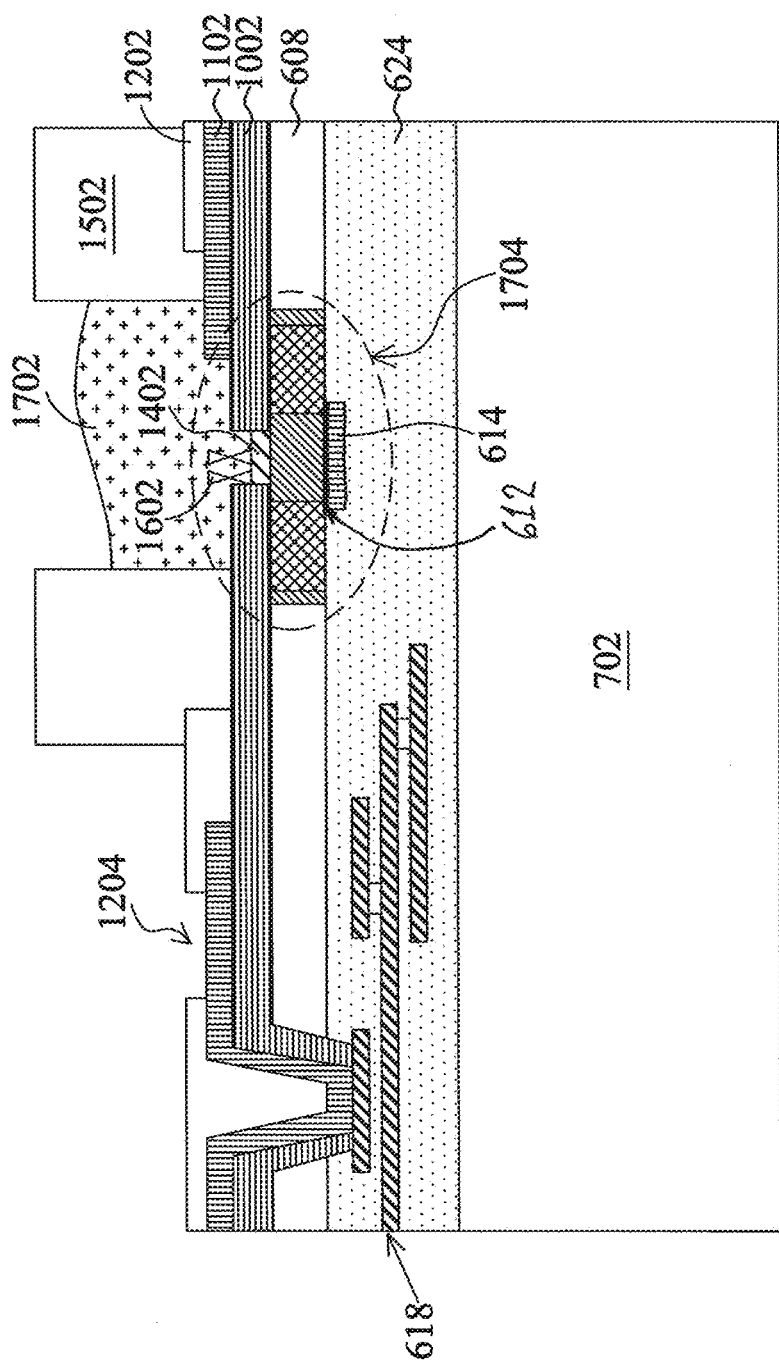

Referring to the example of FIG. 17, a solution 1702 is disposed in the fluidic channel 1502. The solution 1702 contacts the receptors 1602.

In embodiments of the method 500, blocks 524, 526, and/or 528 may be omitted, performed by a different entity, and/or performed outside of a CMOS process.

Thus, the FET 610 is modified to provide the BioFET 1704. The BioFET 1704 allows receptor 1602 to control the conductance of the BioFET 1704, while the gate structure 614 (e.g., polysilicon) provides a back gate. The gate structure 614 provides a back gate that can control the channel electron distribution without a bulk substrate effect. If the receptors 1602 attach to a molecule provided on an interface layer 1402, the resistance of the field-effect transistor channel 802 in the active layer 608 between the source/drain 616 is altered. Therefore, the BioFET 1704 may be used to detect one or more specific molecules, including biomolecules or bio-entities, in the environment around and/or in the opening 1302. The BioFET 1704 may be arranged in an array type pattern such as described above with reference to FIGS. 3 and/or 4. The interconnect 1102 may provide a bias to the BioFET 1704 including, for example, to the front gate or receptor 1602/interface layer 1402 gate.

Referring now to FIG. 18, illustrated is a method 1800 of fabricating a BioFET device using complementary metal oxide semiconductor (CMOS) process(es). FIGS. 19-26 are cross-sectional views of a semiconductor device 1900 according to one embodiment, during various fabrication stages of the method 1800. It is understood that additional steps can be provided before, during, and after the method 1800, and some of the steps described below can be replaced or eliminated, for additional embodiments of the method. It is further understood that additional features can be added in the semiconductor device 1900, and some of the features described below can be replaced or eliminated, for additional embodiments of the semiconductor device 1900. The method 1800 is one embodiment of the method 100, described above with reference to FIG. 1. Further, the method 1900 may be used to fabricate a semiconductor device such as the semiconductor device 200, described above with reference to FIG. 2, a semiconductor device having the layout 300, described above with reference to FIG. 3, and/or the device 400 described above with reference to FIG. 4.

The method 1800 begins at block 1802 where a device substrate is provided. Block 1802 may be substantially similar to block 102 of the method 100, described above with reference to FIG. 1 and/or block 502, described above with reference to the method 500 of FIG. 5. Referring to the example of FIG. 19, a substrate 1902 is provided. The substrate 1902 is an SOI substrate including a bulk silicon layer 1904, an oxide layer 1906, and an active layer 1908. The oxide layer 1906 may be a buried oxide (BOX) layer. In an embodiment, the BOX layer is silicon dioxide ($SiO_2$). The active layer 1908 may include silicon that is suitably doped in various regions.

The method 1800 then proceeds to block 1804 where a transistor element is formed on the device substrate. The transistor element may be a field-effect transistor (FET). Block 1804 may be substantially similar to block 104 of the method 100, described above with reference to FIG. 1, and/or may be substantially similar to block 504 of the method 500, described above with reference to FIG. 5. Referring to the example of FIG. 19, a transistor element 1910 is disposed on the substrate 1902. The transistor element 1910 includes a gate dielectric 1912, a gate electrode 1914, and source/drain regions 1916 disposed in a well 1919. The source/drain regions 1916 and the well 1919 may be regions that include opposite-type (e.g., n-type, p-type) dopants. In an embodiment, the gate electrode 1914 is a polysilicon gate. Other exemplary gate electrodes 1914 include metal. In an embodiment, the gate dielectric 1912 is a gate oxide layer. Other exemplary gate dielectric 912 compositions include high-k dielectrics, nitrides, oxynitrides, and/or other suitable dielectric materials.

Figure 27:
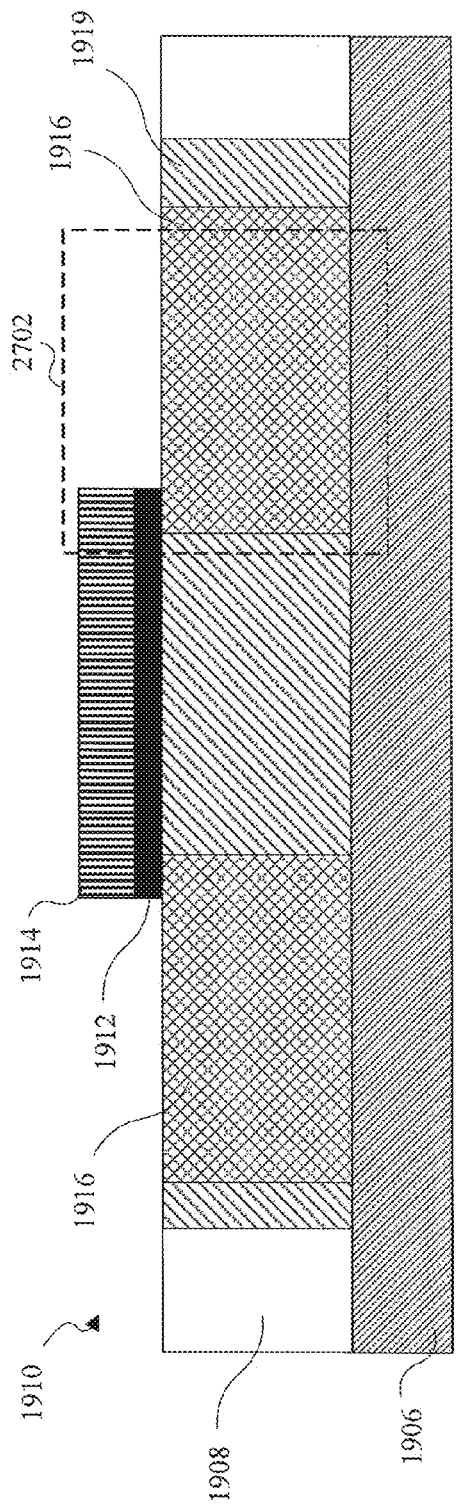
FIG. 27 is a cross-sectional view of an embodiment of a transistor element that forms part of a BioFET device.
Figure 28:
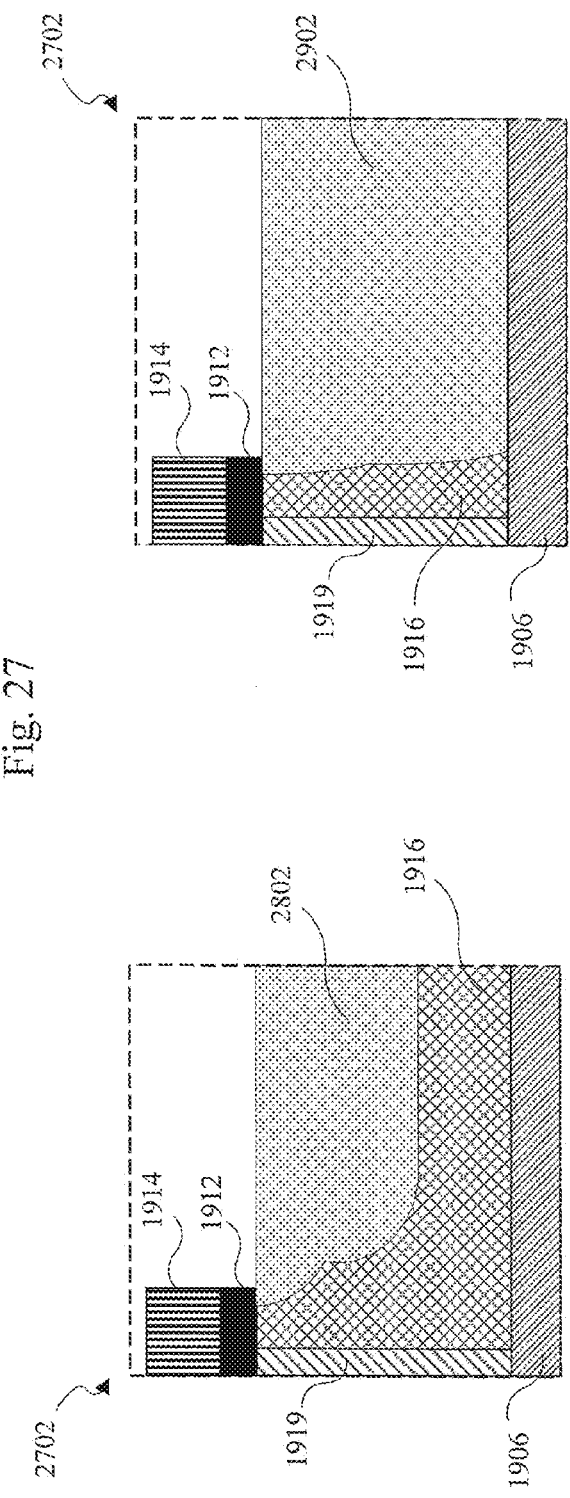
FIG. 28 is a cross-sectional view of a portion of the transistor element of FIG. 27, providing a perspective on the doping profile thereof.

Each of the source/drain regions 1916 has a source/drain profile. Embodiments thereof may be better understood by reference to FIGS. 27, 28, and 29. FIG. 27 is an illustration of transistor element 1910 with a window 2702 that is highlighted in FIGS. 28 and 29. One embodiment of transistor element 1910 is depicted in FIG. 28 as having a doping profile 2802. Doping profile 2802 illustrates the profile formed by the deposition of dopants during the fabrication of source/drain regions 1916. As depicted, the implantation process implanted the dopants, whether n-type or p-type, partway through the active layer 1908. In such embodiments, the dopant profile of source/drain regions 1916 may not extend from a top surface of active layer 1908 to its bottom surface. In contrast, FIG. 29 depicts an embodiment of transistor element 1910 that has a dopant profile 2902 that extends the full thickness of active layer 1908 from the top surface to the bottom surface thereof.

Figure 29:
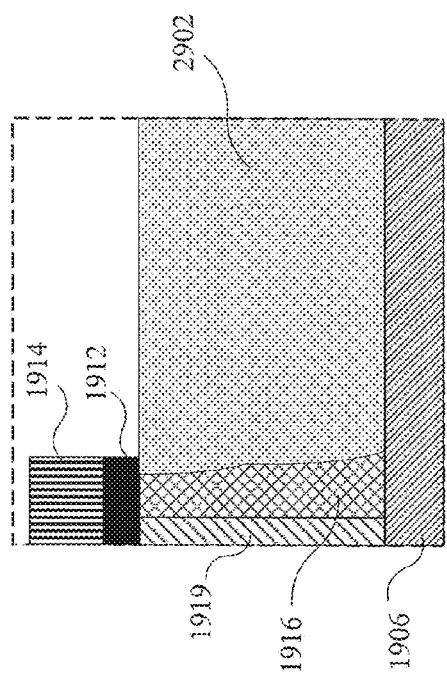
FIG. 29 is a cross-sectional view of a portion of the transistor element of FIG. 27, providing additional detail on the doping profile thereof according to an embodiment.

In order to create embodiments having the dopant profiles similar to dopant profile 2902 of FIG. 29 in extending through active layer 1908, a number of variables are controlled during implantation. These variables include the dopant dosage, implantation direction and energy, as well as the type of dopant uses as some dopants may be heavier than others and some may provide better diffusion. To form dopant profiles like dopant profile 2902, the dopant dosage may range from $10^{10}$ to about $10^{16}$ atoms per cubic centimeter. The acceleration voltage or energy used ranges from about 20 keV to about 200 keV. Some embodiments contain arsenic and/or phorosphorous. By carefully controlling the implantation process, a concentration at the side of active layer 1908 opposite gate electrode 1914 ranges from about $10^{17}$ to about $10^{20}$ per cubic centimeter. The source/drain regions 616 of transistor element 610 as depicted in FIGS. 6-17, and the source 204 and drain 204 of semiconductor device 200 of FIG. 2 also have doping profiles like dopant profile 2902 in some embodiments.

The method 1800 then proceeds to block 1806 where an MLI structure is formed on the substrate. The MLI structure may include conductive lines, conductive vias, and/or interposing dielectric layers (e.g., ILD layer(s)). The MLI structure may provide physical and electrical connection to the transistor, described with reference to block 1804. Block 1806 may be substantially similar to block 506 of the method 500, described above with reference to FIG. 5.

Figure 19:
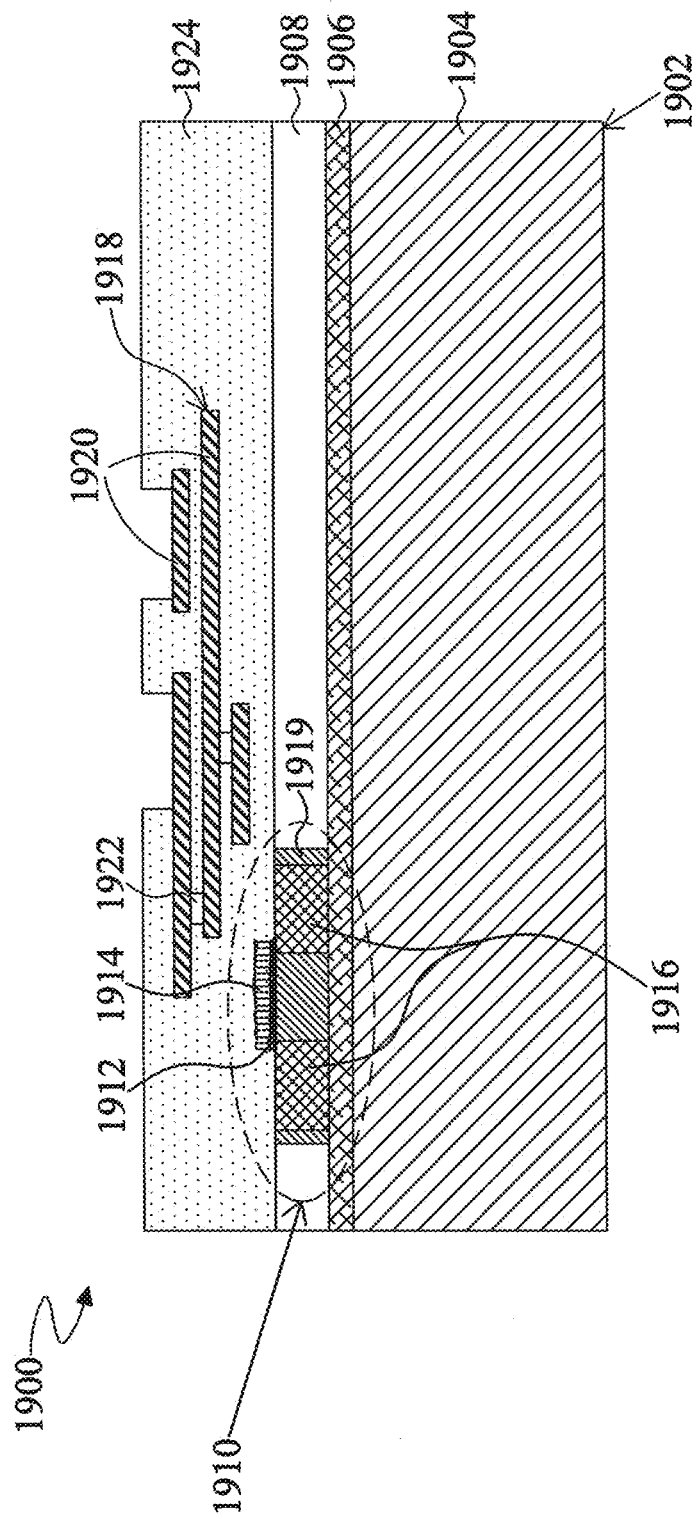
FIGS. 19-26 are cross-sectional views of an embodiment of a BioFET device constructed according to one or more steps of the method of FIG. 18.

Referring to the example of FIG. 19, an MLI structure 1918 is disposed on the substrate 1902. The MLI structure 1918 includes a plurality of conductive lines 1920 connected by conductive vias or plugs 1922. In an embodiment, the conductive lines 1920 include aluminum and/or copper. In an embodiment, the vias 1922 include tungsten. However, other conductive compositions for the conductive lines 1920 and/or vias 1922 are possible. A dielectric layer 1924 is disposed on the substrate 1902 including interposing the conductive features of the MLI structure 1918. The dielectric layer 1924 may be an ILD layer or composed of multiple ILD sub-layers. In an embodiment, the dielectric layer 1924 includes silicon oxide. Again however, other embodiments are possible. The MLI structure 1918 may provide electrical connection to the transistor 1910 including gate 1914 and/or the source/drain 1916.

The method 1800 then proceeds to block 1808 where a carrier (or handling) substrate is attached (e.g., bonded) to the device substrate. The carrier substrate may be attached to the front side of the device substrate. For example, in an embodiment, the carrier substrate is bonded to the ILD layer. In an embodiment, the carrier substrate is bonded to a passivation layer disposed on the MLI and/or ILD layer(s). The carrier substrate may be attached to the device substrate using fusion, diffusion, eutectic, and/or other suitable bonding methods. Exemplary compositions for the carrier substrate include silicon, glass, and quartz. However, numerous other compositions are possible and within the scope of the present disclosure. In an embodiment, one or more conductive layers are provided on the carrier substrate. The conductive layers may be connected (e.g., physically and/or electrically) to one or more devices on the substrate 1902. In an embodiment, the carrier substrate includes a bond pad.

Figure 20:
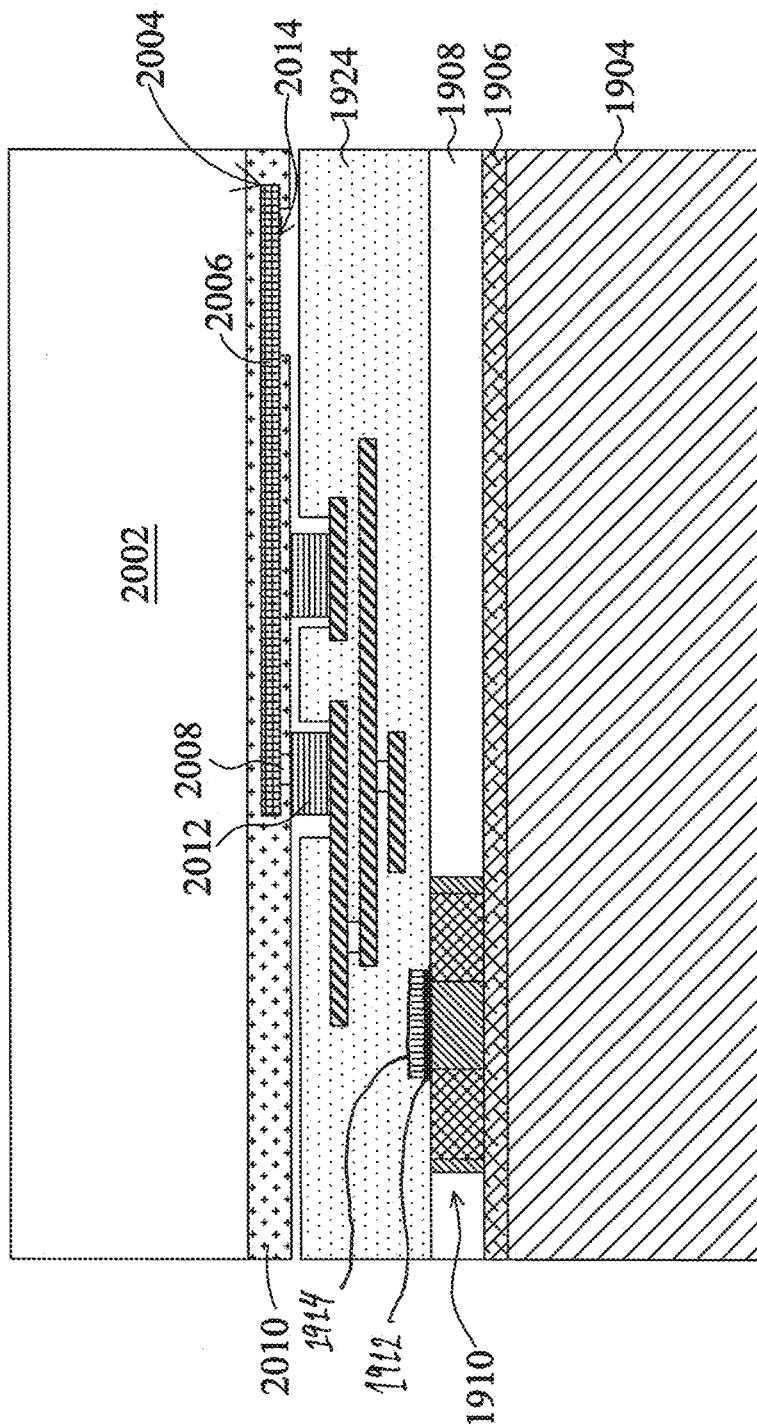
Figure 21:
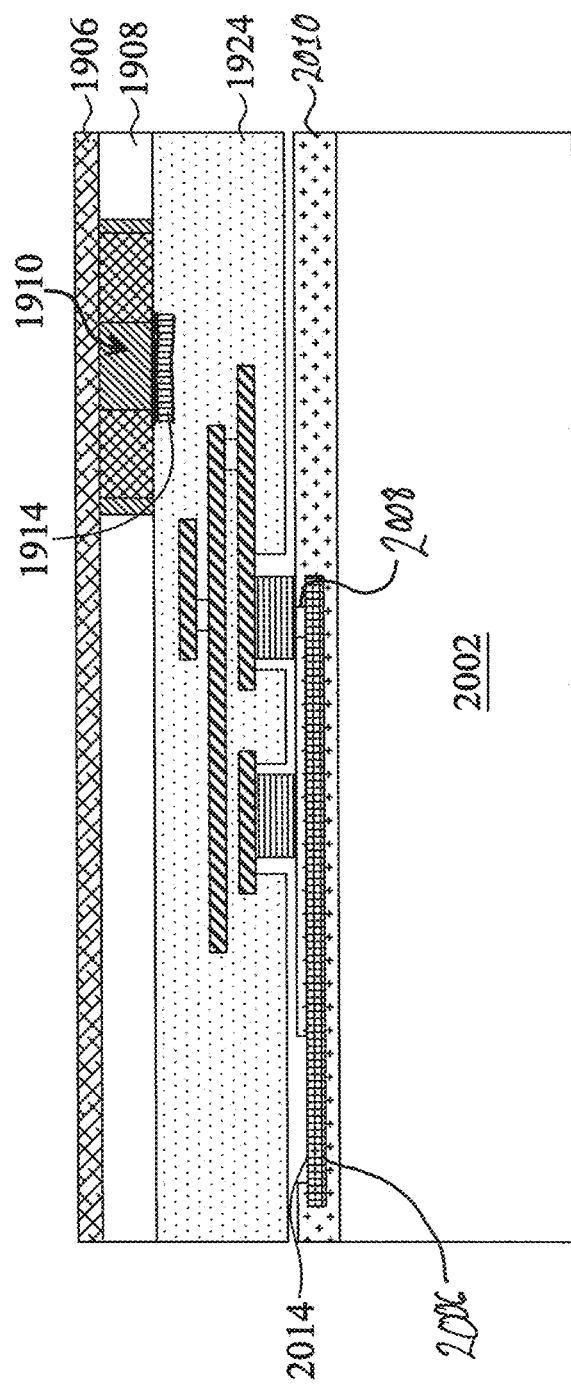
Figure 22:
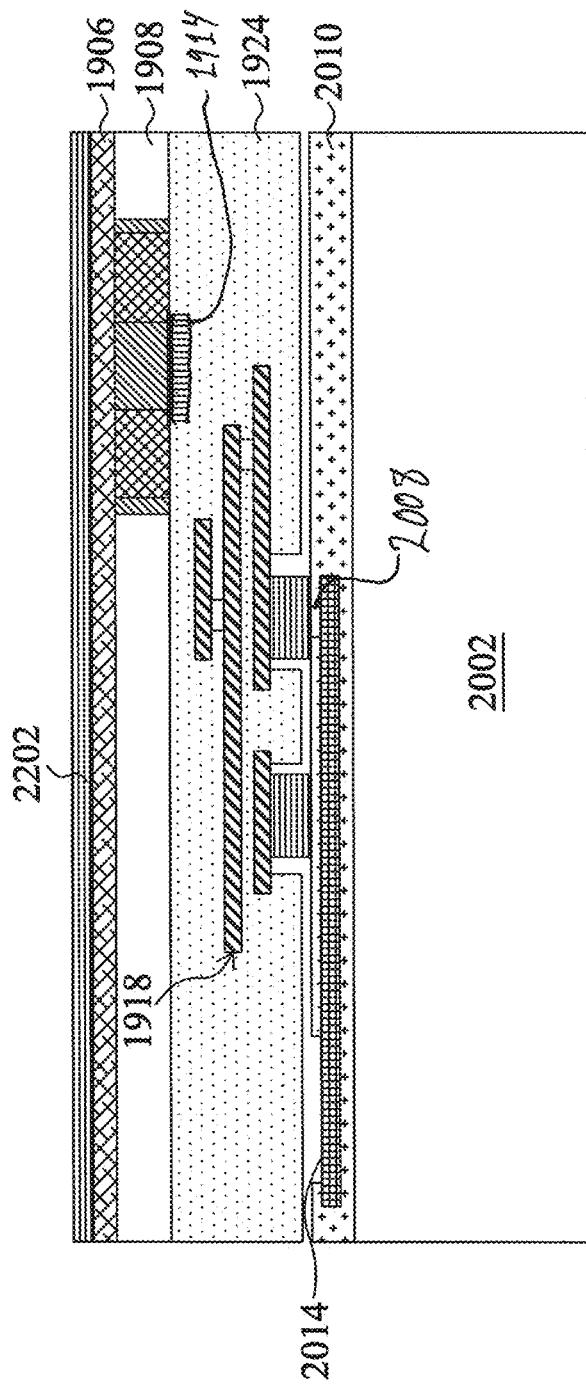
Figure 23:
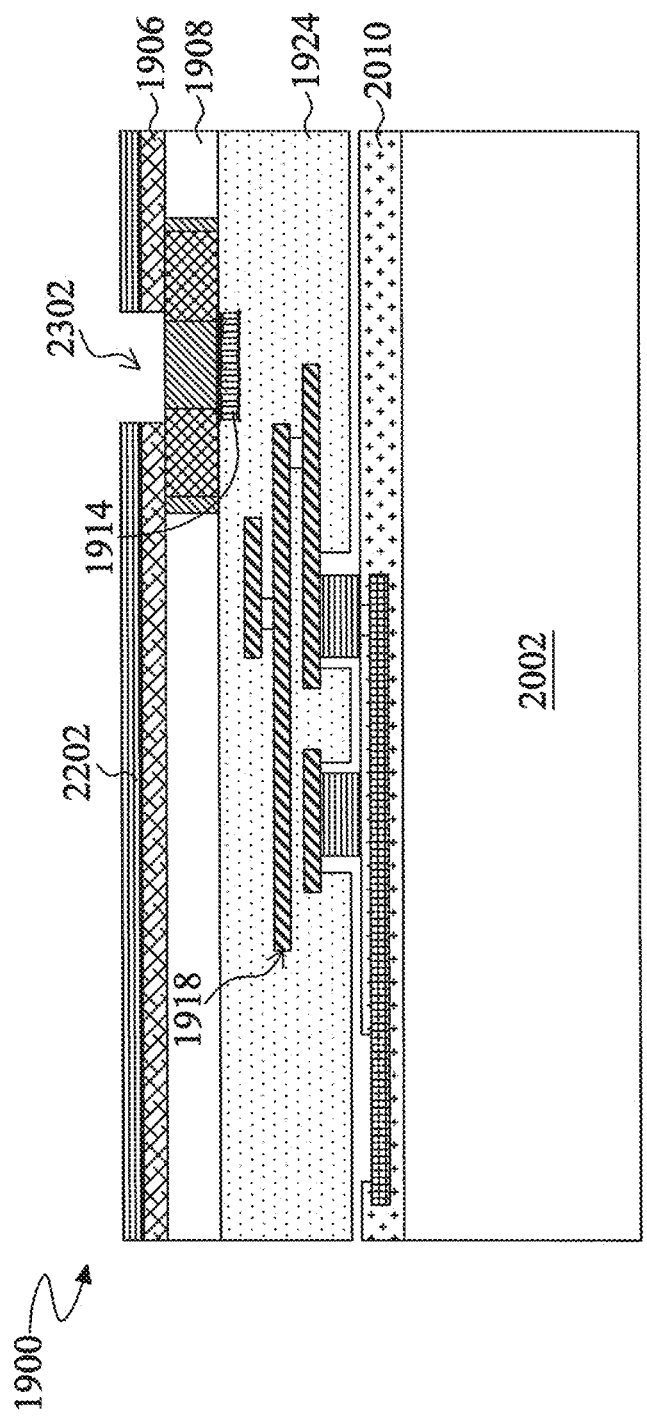
Figure 24:
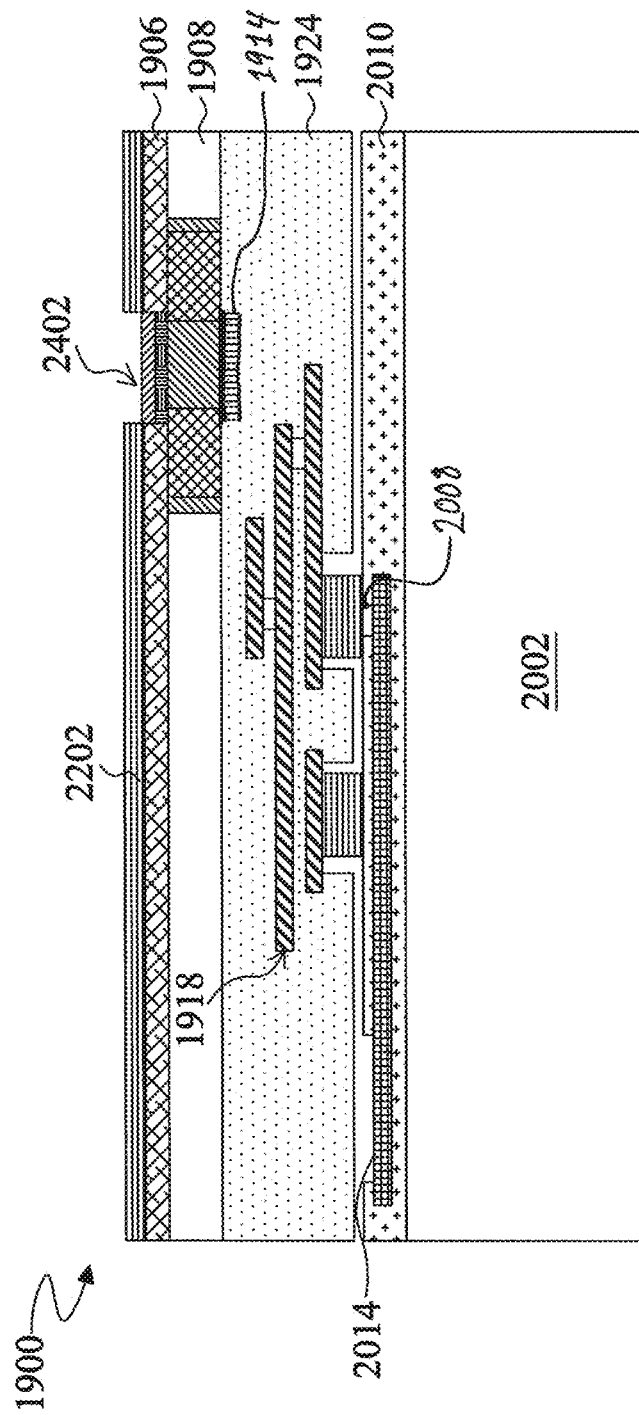
Figure 25:
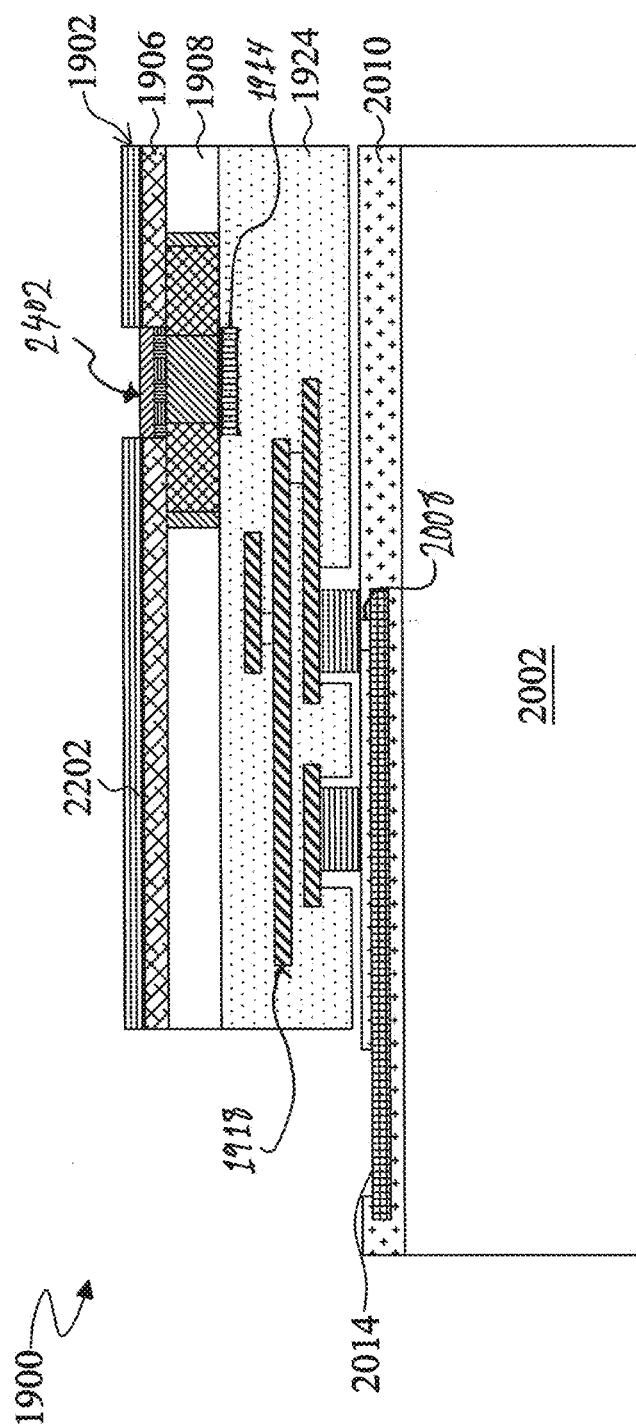

Referring to the example of FIG. 20, a carrier substrate 2002 is attached to the device substrate 1902. In an embodiment, the carrier substrate 2002 is silicon. The carrier substrate 2002 includes an interconnect scheme 2004 including a conductive trace 2006 and via 2008, however other interconnect schemes may be possible including those providing different routings, those including a plurality of layers of conductive traces, and/or other suitable interconnect methods. The interconnect scheme 2004 is disposed in an insulating layer 2010. In an embodiment, the insulating layer is silicon oxide.

The interconnect scheme 2004 includes a bonding element 2012 which is connected (e.g., physically and/or electrically) to the device substrate 1902, for example, to the MLI structure 1918. The bonding element 2012 may include a eutectic bond or metal-to-metal diffusion bond. In an embodiment, the bonding element 2012 is a eutectic bond between germanium and an aluminum cooper alloy. Numerous other eutectic bonding compositions are possible. The interconnect scheme 2004 further includes an I/O pad 2014. The I/O pad 2014 may be suitable for connection to a wire bond, bump, ball, and/or other bonding means to provide connection from the device 1900 to other devices and/or instrumentation.

The method 1800 then proceeds to block 1810 where the device substrate is thinned. Block 1810 may be substantially similar to block 510 of the method 500, described above with reference to FIG. 5. The device substrate may be thinned using wet etch processes, dry etch processes, plasma etch processes, chemical mechanical polish (CMP) processes, and/or other suitable processes for removing portions of the semiconductor substrate. Example etchants include HNA, TMAH, KOH, BOE, and/or other suitable etchants compatible with CMOS process technology. In an embodiment, an SOI substrate is thinned such that a buried insulator (e.g., oxide BOX) remains on the substrate, while the bulk silicon is removed. Referring to the example of FIG. 21, the substrate 1902 has been thinned removing the bulk silicon layer 1904, described above with reference to FIG. 19. The thinning process may include using the buried oxide layer 1906 as an etch stop layer. In other embodiments, the buried oxide layer 1906 may be removed.

The method 1800 then proceeds to block 1812 where an isolation layer is formed on the substrate. The isolation layer may include a dielectric material such as an oxide or nitride. In an embodiment, the isolation layer is silicon nitride. The isolation material may provide a protective barrier (e.g., moisture barrier). Referring the example of FIG. 22, an isolation layer 2202 is disposed on the buried oxide layer 1906 and the active layer 1908. In an embodiment, the isolation layer 2202 is silicon nitride.

The method 1800 then proceeds to block 1814 where an opening is formed on the backside of the substrate. The opening may be formed such that a portion of the active region of the substrate underlying the transistor structure (e.g., channel region) is exposed. The opening may be substantially aligned with the gate structure of the transistor. The opening may be formed by suitable photolithography processes followed by an etching process such as a dry etch, plasma etch, wet etch, and/or combinations thereof. In an embodiment, the opening is formed in the isolation layer, described above with reference to block 1812 and the buried oxide layer of an SOI substrate. Referring to the example of FIG. 23, an opening 2302 is provided. The opening 2302 exposes a portion of the active region 1908. In particular, a channel region of the active region 1908 may be exposed.

The method 1800 then proceeds to block 1816 where an interface layer is formed on the substrate in the opening, for example, on the exposed active region. Block 1816 may be substantially similar to block 108 of the method 100, described above with reference to FIG. 1 and/or may be substantially similar to the block 522 of the method 500, described above with reference to FIG. 5. Referring to the example of FIG. 24, an interface layer 2402 is disposed on the active region 1908. The interface layer 2402 is aligned with the gate structure (e.g., is disposed above the gate structure 1914.) The interface layer 2402 includes a first layer and a second layer. In an embodiment, the first layer is a high-k dielectric material (e.g., $HfO_2$). In an embodiment, the second layer is a metal (e.g., Au). In some embodiments, interface layer 2402 includes only the first layer, and in other embodiments it includes the first layer and a receptor layer.

Figure 30:
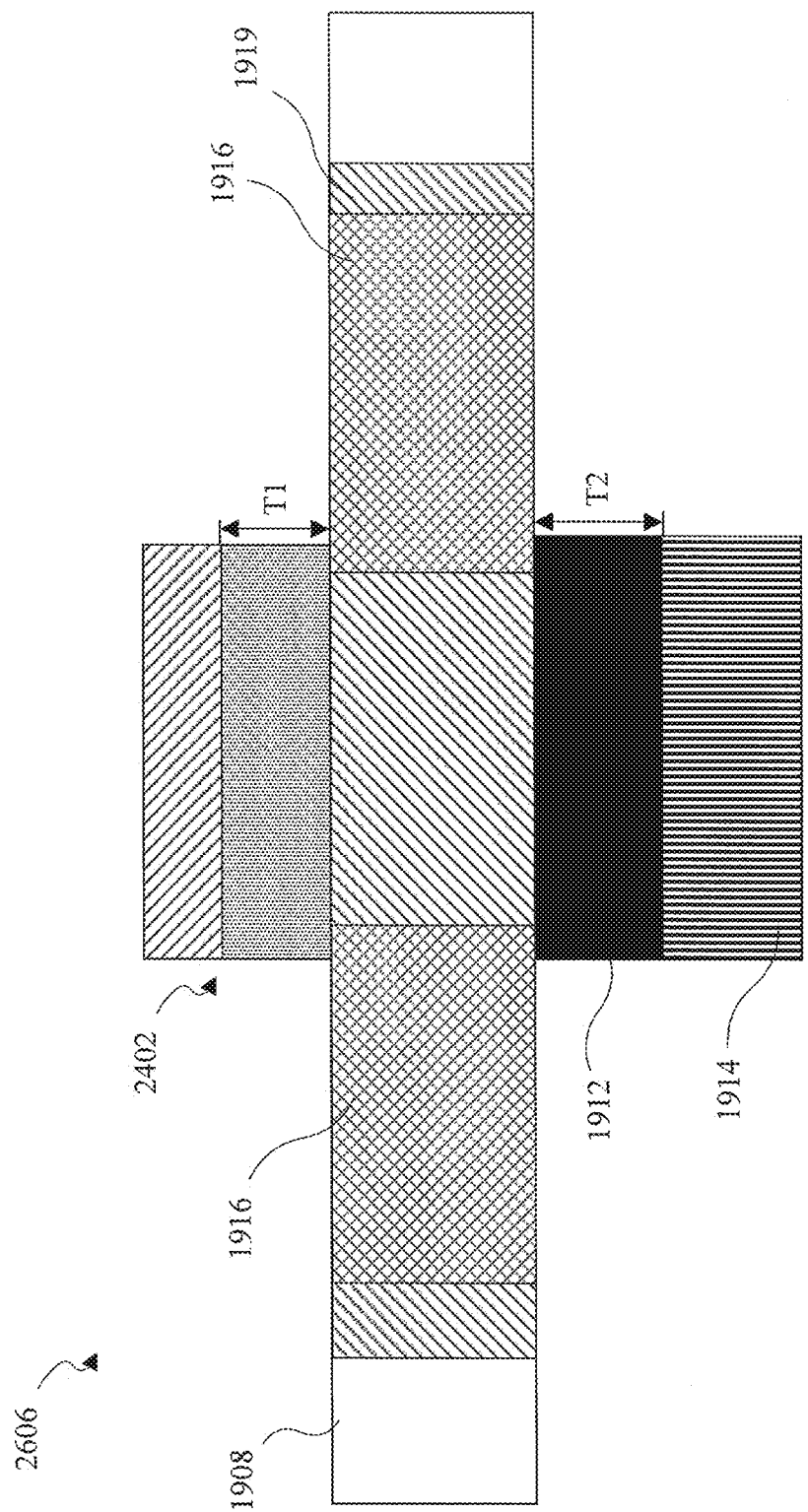
FIG. 30 is a cross-sectional view of a BioFET device.

More detail regarding the interface layer 2402 is found in FIG. 30. FIG. 30 presents a simplified diagram of a BioFET 2606, depicted in context in FIG. 26. FIG. 30 provides detail regarding both interface layer 2402 and the gate dielectric 1912. As described above, interface layer includes a first layer made from a high-k dielectric material and a second layer. In various embodiments, the second layer is a metal layer, a receptor layer, or is entirely absent so that interface layer 2402 has only a single dielectric layer. As discussed above interface layers, such as interface layer 2402 may be formed by a variety of methods including ALD, metal organic chemical vapor deposition (MOCVD), metal deposition and oxidation, and sputtering. In some embodiments, ALD is used to form an interface layer, followed by an annealing step with a forming gas such as ozone, $H_2/N_2$, $Ar/H_2$, or $D_2$.

Interface layer 2402 provides a gate on one side of the active layer 1908, while the gate structure 1914 serves as another gate. The dual gate characteristic of BioFET 2606 is used in some embodiments to provide signal amplification, thereby increasing the sensitivity of BioFET 2606 to target bio-molecules or bio-entities. An amplification provided by BioFET 2606 may be described in the following equation.

$$\frac{\Delta V_{GS_2}}{\Delta V_{GS_1}} = \left(\frac{\mu_1 \left(\frac{W}{L}\right)_1}{\mu_2 \left(\frac{W}{L}\right)_2} \frac{V_{DS_1}}{V_{DS_2}}\right) \frac{C_{OX_1}}{C_{OX_2}} = \alpha \frac{C_{OX_1}}{C_{OX_2}} \quad \text{(Equation 1)}$$

$$\Delta I_{DS2} = \mu_1 \left(\frac{W}{L}\right)_2 V_{DS} \Delta V_{FG2} \quad \text{(Equation 2)}$$

$$\Delta I_{DS1} = \mu_1 1 V_{DS} \Delta V_{FG1} \quad \text{(Equation 3)}$$

The amplification may be adjusted by a number of factors as is apparent from Equation 1. Among that factors that may be used to adjust the amplification factor provided two the two gate structures: the gate dimensions (i.e. width, length, and thickness), the dielectric material or materials used for interface layer 2402 and gate dielectric 1912, and the dielectric constants of the dielectric materials used. In some embodiments, amplification is achieved where $C_{OX1}$ is greater than $C_{OX2}$. In some embodiments, amplification is achieved by having the interface layer 2402 (or the dielectric layer thereof in embodiments having a multi-layered interface layer 2402) be made from a material with a higher dielectric constant than that of a different material used to make gate dielectric 1912. For example, the interface layer 2402 may have a dielectric constant greater than 3.9.

As depicted in FIG. 30, thickness T1 is the thickness of the dielectric layer of interface 2402, while thickness T2 is the thickness of gate dielectric 1912. In some embodiments, amplification is achieved by having effective thickness T2 less than an effective thickness T1. The thickness difference may be as small as a few angstroms to as large as a few hundred angstroms. In some embodiments, an ALD process may be used to form gate dielectric 1912 with a thickness T2 from about 40 to about 60 angstroms and used to form the interface layer 2402 with a thickness T1 from about 20 to about 30 angstroms.

Additionally the transconductance associated with interface layer 2402 (and the semiconductor device aspects associated with it) may be higher than the transconductance associated with gate dielectric 1912 (and the semiconductor device aspects associated with it. This transconductance difference may be generated by having different implantation concentrations in the source/drain regions 1916 on either side of the active layer 1908. Further, amplification may be achieved by having a sub-threshold swing associated with the interface layer 2402 be less than a sub-threshold swing associated with the gate dielectric 1912.

Any combination of the above-mentioned factors may be used in providing an amplification factor to BioFET 2606. Amplification in other embodiments, including the semiconductor device 200 of FIG. 2 and BioFET 1704 as seen in FIG. 17, may be provided as described above.

The method 1800 then proceeds to block 1818 where an I/O bond pad provided on the carrier substrate is exposed. In an embodiment, the device substrate is diced and/or etched such that a conductive pad is exposed on the carrier substrate. The conductive pad or bond pad may provide connection (e.g., I/O connection) to the device 1900. Numerous connection methods may be employed to provide a connection to the device via the bond pad including wire bonding, bumping, conductive ball connections, and/or other suitable I/O connections. Referring to the example of FIG. 25, the device substrate 1902 is diced and/or etched to remove a portion of the substrate 1902 overlying the carrier substrate 2002 including the I/O pad 2014.

The method 1800 then proceeds to block 1820 where a fluidic channel is disposed on the device substrate. The fluidic channel may define a region overlying the interface layer such that a solution may be maintained on the interface layer. The fluidic channel may be formed by PDMS methods, wafer bonding methods, and/or other suitable methods. The fluidic channel may be substantially similar to the fluidic channel 406, described above with reference to FIG. 4. Block 1820 may be substantially similar to block 524 of the method 500, described above with reference to FIG. 5. In an embodiment, block 1820 is provided prior to block 1818 of the method 1800. Referring to the example of FIG. 26, a fluidic channel 2602 is disposed on the substrate. The fluidic channel 2602 provides a cavity 2604 overlying the interface layer 2402. A solution may be disposed in the cavity 2604.

The method 1800 then proceeds to block 1822 where a receptor is disposed on the interface layer. Block 1822 may be substantially similar to block 526 of the method 500, described above with reference to FIG. 5. The method 1800 then proceeds to block 1824 where an ionic solution is provided in the fluidic channel. Block 1824 may be substantially similar to block 528 of the method 500, described above with reference to FIG. 5. In embodiments of the method 1800, blocks 1820, 1822, and/or 1824 may be omitted, performed by a different entity, and/or performed outside of a CMOS process.

Thus, the FET 1910 is modified to form the BioFET 2606. The BioFET 2606 allows receptor to control the conductance of the BioFET 2606, while the gate structure 1914 (e.g., polysilicon) provides a back gate. The gate structure 1914 provides a back gate that can control the channel electron distribution without a bulk substrate effect. If the receptors attach to a molecule, the resistance of the field-effect transistor channel in the active region 1908 between the source/drain 1916 is altered. Therefore, the BioFET 2606 may be used to detect one or more specific molecules, including biomolecules or bio-entities, in the environment around and/or in the opening 2302. The BioFET 2606 may be arranged in an array type pattern such as described above with reference to FIGS. 3 and/or 4. The interconnect 2014 may provide a bias to the BioFET 2606 including, for example, to the front gate or receptor/interface layer.

In an embodiment, a CMOS fabrication facility (e.g., foundry) may process the method 500 and/or the associated device up to the fluidic channel formation. In an embodiment, a subsequent user may provide the surface treatment technologies, ionic solutions, receptors, and the like. For example, a foundry may provide a device such as described above with reference to FIGS. 14 and/or 25 to a user (e.g., customer).

In summary, the methods and devices disclosed herein provide a BioFET that is fabricated using CMOS and/or CMOS compatible processes. Some embodiments of the disclosed BioFET may be used in biological and/or medical applications, including those involving liquids, biological entities, and/or reagents. One detection mechanism of some embodiments described herein includes a conductance modulation of the FET of the BioFET due to the binding of the target bio-molecule or bio-entity to the gate structure, or a receptor molecule disposed (e.g., immobilized) on the gate structure of a device.

Some embodiments of the BioFET described herein include an inverted FET, which may be fabricated at least in part using conventional processes. Specifically, a backside of a CMOS FET is opened (e.g., at well gate). A biocompatible interface materials and receptor material are placed in this opening such that the presences of a bio-entity binding can be detected by the change in performance (e.g., current) of the resistor. Thus, in some embodiments, the transistor, includes a source/drain region (e.g., formed as a conventional FET) and a fluidic gate structure including a dielectric film and/or metal stack on top of the dielectric film for biosensing. A passivation layer may protect the newly formed "transistor" from surrounding liquid(s). In some embodiments, the device includes conductive (metal) layers and routings along with inter-layer or inter-metal dielectric circuitry and I/O connections lying underneath the source/drain regions.

Some embodiments of the BioFETs are arranged in an array form. They may include a back-gate for back-gate biasing to improve respond time and/or enhance sensitivity. The gate structures may be built on silicon-on-insulator (SOI) substrates. This may provide advantages in some embodiments of operation at a higher speed and/or consumption of less power. The inverted transistor provided on an SOI substrate may achieve improved fabrication uniformity, improved process control, and the like. Some embodiments may provide for an improved short-channel effect, for example, due to the formation on a SOI substrate.

In describing one or more of these embodiments, the present disclosure may offer several advantages over prior art devices. In the discussion of the advantages or benefits that follows it should be noted that these benefits and/or results may be present is some embodiments, but are not required. Advantages of some embodiments of the present disclosure include the ability to offer a customer-customizable product. For example, fluidic channel formation, receptor introduction and the like may be performed by a customer. Other examples of embodiments include provision of a bio-friendly interface material. As a further example of advantages of one or more embodiments described herein, in conventional devices it is typical to require high aspect ratio processing to form a bio-compatible interface (e.g., requiring etching from a front surface of the substrate to a gate structure). Because the present methods provide for processing on a backside of a thinned wafer, the aspect ratio may be reduced. The resultant device may be beneficial in that the backside gate can easily control the channel electrode distribution and reduce the bulk substrate effect as it is provided by the gate structure (e.g., polysilicon electrode) rather than the substrate.

Further exemplary advantages of some embodiments include, but are not limited to, separated electrical and fluidic elements, which may be optimized independently without cross-interference. The separated electrical and fluidic elements may also or alternatively minimize an impact of signal attenuation due to parasitic capacitance (e.g., of metal layers). Further exemplary advantages of some embodiments include the ability to select suitable materials for the fluidic gate based on desired design goals, such as, for example, improved association and dissociation capabilities and binding capacity based on a designer's selection of fluidic gate materials (dielectric and/or metal); minimized leakage current due to choices of fluidic gate materials (e.g., dielectric) with larger conduction band offset; enhanced sensitivity due to the designers choice of fluidic gate materials with higher dielectric constant and/or metal conductivity; improved liquid resistance due to the designer's choice of fluidic gate materials; and/or other advantages.

Figure 31:
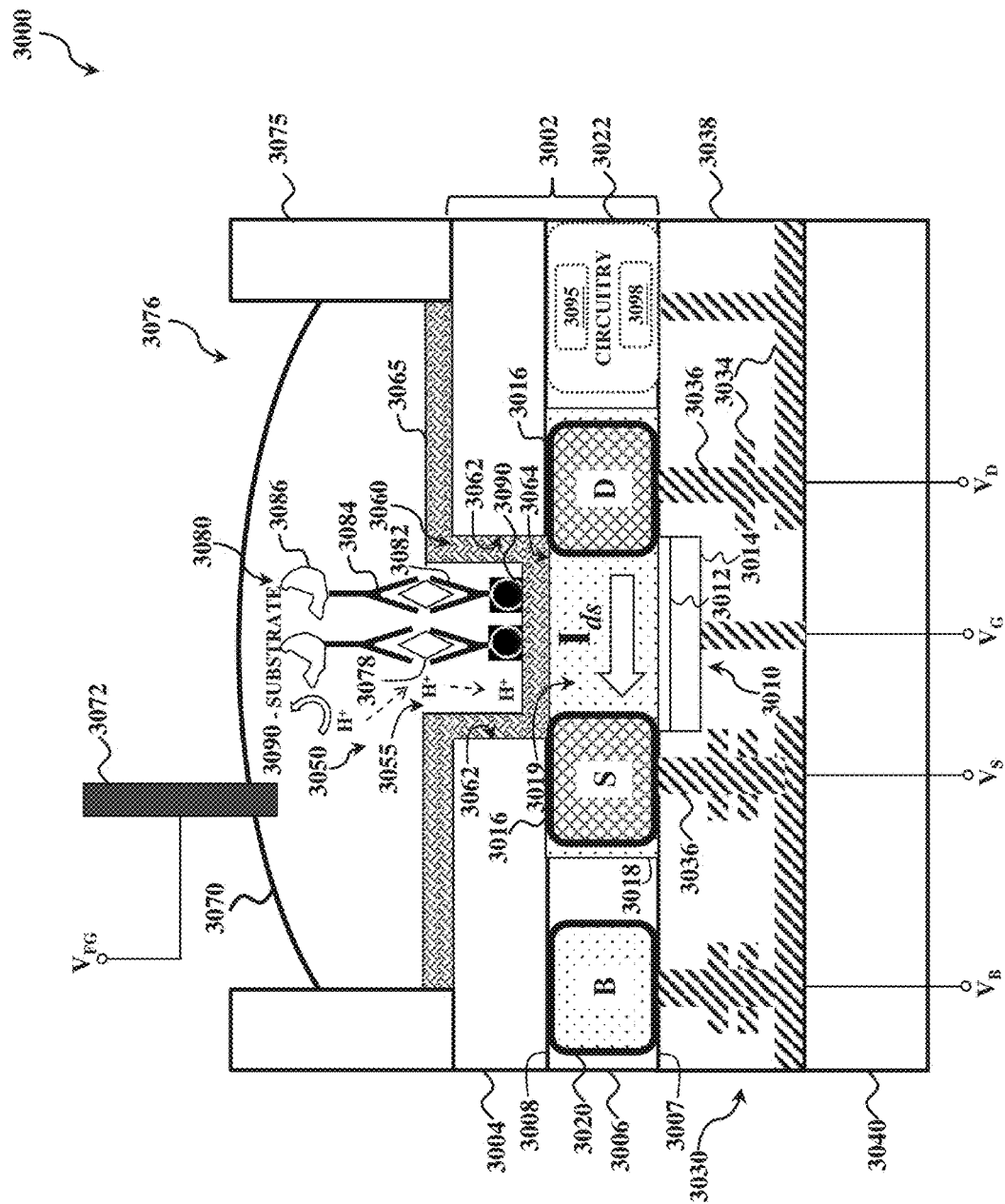
FIG. 31 is a fragmentary diagrammatic cross-sectional view of a dual-gate ion sensitive field effect transistor (ISFET) according to various aspects of the present disclosure.

Referring now to FIG. 31, FIG. 31 illustrates a dual-gate ion-sensitive field effect transistor (ISFET) 3000. Dual-gate ISFET 3000 is configured to measure ion concentrations in a solution. In some implementations, dual-gate ISFET 3000 is a portion of an integrated circuit (IC) chip or a system-on-chip (SoC). Dual-gate ISFET 3000 may be formed using suitable CMOS process technology, such as described herein. FIG. 31 has been simplified for the sake of clarity to better understand the inventive concepts of the present disclosure. Additional features can be added in dual-gate ISFET 3000, and some of the features described below can be replaced, modified, or eliminated in other embodiments of dual-gate ISFET 3000.

Dual-gate ISFET 3000 includes a device substrate 3002. In the depicted embodiment, device substrate 3002 includes an insulator layer 3004 and an active layer 3006. Insulator layer 3004 includes any suitable insulating material, such as silicon dioxide ($SiO_2$), and active layer 3006 includes any suitable semiconductor material, such as silicon. In some implementations, device substrate 3002 is similar to substrate 1902 described above. For example, device substrate 3002 is a silicon-on-insulator (SOI) substrate, where insulator layer 3004 is a buried oxide (BOX) layer of the SOI substrate and active layer 3006 is a silicon layer of the SOI substrate. Active layer 3006 includes a surface 3007 (which can be referred to as a front side surface) and a surface 3008 (which can be referred to as a backside surface).

A gate structure 3010 is disposed over device substrate 3002 (here, over a front side of device substrate 3002). Gate structure 3010, which includes a gate dielectric 3012 and a gate electrode 3014, is disposed between a source region (S) and a drain region (D), such as source/drain regions 3016. In the depicted embodiment, gate structure 3010 is disposed over surface 3007 of active layer 3006. For example, gate dielectric 3012 is disposed on active layer 3006, gate electrode 3014 is disposed on gate dielectric 3012, and source/drain regions 3016 are disposed in a doped well 3018 formed in active layer 3006. In some implementations, gate dielectric 3012 includes oxide, and gate electrode 3014 includes polysilicon, such that the transistor gate structure may be referred to as a polysilicon gate. Gate dielectric 3012 can alternatively or additionally include other suitable gate dielectric materials, such as high-k dielectric materials, oxide materials, nitride materials, oxynitride materials, and/or other suitable dielectric materials. Examples of high-k dielectric material include $HfO_2$, HfSiO, HfSiON, HfTaO, HfTiO, HfZrO, zirconium oxide, aluminum oxide, hafnium dioxide-alumina ($HfO_2$—$Al_2O_3$) alloy, other suitable high-k dielectric materials, or combinations thereof. Gate electrode 3014 can alternatively or additionally include other suitable gate electrode materials, such as a conductive material. Exemplary conductive materials include Al, Cu, Ti, Ta, W, Mo, TaN, NiSi, CoSi, TiN, WN, TiAl, TiAlN, TaCN, TaC, TaSiN, other conductive material, or combinations thereof. Gate structure 3014 may include numerous layers, for example, capping layers, interface layers, diffusion layers, barrier layers, conductive layers, hard mask layers, or combinations thereof. A portion of doped well 3018 disposed between source/drain regions 3016 forms a channel region 3019 (also referred to as an active region) of dual-gate ISFET 3000. Source/drain regions 3016 and doped well 3018 are doped regions formed in active layer 3006, for example, using an ion implantation process to implant dopants (for example, n-type dopants or p-type dopants) in active layer 3006. In some implementations, source/drain regions 3016 and doped well 3018 include opposite-type dopants. In FIG. 31, a doped well 3020 is also formed in active layer 3006, for example, by an ion implantation process. In some implementations, doped well 3020 is configured as a body region (B) of dual-gate ISFET 3000. In some implementations, doped well 3020 and doped well 3018 include same-type dopants.

Dual-gate ISFET 3000 further includes circuitry 3022, which can be disposed on, in, and/or over insulator layer 3004 and/or active layer 3006. Circuitry 3022 includes various passive and active microelectronic devices such as resistors, capacitors, inductors, diodes, metal-oxide semiconductor field effect transistors (MOSFET), complementary metal-oxide semiconductor (CMOS) transistors, high voltage transistors, high frequency transistors, other suitable components, or combinations thereof. In some implementations, circuitry 3022 includes CMOS circuitry configured to achieve desired operation of dual-gate ISFET 3000.

A multi-layer interconnect (MLI) structure 3030 is disposed over device substrate 3002. MLI 3030 electrically couples various components of dual-gate ISFET 3000, such that the various components are operable to function as specified by design requirements of dual-gate ISFET 3000. For example, MLI structure 3030 provides electrical connections to gate structure 3010 (for example, gate electrode 3014), source/drain regions 3016, doped well (body region) 3020, and circuitry 3022. In the depicted embodiment, MLI structure 3030 is disposed on surface 3007 of active layer 3006. MLI structure 3030 includes a combination of conductive layers and dielectric layers configured to form vertical interconnect features, such as contacts and/or vias, and/or horizontal interconnect features, such as lines. For example, in the depicted embodiment, MLI structure 3030 includes various conductive features (such as conductive lines 3034 and conductive vias (plugs) 3036) disposed in a dielectric layer 3038. Conductive lines 3034 and/or conductive vias 3036 include any suitable conductive material, such as metal. Metals include aluminum, aluminum alloy (such as aluminum/silicon/copper alloy), copper, copper alloy, titanium, titanium nitride, tantalum, tantalum nitride, tungsten, polysilicon, metal silicide, other suitable metals, or combinations thereof. Dielectric layer 3038 (also referred to as an inter-level dielectric (ILD) layer) includes a dielectric material, such as silicon oxide, silicon nitride, silicon oxynitride, TEOS formed oxide, phosphosilicate glass (PSG), borophosphosilicate glass (BPSG), low-k dielectric material, other suitable dielectric material, or combinations thereof. Exemplary low-k dielectric materials include fluorinated silica glass (FSG), carbon doped silicon oxide, Black Diamond® (Applied Materials of Santa Clara, Calif.), Xerogel, Aerogel, amorphous fluorinated carbon, Parylene, BCB (bis-benzocyclobutenes), SiLK (Dow Chemical, Midland, Mich.), polyimide, other proper materials, or combinations thereof.

A carrier (or handling) substrate 3040 is disposed over device substrate 3002. In the depicted embodiment, carrier substrate 3040 is attached (for example, bonded) to MLI structure 3030. In some implementations, carrier substrate 3040 is bonded to dielectric layer 3038. In some implementations, carrier substrate 3040 is bonded to a passivation layer disposed on MLI structure 3030 and/or dielectric layer 3038. Exemplary compositions for carrier substrate 3040 include silicon, glass, quartz, other suitable carrier substrate material, or combinations thereof. Carrier substrate 3040 can include various conductive features connected (for example, physically and/or electrically) to various components (for example, MLI structure 3030) of device substrate 3002. In some implementations, carrier substrate 3040 is similar to carrier substrate 2002. For example, carrier substrate 3040 can include an interconnect scheme (not shown) similar to interconnect scheme 2004 described above.

A fluidic gate structure 3050 (also referred to as a fluidic gate) is disposed over a backside of device substrate 3002. In the depicted embodiment, fluidic gate structure 3050 includes a sensing well 3055 disposed over surface 3008 of active layer 3006. Sensing well 3055 is substantially aligned with gate structure 3010 (here, gate dielectric 3012 and gate electrode 3014), such that sensing well 3055 is disposed over channel region 3019 of dual-gate ISFET 3000 between source/drain regions 3016. Sensing well 3055 is defined by an opening (trench) 3060 defined in insulating layer 3004 that exposes surface 3008 of active layer 3006. In the depicted embodiment, opening 3060 exposes channel region 3019 of dual-gate ISFET 3000, such that opening 3060 is substantially aligned with gate structure 3010. In some implementations, an isolation layer (such as isolation layer 2202 described above) is disposed on insulating layer 3004, and opening 3060 extends through both the isolation layer and insulating layer 3004 to expose channel region 3019 of dual-gate ISFET 3000. Opening 3060 includes sidewall portions 3062 (defined by exposed surface(s) of insulator layer 3004) extending from a bottom portion 3064 (defined by exposed surface(s) of active layer 3006).

Sensing well 3055 includes a sensing layer (membrane) 3065, which is disposed over the backside surface of device substrate 3002 to facilitate backside sensing of dual-gate ISFET 3000. Sensing layer 3065 is disposed on insulator layer 3004. In the depicted embodiment, sensing layer 3065 conforms to portions of device substrate 3002 that define opening 3060 (extending through insulator layer 3004), such that sensing layer 3065 is disposed on portions of insulator layer 3004 that define sidewall portions 3062 of opening 3060 and portions of active layer 3006 that define bottom portion 3064 of opening 3060. Sensing layer 3065 includes a material compatible with binding biomolecules and/or bio-entities. For example, sensing layer 3065 can provide a binding interface for biomolecules and/or bio-entities. Sensing layer 3065 may be similar to interface layers described herein, such as interface layer 1402 and/or interface layer 2402. In the depicted embodiment, sensing layer 3065 includes a high-k dielectric material, such as hafnium dioxide ($HfO_2$). The high-k dielectric material can increase gate capacitance, improving a signal-to-noise ratio of dual-gate ISFET 3000. In some embodiments, the high-k dielectric material facilitates higher gate oxide capacitance values (even for physically thicker gate oxides), reducing leakage current. In some embodiments, the high-k dielectric material exhibits smaller interface state densities, stabilizing electrostatic charging. Alternatively or additionally, sensing layer 3065 includes a dielectric material, a conductive material, and/or other suitable material for binding biomolecules and/or bio-entities, such as those described herein with reference to interface layer 1402 and/or interface layer 2402.

Sensing well 3055 further includes an electrolyte solution 3070, which can be biased by a reference electrode 3072 (including any suitable conductive material). Electrolyte solution 3070 includes any electrically conductive solution, such as a solution that contains ions, atoms, and/or molecules that have lost or gained electrons. In some implementations, to improve detection capabilities of dual-gate ISFET 3000, electrolyte solution 3070 is a low ion strength buffer solution configured to enhance analyte/antibody reactions. For example, electrolyte solution 3070 includes calcium chloride ($CaCl_2$), sodium chloride (NaCl), potassium chloride (KCl), magnesium chloride ($MgCl_2$), or combinations thereof. A fluidic channel 3075 can define an opening 3076 for confining electrolyte solution 3070 over sensing layer 3065. For example, in the depicted embodiment, electrolyte solution 3070 is disposed in opening 3076, such that electrolyte solution 3070 fills opening 3060 and contacts sensing layer 3065. Fluidic channel 3075 is disposed over device substrate 3002 (for example, on insulator layer 3004). In some implementations, fluidic channel 3075 is similar to fluidic channel 2602 described above. In some implementations, an isolation layer is disposed between fluidic channel 3075 and insulator layer 3004, such as isolation layer 2202 described above.

In operation, dual-gate ISFET 3000 generates an electrical signal that indicates a presence (or absence) of analytes (antigens) 3078 in a biological sample, which can be used for disease diagnostics. Analytes 3078 include glucose, urea, creatinine, influenza, or other desired molecule or desired substance for identification and/or measurement in a biological sample, such as a patient's blood sample, a patient's urine sample, or a serum containing a patient's specimen. Various biases can be applied to dual-gate ISFET 3000 to generate the electrical signal. For example, to achieve desired operation of dual-gate ISFET 3000, a gate voltage $V_G$ is applied to gate structure 3010 (for example, to gate electrode 3014 via MLI 3030), a fluidic gate voltage $V_{FG}$ is applied to fluidic gate structure 3050 (for example, to electrolyte solution 3070 via reference electrode 3072), a source voltage $V_S$ and/or a drain voltage $V_D$ is applied respectively to source/drain regions 3016 (for example, to a source electrode and/or a drain electrode via MLI 3030), and/or a body voltage $V_B$ is applied to body region 3020 (for example, to a body electrode via MLI 3030). In some implementations, for a given fluidic gate voltage $V_{FG}$ (and a given source voltage $V_S$/given drain voltage $V_D$), dual-gate ISFET 3000 generates a drain-to-source current $I_{ds}$ that is a function of a quantity of analytes 3078 present in the biological sample. For example, typically, antibodies are immobilized on sensing layer 3065 by antibodies (referred to as capture antibodies). Since analytes 3078 are typically charged, an electrical potential on sensing layer 3065 changes as analytes 3078 bind with the capture antibodies, causing a change in conductance in channel region 3019 of dual-gate ISFET 3000, and a corresponding change in drain-to-source current $I_{ds}$. A biological sample with a higher concentration of analytes 3078 will bind more analytes 3078, causing a greater change in drain-to-source current $I_{ds}$, such that drain-to-source current $I_{ds}$ increases as a quantity of analytes 3078 increases in the biological sample. Drain-to-source current $I_{ds}$ generated by dual-gate ISFET 3000 is thus correlated to a quantity of analytes 3078 in the biological sample.

In some implementations, drain-to-source current $I_{ds}$ is evaluated at a threshold voltage $V_{TH}$ of dual-gate ISFET 3000 to determine presence (or absence) of analytes 3078 (for example, when fluidic gate voltage $V_{FG}$ is approximately equal to threshold voltage $V_{TH}$ of dual-gate ISFET 3000. FIG. 31 depicts different current-voltage (I-V) curves generated by dual-gate ISFET 3000 depending on an ion concentration in electrolyte solution 3070, which indicates a quantity of analytes 3078 present in the biological sample. I-V curve A, I-V curve B, I-V curve C, and I-V curve D each model drain-to-source current $I_{DS}$ as a function of fluidic gate voltage $V_{FG}$. In the depicted embodiment, drain-to-source current $I_{DS}$ is evaluated when fluidic gate voltage $V_{FG}$ reaches a threshold voltage ($V_{TH}$). For example, when fluidic gate voltage $V_{FG}$ reaches a first threshold voltage ($V_{TH1}$), a second threshold voltage ($V_{TH2}$), a third threshold voltage ($V_{TH3}$), and a fourth threshold voltage ($V_{TH4}$), ion concentration in electrolyte solution 3070 is determined in a picogram/milliliter (pg/ml) range, nanogram/milliliter (ng/ml) range, microgram/milliliter (ug/ml) range, and milligram/milliliter (mg/ml) range, respectively. Accordingly, increases in threshold voltage $V_{TH}$ of fluidic gate structure 3050 correspond with increases in ion concentration in electrolyte solution 3070. In some implementations, gate structure 3010 is grounded, such that gate structure 3010 is turned off and dual-gate ISFET 3000 uses fluidic gate structure 3050 for sensing. In some implementations, gate structure 3010 is turned on, for example, to control an electron distribution in channel region 3019 of dual-gate ISFET 3000 without bulk substrate effects. In some implementations, fluidic gate structure 3050 is grounded, such that fluidic gate structure 3050 is turned off and dual-gate ISFET 3000 uses gate structure 3010 for sensing. In some implementations, both fluidic gate structure 3050 and gate structure 3010 are biased for sensing operations of dual-gate ISFET 3000.

Often, drain-to-source current $I_{ds}$ generated from analytes 3078 binding to the capture antibodies is not detectable or insufficiently strong for quantification purposes. In the depicted embodiment, an enzyme-modified detection mechanism 3080 is thus implemented to enhance sensitivity of dual-gate ISFET 3000, improving detection and/or quantification of analytes 3078 by dual-gate ISFET 3000. For example, upon detecting analytes 3078, enzyme-modified detection mechanism 3080 generates ions (via enzymatic reactions) that react with sensing layer 3065, amplifying electrical potential changes on sensing layer 3065 compared to electrical potential changes caused by analytes 3078 binding with the capture antibodies alone and allowing dual-gate ISFET 3000 to generate detectable levels of drain-to-source current $I_{ds}$ for quantifying and measuring analytes 3078 in a biological sample. As analytes 3078 increase in the biological sample, analytes 3078 captured by enzyme-modified detection mechanisms 3080 increases, thereby increasing enzymatic reactions from enzyme-modified detection mechanisms 3080, increasing interactions between ions and sensing layer 3065, and increasing drain-to-source current $I_{ds}$ generated by dual-gate ISFET 3000. As analytes 3078 decrease in the biological sample, analytes 3078 captured by enzyme-modified detection mechanisms 3080 decreases, thereby decreasing enzymatic reactions from enzyme-modified detection mechanisms 3080, decreasing interactions between ions and sensing layer 3065, and decreasing drain-to-source current $I_{ds}$ generated by dual-gate ISFET 3000. Enzyme-modified detection mechanism 3080 thus amplifies drain-to-source current $I_{ds}$ generated by dual-gate ISFET 3000, improving detectability and quantification of analytes 3078 in the biological sample and facilitating real-time disease detection and diagnosis.

Enzyme-modified detection mechanism 3080 includes a capture antibody 3082 and an enzyme-labeled detection antibody (for example, a detection antibody 3084 conjugated with an enzyme 3086). Capture antibody 3082 and detection antibody 3084 have specificity for a particular analyte, such as analyte 3078. Capture antibody 3082 binds (captures) analyte 3078, for example, when fluidic gate structure 3050 is exposed to a biological sample. The biological sample can be provided in solution form in fluidic channel 3075, such that the biological sample fills opening 3060 (thus contacting a surface of sensing layer 3065). Detection antibody 3084 binds with any analyte 3078 bound to capture antibody 3082. In some implementations, detection antibody 3084 is added to electrolyte solution 3070. Enzyme 3086 includes any suitable biological catalyst. For example, enzyme 3086 includes glucose oxidase (GOO, alkaline phosphatase (ALP), or horseradish peroxidase (HRP). An enzyme substrate (reactant) 3090 reacts with enzyme 3086 to generate a product (here, protons (for example, H+ ions)) that reacts with sensing layer 3065. As the product reacts with sensing layer 3065 (for example, sensing layer 3065 adsorbs ions from electrolyte solution 3070, such as the ions generated by enzyme-modified detection mechanism 3080), an electrical potential of sensing layer 3065 changes, thereby altering a potential of fluidic gate structure 3050 (and/or gate structure 3010) and causing dual-gate ISFET 3000 to generate drain-to-source current $I_{ds}$ to a degree that depends on a quantity of product interacting with sensing layer 3065 (which depends on a quantity of analytes 3078 detected by enzyme-modified detection mechanisms 3080). In some implementations, enzyme substrate 3090 is added to electrolyte solution 3070.

Capture antibody 3082 is immobilized on a surface of sensing layer 3065. In the depicted embodiment, a linker 3090 binds capture antibody 3082 to sensing layer 3065. Linker 3090 includes any material that can achieve binding with sensing layer 3065 and capture antibody 3082. For example, linker 3090 can be a bi-functional linker, which includes at least one functional group that reacts with sensing layer 3065 and at least one functional group that reacts with capture antibody 3082. In some implementations, linker 3090 is a silane linker (for example, including a silane linker molecule). In some implementations, linker 3090 is a 3-aminopropyltriethoxysilane (APTS) linker (for example, including an APTS molecule). In some implementations, the at least one functional group for reacting with capture antibody 3082 is an amine functional group. Alternatively, in some implementations, capture antibody 3082 directly binds to sensing layer 3065, eliminating a need for linker 3090. Alternatively, in some implementations, enzyme 3086 is immobilized on the surface of sensing layer 3065, eliminating a need for capture antibody 3082 and detection antibody 3084.

To further enhance detection capabilities, dual-gate ISFET 3000 includes a temperature sensor 3095 and/or a heater 3098. Temperature sensor 3095 detects a temperature of device substrate 3002, and heater 3098 heats device substrate 3002. For example, temperature sensor 3095 measures a temperature of active layer 3006, and heater 3098 heats active layer 3006, for example, until active layer 3006 reaches a temperature (for example, as measured by temperature sensor 3095) that optimizes enzymatic reactions (for example, producing products for reacting with sensing layer 3065) and/or substrate reactions (for example, enhancing reactions between products with sensing layer 3065). In some implementations, temperature sensor 3530 and/or heater 3540 maintain device substrate 3002 at a temperature that shortens enzymatic reaction time, facilitating early disease detection and/or diagnosis.

Figure 32:
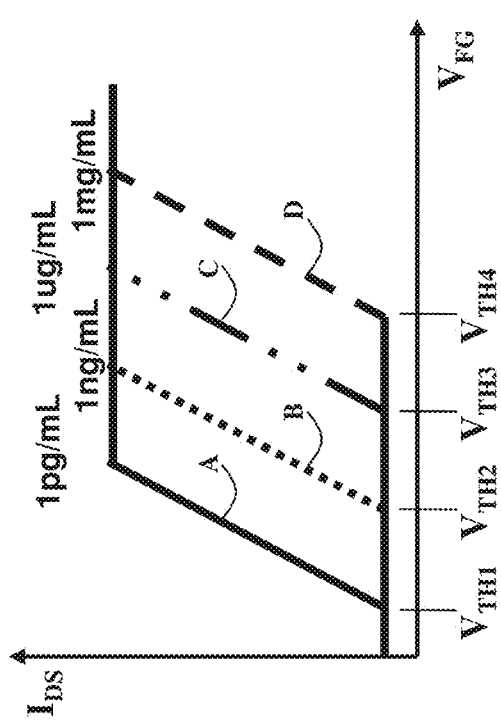
FIG. 32 illustrates different current-voltage curves generated by a dual-gate ISFET, such as dual-gate ISFET of FIG. 31, according to various aspects of the present disclosure.
Figure 33:
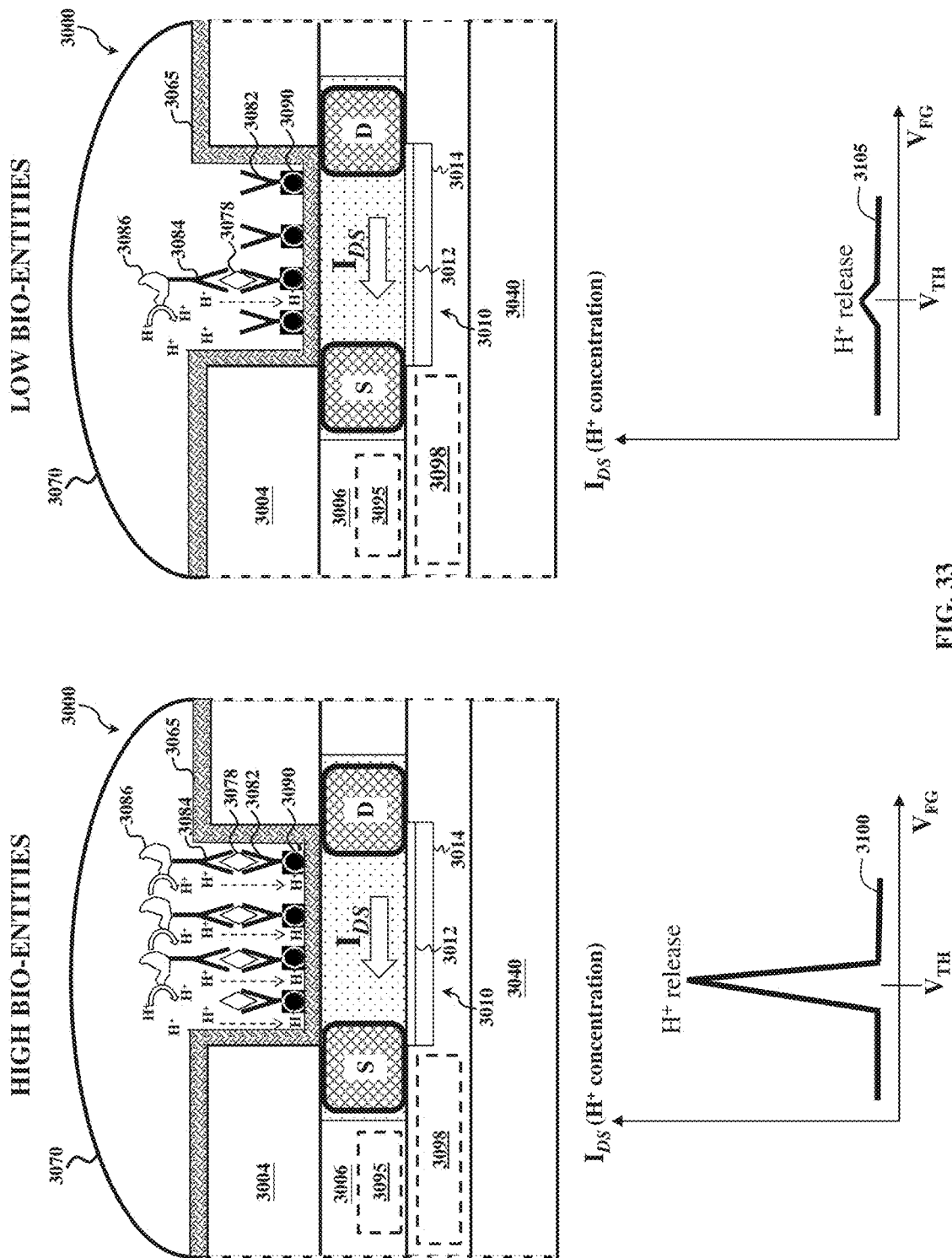
FIGS. 33-35 illustrate disease diagnostics achieved using a dual-gate ISFET, such as the dual-gate ISFET of FIG. 31, according to various aspects of the present disclosure.
Figure 34:
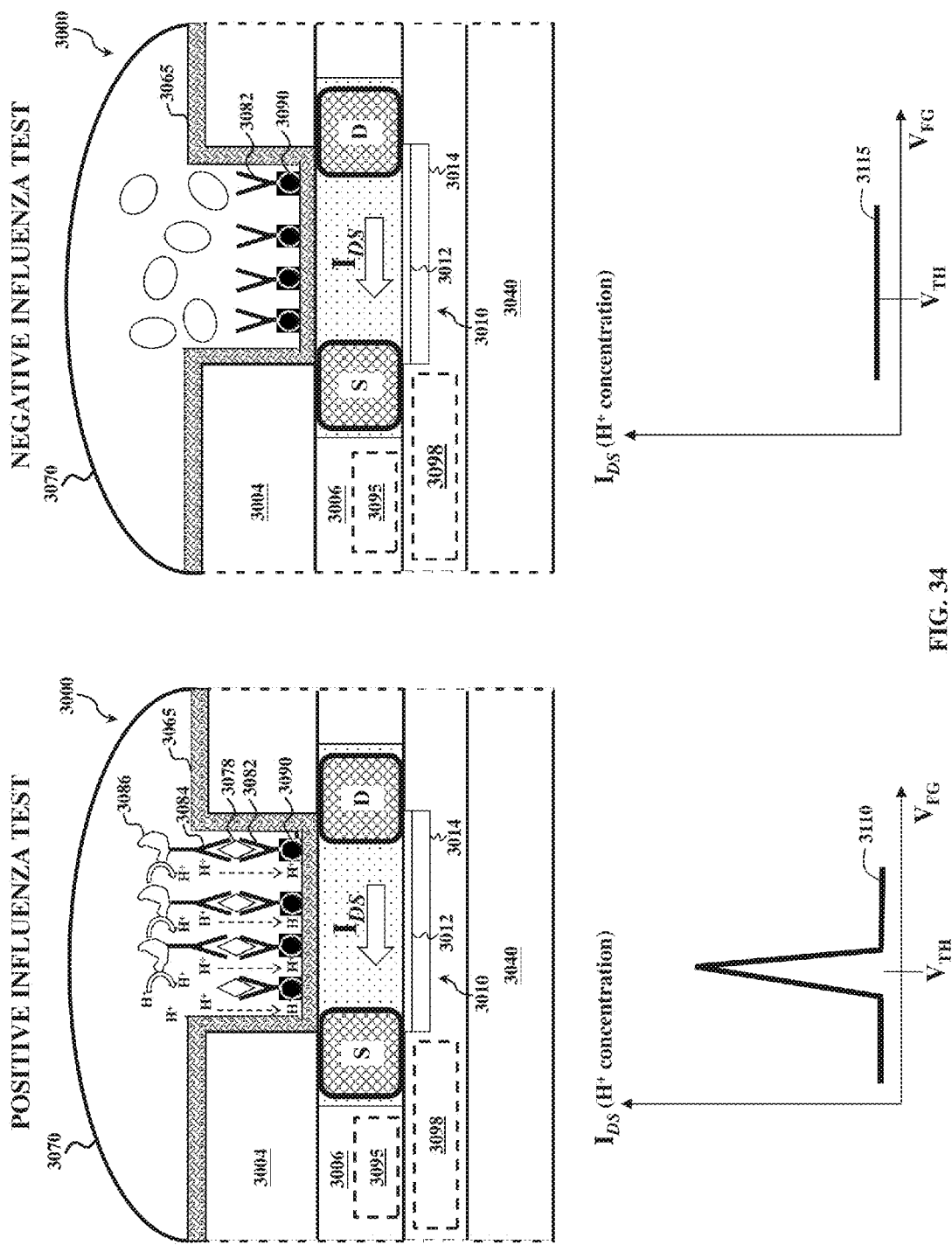
Figure 35:
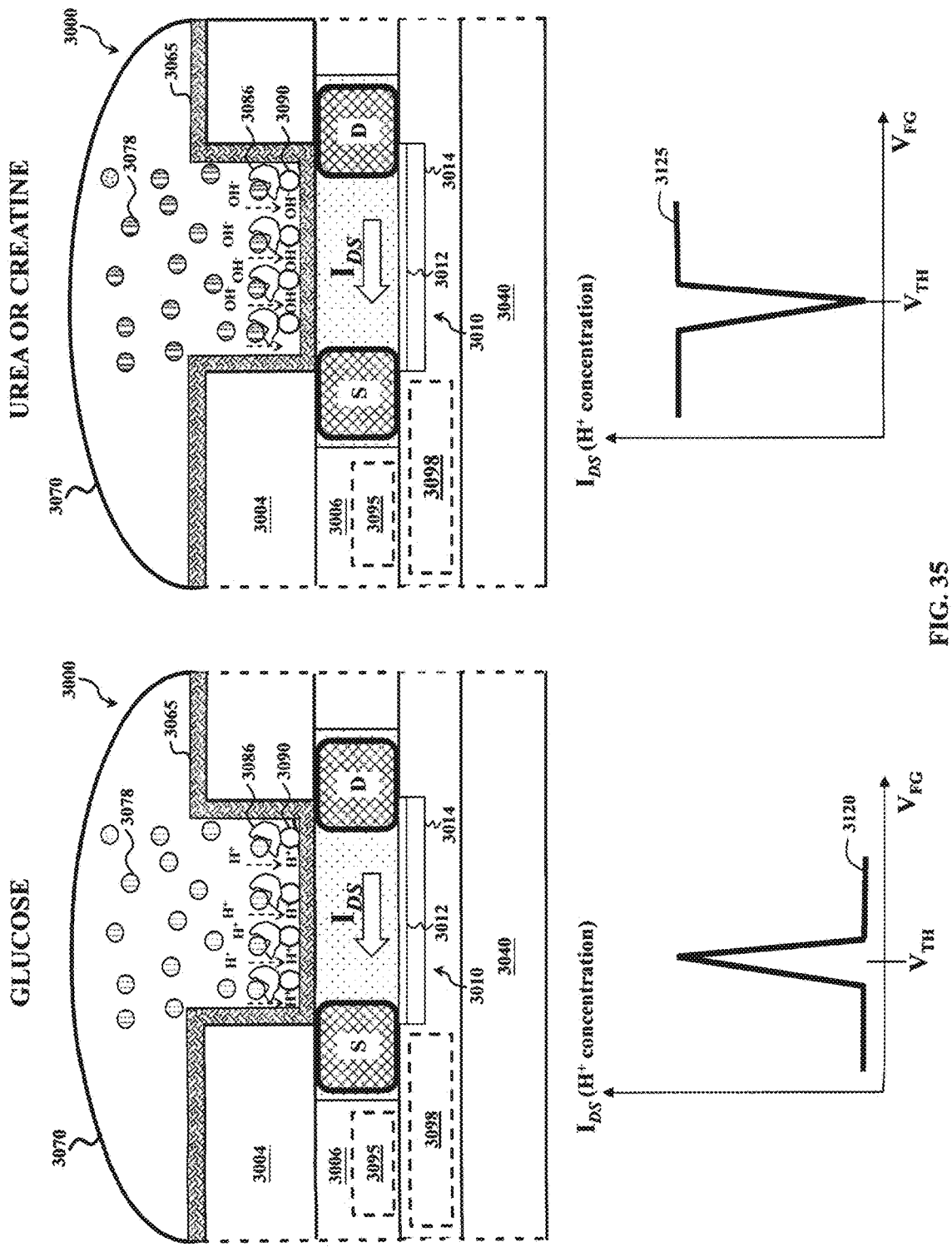

Referring now to FIGS. 33-35, dual-gate ISFET 3000 can be implemented for enzyme-linked immunosorbent assay (ELISA), which generally refers to an immunological assay for measuring bio-entities in a biological sample. ELISA can include various steps for detection and quantification of the bio-entities. For example, capture antibodies 3082 are immobilized on sensing layer 3065 (in particular, on sensing layer 3065 in sensing well 3055), for example, via linker 3090. In some implementations, capture antibodies 3082 are provided in solution form in fluidic channel 3075, such that the solution fills opening 3060 (thus contacting a surface of sensing layer 3065) and capture antibodies 3082 bind with sensing layer 3065 and/or linker 3090. Any excess capture antibodies 3082 that do not bind with sensing layer 3065 and/or linker 3090 can be removed by an appropriate washing process. In some implementations, a blocker is provided in solution form in fluidic channel 3075, such that the solution fills opening 3060 (thus contacting a surface of sensing layer 3065) and the blocker binds with any unbound sites of sensing layer 3065 and/or unbound linker 3090. Then, a biological sample is provided in solution form in fluidic channel 3075. The biological sample fills opening 3060 (thus contacting a surface of sensing layer 3065) and any analytes 3078 from biological sample bind to capture antibodies 3082. Any excess analytes 3078 that do not bind with capture antibodies 3082 can be removed by an appropriate washing process. Subsequently, enzyme-labeled detection antibodies (for example, detection antibodies 3084 conjugated with enzymes 3086) are added to sensing well 3055. For example, a solution that includes enzyme-labeled detection antibodies is provided in fluidic channel 3075, such that the solution fills opening 3060 (thus contacting a surface of sensing layer 3065) and detection antibodies 3084 bind to any analytes 3078 bound to capture antibodies 3082. Any enzyme-labeled detection antibodies that do not bind with analytes 3078 can be removed by an appropriate washing process. Enzyme substrate 3090 is then added to sensing well 3055. For example, enzyme substrate 3090 is introduced into enzyme solution 3070. Enzyme substrate 3090 reacts with enzymes 3086 (of the enzyme-labeled detection antibodies). In some implementations, enzyme substrate 3090 binds with active sites of enzymes 3086, generating ions, such as hydrogen ions (H+) or hydroxyl ions (OH−), that can be detected by dual-gate ISFET 3000. As described herein, protons (such as hydrogen ions (H+)) react with sensing layer 3065, generating a detectable drain-to-source current $I_{DS}$. During ELISA, various incubation periods may be implemented for each solution added to fluidic channel 3065 to ensure sufficient time for binding. In the various embodiments depicted in FIGS. 32-34, temperature sensor 3095 and/or a heater 3098 are used to control a temperature of device substrate 3002, improving efficiency of enzymatic reactions associated with enzyme-modified detection mechanisms 3080 (for example, by shortening enzymatic reaction time).

In FIG. 33, dual-gate ISFET 3000 can be implemented for quantifying healthcare and/or disease conditions. For example, dual-gate ISFET 3000 generates different current-voltage (I-V) curves, an I-V curve 3100 and an I-V curve 3105, depending on a quantity of analytes 3078 present in the biological sample. I-V curve 3100 and I-V curve 3105 model a drain-to-source current $I_{DS}$ (which correlates with a concentration of ions (here, protons (H+)) in electrolyte solution 3070) as a function of a fluidic gate voltage $V_{FG}$. In the depicted embodiment, drain-to-source current $I_{DS}$ is evaluated when fluidic gate voltage $V_{FG}$ reaches a threshold voltage ($V_{TH}$). Drain-to-source current $I_{DS}$ is greater when the biological sample includes a high number of bio-entities (in other words, enzyme-modified detection mechanisms 3080 detect a high number of analytes 3078), compared to when the biological sample includes a low number of bio-entities (in other words, enzyme-modified detection mechanisms 3080 detect a low number of analytes 3078). Accordingly, dual-gate ISFET 3000 can be implemented for quantifying bio-entities in the biological sample, which correlates with drain-to-source current $I_{DS}$ generated by dual-gate ISFET 3000 upon detecting ions generated from enzyme-modified detection mechanisms 3080.

Referring now to FIG. 34, dual-gate ISFET 3000 can be implemented for identifying diseases and/or allergens in a biological sample, such as influenza, cancer, cardiovascular disease, allergies, or other disease. For example, dual-gate ISFET 3000 generates different current-voltage (I-V) curves, an I-V curve 3110 and an I-V curve 3115, when analytes 3078 are present in the biological sample. In some implementations, analytes 3078 represent an influenza A, an influenza B, or an influenza C virus. For example, I-V curve 3110 and I-V curve 3115 model a drain-to-source current $I_{DS}$ (which correlates with a concentration of ions (here, protons (H+)) in electrolyte solution 3070) as a function of a fluidic gate voltage $V_{FG}$. In the depicted embodiment, drain-to-source current $I_{DS}$ is evaluated when fluidic gate voltage $V_{FG}$ reaches a threshold voltage ($V_{TH}$). In FIG. 33, dual-gate ISFET 3000 generates a drain-to-source current $I_{DS}$ when the biological sample includes influenza-specific analytes, such as analytes 3078, resulting in a positive test for influenza. In contrast, dual-gate ISFET 3000 generates minimal (or no) drain-to-source current $I_{DS}$ when influenza-specific analytes, such as analytes 3078, are absent from the biological, resulting in a negative test for influenza. Accordingly, dual-gate ISFET 3000 can be implemented for identifying a disease in the biological sample, which correlates with drain-to-source current $I_{DS}$ generated by dual-gate ISFET 3000 upon detecting ions generated from enzyme-modified detection mechanisms 3080.

Referring now to FIG. 35, dual-gate ISFET 3000 is implemented for identifying and/or quantifying glucose, urea, or creatinine in a biological sample. In the depicted embodiment, dual-gate ISFET 3000 is modified, such that enzymes 3086 are immobilized on linkers 3090, eliminating a need for capture antibodies 3082 and detection antibodies 3084. Dual-gate ISFET 3000 generates different current-voltage (I-V) curves, an I-V curve 3120 and an I-V curve 3125, depending on whether a biological sample includes glucose, urea, or creatinine. I-V curve 3120 and I-V curve 3125 model a drain-to-source current $I_{DS}$ (which correlates with a concentration of hydrogen ions (H+) or hydroxyl ions (OH−), respectively, in electrolyte solution 3070) as a function of a fluidic gate voltage $V_{FG}$. When the biological sample includes glucose, enzymes 3086 generate hydrogen ions (H+) that react with sensing layer 3065 upon detecting analytes 3078, such that a drain-to-source current $I_{DS}$ increases. In contrast, when the sample includes urea or creatinine, enzymes 3086 generate hydroxyl ions (OH−) that react with sensing layer 3065 upon detecting analytes 3078, such that a drain-to-source current $I_{DS}$ decreases. Accordingly, dual-gate ISFET 3000 can be implemented for identifying a presence and/or a quantity of glucose (facilitating blood glucose monitoring) or urea/creatinine (facilitating liver and/or kidney monitoring) in the biological sample, which correlates with drain-to-source current $I_{DS}$ generated by dual-gate ISFET 3000 upon detecting ions generated from enzyme-modified detection mechanisms 3080.

Figure 36:
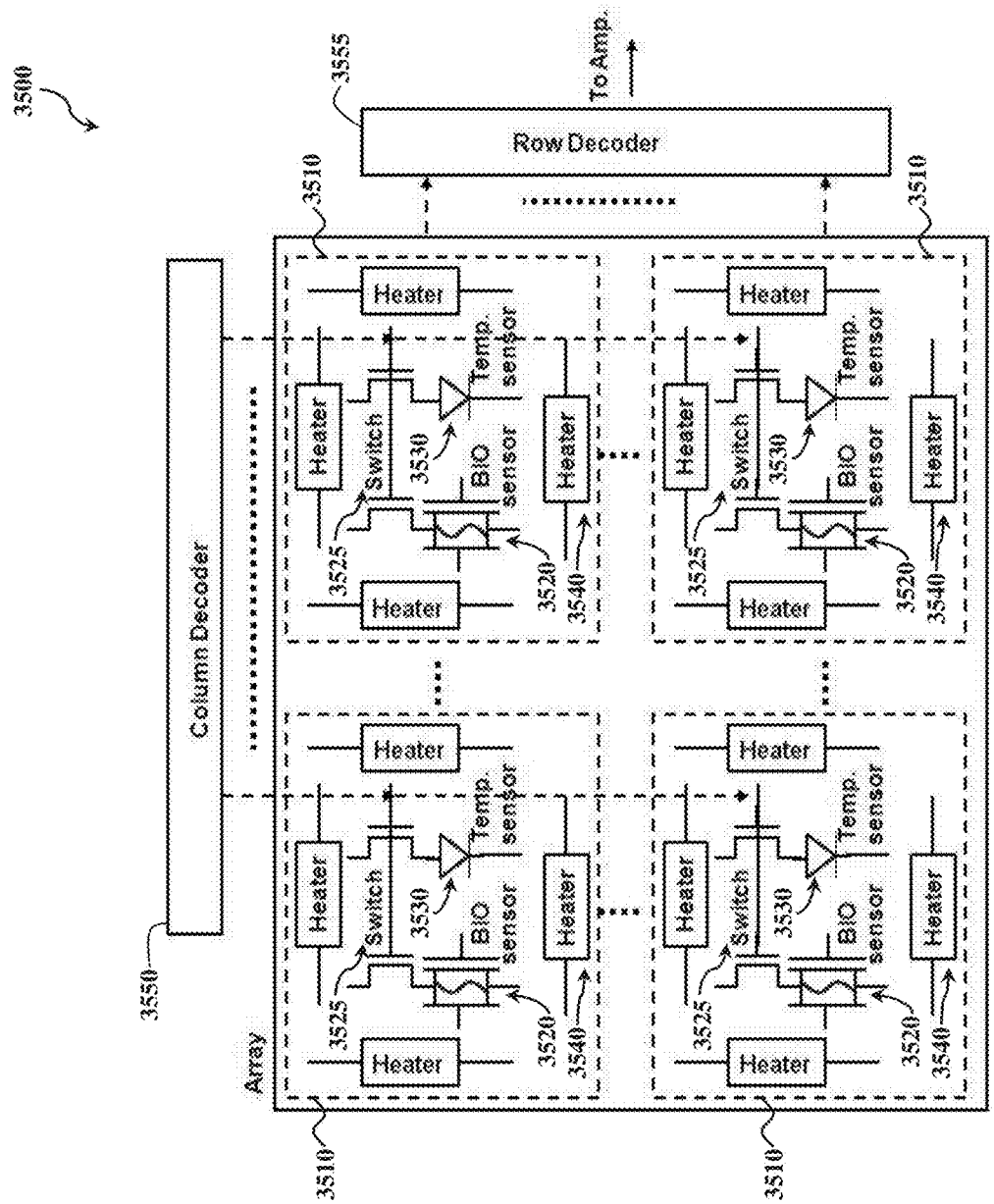
FIG. 36 is a fragmentary diagrammatic top view of a sensor array, which can implement the dual-gate ISFET of FIG. 31, according to various aspects of the present disclosure.

Referring now to FIG. 36, FIG. 36 depicts an exemplary diagram of a sensor array 3500, such as an integrated biological sensor array. Sensor array 3500 includes a plurality of sensors 3510 arranged in rows and columns. Each sensor 3510 includes a dual-gate ion-sensitive field effect transistor (ISFET) 3520 (also referred to as a biological sensor and/or a biosensor), a switch 3525, a temperature sensor 3530, and a heater 3540. In some implementations, dual-gate ISFET 3530 is similar to dual-gate ISFET 3000 described above. For example, dual-gate ISFET 3530 is configured to generate an electrical signal that indicates an ion concentration in an electrolyte solution (such as electrolyte solution 3070), which correlates with a presence and/or a quantity of target analytes (such as analytes 3078) in a biological sample. Sensor array 3500 further includes a column decoder 3550 and a row decoder 3555 for selectively powering sensors 3510 (in other words, selectively turning on and off). For example, column decoder 3550 and row decoder 3555 can generate, respectively, a column selection signal and a row selection signal that electrically turns on switch 3525 for a particular sensor 3510, enabling the particular sensor 3510 to output an electrical signal correlated with a concentration of ions detected by dual-gate ISFET 3520 of the particular sensor 3510. In some implementations, the sensor array 3500 individually biases the fluidic gate structures and the gate structures of dual-gate ISFETs 3520 to generate an electrical signal when the sensing layers react with ions generated from enzyme-modified detection mechanisms. The electrical signal indicates an ion concentration in the electrolyte solutions that correlates with a presence or a quantity of target analytes in the biological sample. In some implementations, the gate structures of dual-gate ISFETs 3520 are individually biased to compensate for operational characteristics of dual-gate ISFETs 3520. In some implementations, the electrical signal is received by other circuitry (such as CMOS circuitry 3022), which can amplify the electrical signal for identification and quantification of target analytes in a biological sample. Temperature sensor 3530 and/or a heater 3540 are used to improve sensitivity of dual-gate ISFET 3520. For example, temperature sensor 3530 and/or heater 3540 control a temperature of the device substrate of dual-gate ISFET 3520 (for example, device substrate 3002) to optimize generation of enzymatic reactions from enzyme-modified detection mechanisms. FIG. 36 has been simplified for the sake of clarity to better understand the inventive concepts of the present disclosure, Additional features can be added in sensor array 3500, and some of the features described below can be replaced, modified, or eliminated in other embodiments of sensor array 3500.

Figure 37:
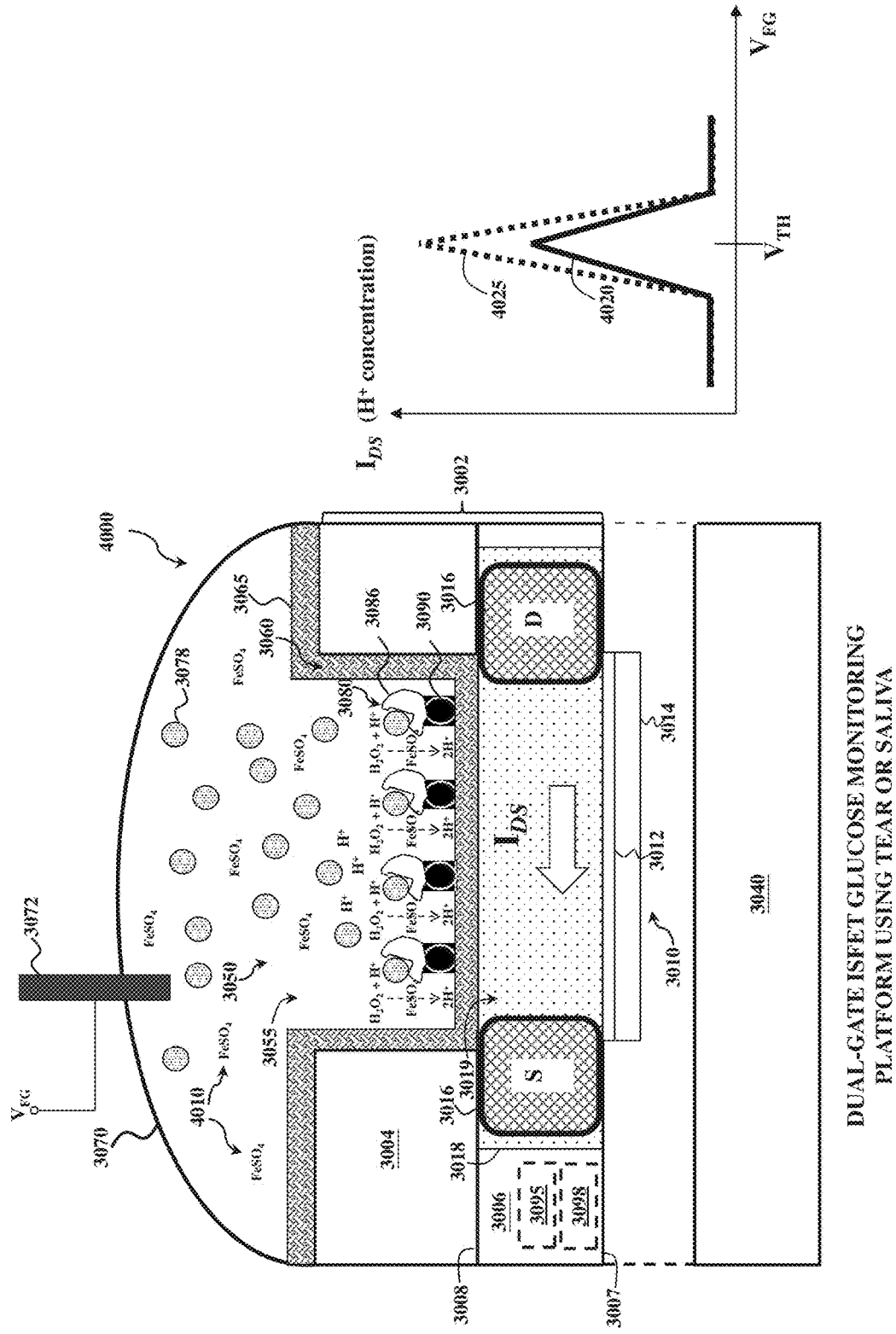
FIG. 37 is a fragmentary diagrammatic cross-sectional view of a dual-gate ISFET for a glucose monitoring platform according to various aspects of the present disclosure.

To further enhance detection capabilities of dual-gate ISFETs, such as dual-gate ISFET 3000, the present disclosure further proposes implementing electrolyte solutions that include constituents that can react with products generated from the enzymatic reactions that occur when enzyme-modified detection mechanisms detect analytes. Constituents are chosen based on the products generated from the enzymatic reactions, such that a reaction between a constituent included in the electrolyte solution and a product generated from an enzymatic reaction releases an additional ion that can react with the sensing layer, thereby further amplifying electric potential changes on the sensing layer when enzyme-modified detection mechanisms detect analytes in a biological sample. Referring now to FIG. 37, a dual-gate ISFET 4000 is implemented for identifying and/or quantifying glucose in a biological sample, such as a patient's blood sample, a patient's urine sample, or a serum containing a patient's specimen. In some implementations, dual-gate ISFET 4000 analyzes a patient's saliva and/or a patient's tears for glucose using the signal enhancement mechanisms described herein. Dual-gate ISFET 4000 is similar in many respects to dual-gate ISFET 3000. For example, dual-gate ISFET 4000 quantifies glucose levels by measuring ion concentrations in a solution. Accordingly, similar features in FIGS. 31-36 and FIG. 37 are identified by the same reference numerals for clarity and simplicity. In some implementations, dual-gate ISFET 4000 is a portion of an IC chip or an SoC. Dual-gate ISFET 4000 may be formed using suitable CMOS process technology, such as described herein. FIG. 37 has been simplified for the sake of clarity to better understand the inventive concepts of the present disclosure. Additional features can be added in dual-gate ISFET 4000, and some of the features described below can be replaced, modified, or eliminated in other embodiments of dual-gate ISFET 4000.

Similar to dual-gate ISFET 3000, dual-gate ISFET 4000 includes gate structure 3010 (including gate dielectric 3012 and gate electrode 3014) disposed over the front side of device substrate 3002 (for example, over surface 3007 of active layer 3006) and fluidic gate structure 3050 disposed over the backside of device substrate (for example, over surface 3008 of active layer 3006). Fluidic gate structure 3050 includes sensing well 3055 substantially aligned with gate structure 3010, where sensing well 3055 includes sensing layer 3065 (conforming to opening 3060 defined in insulator layer 3004 of device substrate 3002) and electrolyte solution 3070, which is confined in opening 3076 (and opening 3060) by fluidic channel 3075 (not depicted in FIG. 37). Though not depicted, dual-gate ISFET 4000 further includes MLI 3030 (having conductive lines 3034, conductive vias 3036, and dielectric layer 3038) disposed between substrate 3002 and carrier substrate 3040, where MLI structure 3030 provides electrical connections to gate structure 3010, source/drain regions 3016, circuitry 3022 (also not depicted in FIG. 37), and/or doped well 3020 (also not depicted in FIG. 37).

Dual-gate ISFET 4000 also implements enzyme-modified detection mechanism 3080 for enhancing sensitivity, improving detection and/or quantification of analytes 3078 (here, glucose) by dual-gate ISFET 4000. In contrast to dual-gate ISFET 3000, capture antibodies 3082 and detection antibodies 3084 are eliminated from enzyme-modified detection mechanism 3080 by immobilizing enzyme 3086 on sensing layer 3065 (for example, via linkers 3090). Upon detecting analytes 3078, enzyme-modified detection mechanism 3080 generates ions (via enzymatic reactions) that react with sensing layer 3065, amplifying electrical potential changes on sensing layer 3065 compared to electrical potential changes caused by analytes 3078 binding with antibodies alone and allowing dual-gate ISFET 4000 to generate detectable levels of drain-to-source current $I_{ds}$ for quantifying and measuring analytes 3078 in the biological sample. In some implementations, when a biological sample is provided in solution form in fluidic channel 3075, such that the biological sample fills opening 3060 (and thus contacts a surface of sensing layer 3065), analyte 3078 can bind (or react) with enzyme 3086, generating one or more products. As described in detail below, an enzymatic reaction that occurs when enzyme-modified detection mechanism 3080 detects analyte 3078 releases an ion (for example, an H+ ions) that reacts with sensing layer 3065. As analytes 3078 increase in the biological sample, analytes 3078 captured (or sensed) by enzyme-modified detection mechanisms 3080 increases, thereby increasing enzymatic reactions from enzyme-modified detection mechanisms 3080, increasing interactions between ions (here, H+ ions) and sensing layer 3065, and increasing drain-to-source current $I_{ds}$ generated by dual-gate ISFET 4000. As analytes 3078 decrease in the biological sample, analytes 3078 captured (or sensed) by enzyme-modified detection mechanisms 3080 decreases, thereby decreasing enzymatic reactions from enzyme-modified detection mechanisms 3080, decreasing interactions between ions and sensing layer 3065, and decreasing drain-to-source current $I_{ds}$ generated by dual-gate ISFET 4000. Enzyme-modified detection mechanism 3080 thus amplifies drain-to-source current $I_{ds}$ generated by dual-gate ISFET 4000, improving detectability and quantification of analytes 3078 in the biological sample and facilitating real-time disease detection and diagnosis.

Dual-gate ISFET 4000 further enhances signal strength and increases detection limits by incorporating constituents in electrolyte solution 3070 that can react with products from the enzymatic reaction of analyte 3078 and enzyme-modified detection mechanism 3080 (in particular, enzyme 3086), thereby generating additional ions for reacting with sensing layer 3065. For example, in implementations where enzyme 3086 includes glucose oxidase enzyme ($GO_x$), the enzymatic reaction involves enzyme 3086 oxidizing analyte 3078 according to the following chemical equation:

The enzymatic reaction thus converts glucose (analyte 3078) into gluconic acid and oxygen into hydrogen peroxide ($H_2O_2$). Dual-gate ISFET 4000 can use the products of the enzymatic reaction, such as hydrogen peroxide, to generate additional ions that can react with sensing layer 3065. For example, in the depicted embodiment, electrolyte solution 3070 includes iron-containing constituents 4010 that react with hydrogen peroxide to generate additional ions (for example, H+ ions) that react with sensing layer 3065. In the depicted embodiment, iron-containing constituents include ferrous sulfate ($FeSO_4$), such that dual-gate ISFET 4000 benefits from Fenton's reactions between ferrous sulfate and hydrogen peroxide. According to Fenton's reaction, a reaction between ferrous sulfate and hydrogen peroxide releases an ion (for example, an H+ ion) according to the following chemical equation:

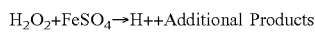

The ion reacts with sensing layer 3065 to further amplify electrical potential changes on sensing layer 3065 compared to electrical potential changes caused by the enzymatic reaction alone, allowing dual-gate ISFET 4000 to significantly enhance detectability of drain-to-source current $I_{ds}$ for quantifying and measuring analytes 3078. By including constituents in electrolyte solution 3070 that can react with products of the enzymatic reactions, dual-gate ISFET 4000 includes at least two sources for enhancing its electrical signal: a first ion generated from an enzymatic reaction that occurs when enzyme-modified detection mechanism 3080 detects analyte 3078, and a second ion generated when a constituent of electrolyte solution 3070 reacts with a product of the enzymatic reaction. Such is depicted in FIG. 37 as two protons (for example, 2H+). In some implementations, constituents in electrolyte solution 3070 that react with products of the enzymatic reactions to produce additional ions effectively increase signal strength of dual-gate ISFET 4000 by as much as 100% compared to other dual-gate ISFETs, such as dual-gate ISFET 3000. In some implementations, where electrolyte solution 3070 includes iron-containing constituents (such as ferrous sulfate), dual-gate ISFET 4000 can use any enzyme-modified detection mechanism 3080 that generates hydrogen peroxide via an enzymatic reaction upon detecting analyte 3078. In the various implementations, temperature sensor 3095 and/or a heater 3098 are used to control a temperature of device substrate 3002, improving efficiency of enzymatic reactions associated with enzyme-modified detection mechanisms 3080 and/or reactions between products of the enzymatic reactions and constituents of electrolyte solution 3070 (for example, by shortening enzymatic reaction time and/or other reaction time required for generating the ions and/or detectable levels of drain-to-source current).

In operation, dual-gate ISFET 4000 generates an electrical signal that indicates a presence (or absence) of analytes 3078 in a biological sample, which can be used for disease diagnostics. Similar to dual-gate ISFET 3000, various biases can be applied to dual-gate ISFET 4000 to generate the electrical signal. For example, to achieve desired operation of dual-gate ISFET 4000, a gate voltage $V_G$ is applied to gate structure 3010 (for example, to gate electrode 3014 via MLI 3030), a fluidic gate voltage $V_{FG}$ is applied to fluidic gate structure 3050 (for example, to electrolyte solution 3070 via reference electrode 3072), a source voltage $V_S$ and/or a drain voltage $V_D$ is applied respectively to source/drain regions 3016 (for example, to a source electrode and/or a drain electrode via MLI 3030), and/or a body voltage $V_B$ is applied to body region 3020 (for example, to a body electrode via MLI 3030). In some implementations, for a given fluidic gate voltage $V_{FG}$ (and a given source voltage $V_S$/given drain voltage $V_D$), dual-gate ISFET 4000 generates a drain-to-source current $I_{ds}$ that is a function of a quantity of analytes 3078 present in the biological sample. In some implementations, drain-to-source current $I_{ds}$ is evaluated at a threshold voltage $V_{TH}$ of dual-gate ISFET 4000 to determine presence (or absence) of analytes 3078 (for example, when fluidic gate voltage $V_{FG}$ is approximately equal to threshold voltage $V_{TH}$), as described above with reference to dual-gate ISFET 3000.

When the biological sample includes glucose, hydrogen ions (H+) react with sensing layer 3065, drain-to-source current increases. I-V curve 4020 and I-V curve 4025 model a drain-to-source current $I_{DS}$ (which correlates with a concentration of hydrogen ions (H+), respectively, in electrolyte solution 3070) as a function of a fluidic gate voltage $V_{FG}$. I-V curve 4020 is generated when electrolyte solution 3070 is constituent free, and I-V curve 4025 is generated when electrolyte solution 3070 includes constituents that can react with the products of the enzymatic reactions (and thus release additional ions). From I-V curve 4020 and I-V curve 4025, it is observed that drain-to-source current $I_{DS}$ detected by dual-gate ISFET 4000 significantly increases when electrolyte solution 3070 includes the constituents (such as iron-containing constituents), providing enhanced detection sensitivity. Such signal enhancement can be achieved with minimal (to no) increase in noise, providing dual-gate ISFET 4000 with better signal-to-noise ratio (SNR) than dual-gate ISFETs that implement only enzyme-modified detection mechanism 3080. Further, by having two signal sources for enhancing signal detection, dual-gate ISFET 4000 reduces reaction times and/or incubation times required for detecting analytes 3078, which can lead to testing cost savings and testing time savings compared to other dual-gate ISFETs. Different embodiments may have different advantages, and no particular advantage is necessarily required of any embodiment.

Referring now to FIG. 38A and FIG. 38B, FIG. 39A and FIG. 39B, and FIG. 40A and FIG. 40B, glucose monitoring and detection by a dual-gate ISFET 1 was compared with glucose monitoring and detection by a dual-gate ISFET 2. Dual-gate ISFET 1, such as dual-gate ISFET 3000, utilizes only enzyme-modified detection mechanisms as described herein to produce ions for enhancing signal strength (for example, observable drain-to-source current). Dual-gate ISFET 2, such as dual-gate ISFET 4000, utilizes enzyme-modified detection mechanisms in combination with an electrolyte solution that includes constituents that can react with products from enzymatic reactions associated with enzyme-modified detection mechanisms as described herein to produce ions for enhancing signal strength (for example, observable drain-to-source current). For purposes of the following discussion, dual-gate ISFET 1 and dual-gate ISFET 2 both utilized enzyme-detection mechanisms that include glucose oxidase enzyme (GOx), and dual-gate ISFET 2 utilized iron-containing constituents (such as ferrous sulfate) in the electrolyte solution. Various metrics, as detailed below, indicated that dual-gate ISFET 2 provides superior glucose monitoring and detection capabilities for sample solutions with both low glucose concentrations and high glucose concentrations.

Figure 38A:
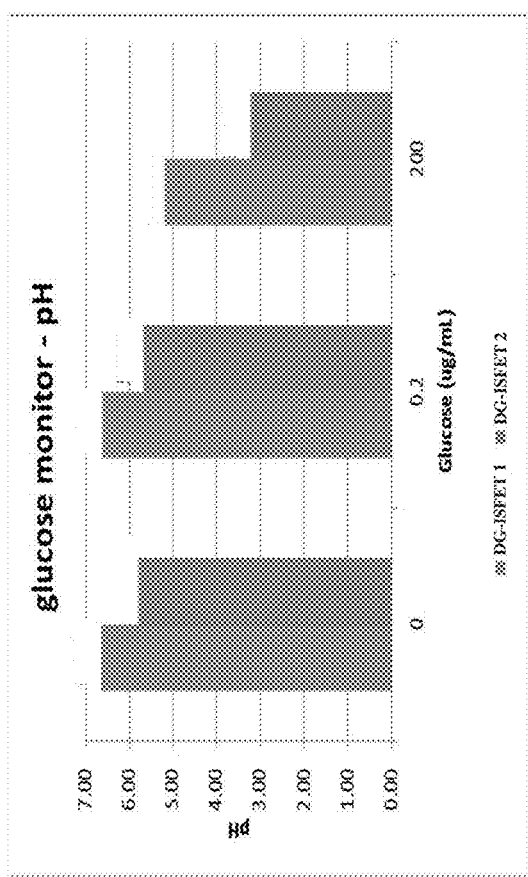
Figure 38B:
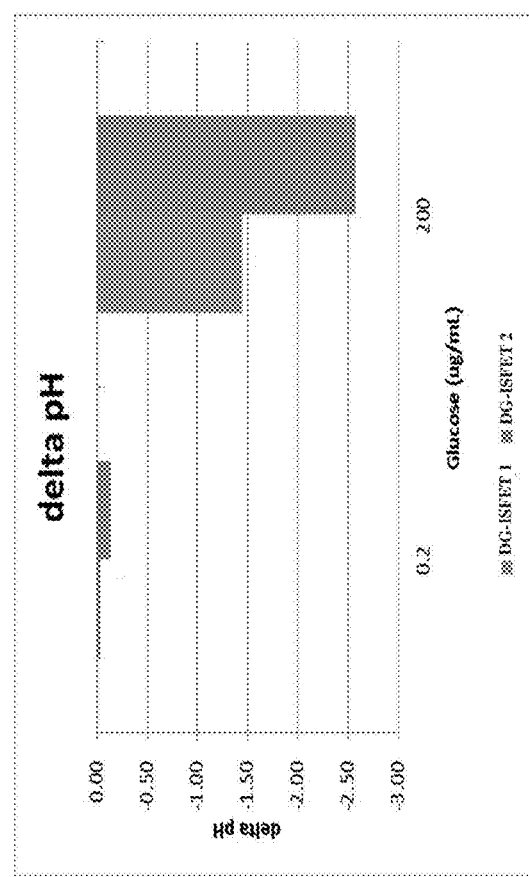

Dual-gate ISFETs can detect a drop in pH levels when glucose is present in a sample solution. FIG. 38A depicts pH levels detected by dual gate ISFET 1 and dual-gate ISFET 2 for a sample solution having various glucose concentrations, such as no glucose (0 ug/ml), about 0.2 ug/ml of glucose, and about 200 ug/ml of glucose; and FIG. 38B depicts a change in pH (delta pH) detected by dual gate ISFET 1 and dual-gate ISFET 2 as the glucose concentration increases. Though both dual-gate ISFET 1 and dual-gate ISFET 2 detect drops in pH levels as the glucose concentration increases, dual-gate ISFET 2 is more sensitive to glucose concentration increases, particularly with low glucose concentrations. For example, when the glucose concentration increases from 0 ug/ml to about 0.2 ug/ml, dual-gate ISFET 1 barely registers a pH change (for example, about 0.03 ug/ml), while dual-gate ISFET 2 registers a detectable pH change (for example, about 0.1 ug/ml). In another example, when the glucose concentration increases from 0 ug/ml to about 200 ug/ml, dual-gate ISFET 1 registers a significantly smaller pH change (for example, about 1.5 ug/ml) than dual-gate ISFET 2 (for example, about 2.6 ug/ml). The enhanced signal mechanisms of dual-gate ISFET 2 thus significantly increase detectability of glucose in sample solutions. Compared to the signal enhancement mechanisms of dual-gate ISFET 1, the signal enhancement mechanisms of dual-gate ISFET 2 register significant decreases in pH levels (in some implementations, as much as 250% greater for low glucose concentrations and as much as 75% greater for high glucose concentrations).

Dual-gate ISFETs can also detect an increase in drain-to-source current when glucose is present in a sample solution as a fluidic gate voltage $V_{FG}$ is applied to respective a fluidic gate structure of dual-gate ISFET 1 and dual-gate ISFET 2, respectively. In some implementations, the drain-to-source current is evaluated when the fluidic gate voltage $V_{FG}$ is approximately equal to a threshold voltage $V_{TH}$ respectively of dual-gate ISFET 1 and dual gate ISFET 2. FIG. 39A depicts drain-to-source current $I_{DS}$ (in microamps (uA)) detected by dual gate ISFET 1 and dual-gate ISFET 2 for the sample solution having the various glucose concentrations; and FIG. 39B depicts a change in the drain-to-source current $I_{DS}$ (delta $I_{DS}$) detected by dual gate ISFET 1 and dual-gate ISFET 2 as the glucose concentration increases. Though both dual-gate ISFET 1 and dual-gate ISFET 2 detect increases in drain-to-source current $I_{DS}$ as the glucose concentration increases in the sample solution, dual-gate ISFET 2 is more sensitive to the glucose concentration increases. For example, when the glucose concentration increases from 0 ug/ml to about 0.2 ug/ml, dual-gate ISFET 1 barely registers a drain-to-source current $I_{DS}$ change (for example, about 0.1 uA), while dual-gate ISFET 2 registers a detectable drain-to-source current $I_{DS}$ change (for example, about 1.4 uA). In another example, when the glucose concentration increases from 0 ug/ml to about 200 ug/ml, dual-gate ISFET 1 registers a significantly smaller drain-to-source current $I_{DS}$ change (for example, about 5.6 uA) than dual-gate ISFET 2 (for example, about 9.0 uA). Compared to the signal enhancements mechanisms of dual-gate ISFET 1, the signal enhancement mechanisms of dual-gate ISFET 2 register significant increases in drain-to-source current $I_{DS}$ as fluidic gate voltage $V_{FG}$ is applied to the fluidic gate structure (in some implementations, as much as 1300% greater for low glucose concentrations and as much as 60% greater for high glucose concentrations).

Figure 40A:
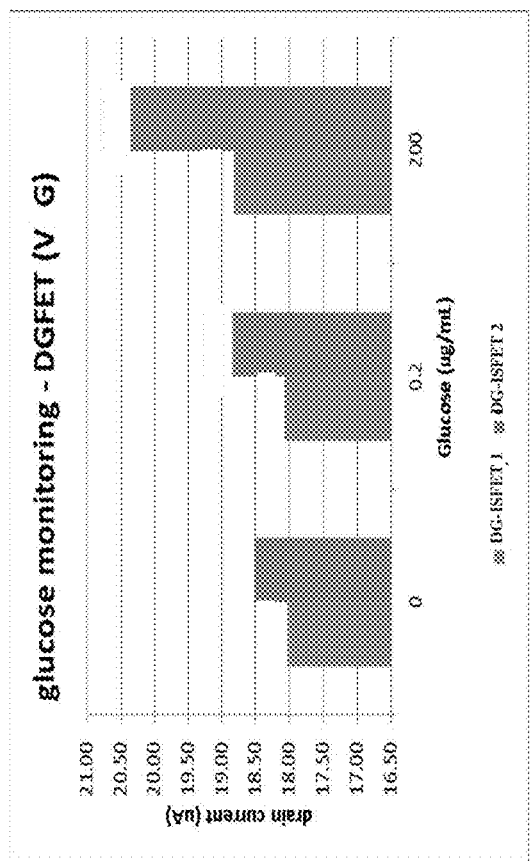
Figure 40B:
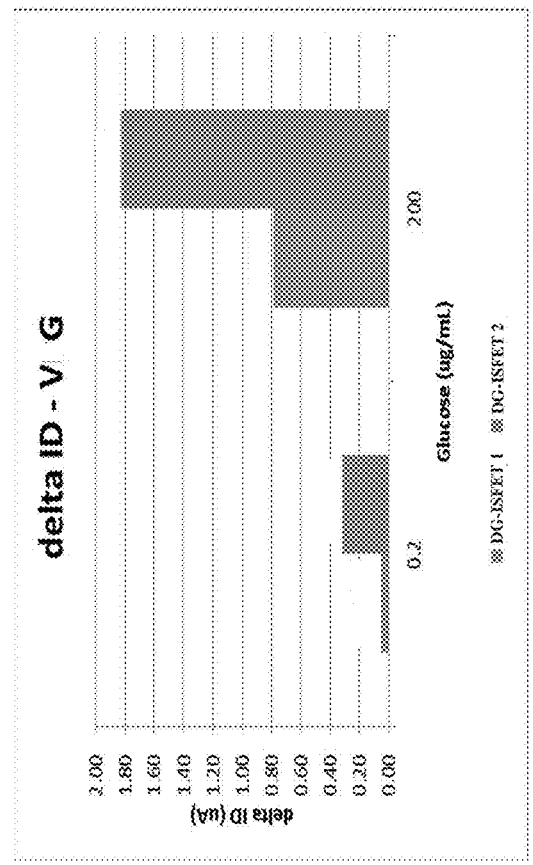

Dual-gate ISFETs can also detect an increase in drain-to-source current when glucose is present in a sample solution as a gate voltage $V_G$ is applied to a gate structure of dual-gate ISFET 1 and dual-gate ISFET 2, respectively. In some implementations, the drain-to-source current is evaluated when the gate voltage $V_G$ is approximately equal to a threshold voltage $V_{TH}$ respectively of dual-gate ISFET 1 and dual gate ISFET 2. FIG. 40A depicts drain-to-source current $I_{DS}$ (in uA) detected by dual gate ISFET 1 and dual-gate ISFET 2 for the sample solution having the various glucose concentrations; and FIG. 40B depicts a change in the drain-to-source current $I_{DS}$ (delta $I_{DS}$) detected by dual gate ISFET 1 and dual-gate ISFET 2 as the glucose concentration increases. Though both dual-gate ISFET 1 and dual-gate ISFET 2 detect increases in drain-to-source current $I_{DS}$ as the glucose concentration increases in the sample solution, dual-gate ISFET 2 is more sensitive to the glucose concentration increases. For example, when the glucose concentration increases from 0 ug/ml to about 0.2 ug/ml, dual-gate ISFET 1 barely registers a drain-to-source current $I_{DS}$ change (for example, about 0.05 uA), while dual-gate ISFET 2 registers a detectable drain-to-source current $I_{DS}$ change (for example, about 0.3 uA). In another example, when the glucose concentration increases from 0 ug/ml to about 200 ug/ml, dual-gate ISFET 1 registers a significantly smaller drain-to-source current $I_{DS}$ change (for example, about 0.8 uA) than dual-gate ISFET 2 (for example, about 1.8 uA). Compared to the signal enhancements mechanisms of dual-gate ISFET 1, the signal enhancement mechanisms of dual-gate ISFET 2 register significant increases in drain-to-source current $I_{DS}$ as gate voltage $V_G$ is applied to the gate structure (in some implementations, as much as 500% greater for low glucose concentrations and as much as 125% greater for high glucose concentrations).

Figure 41:
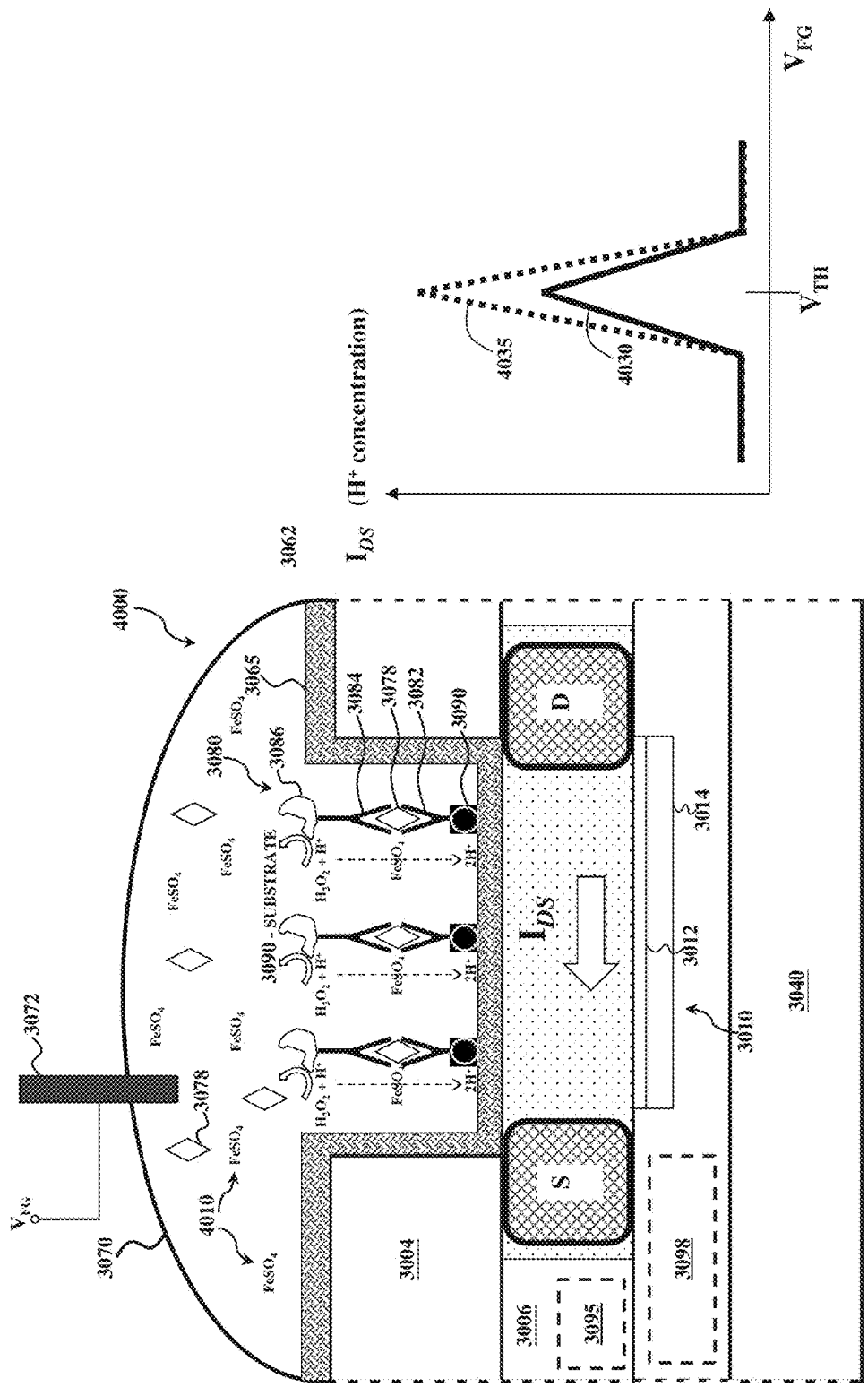
FIG. 41 is a fragmentary diagrammatic cross-sectional view of a dual-gate ISFET for a ELISA platform according to various aspects of the present disclosure.
Figure 42A:
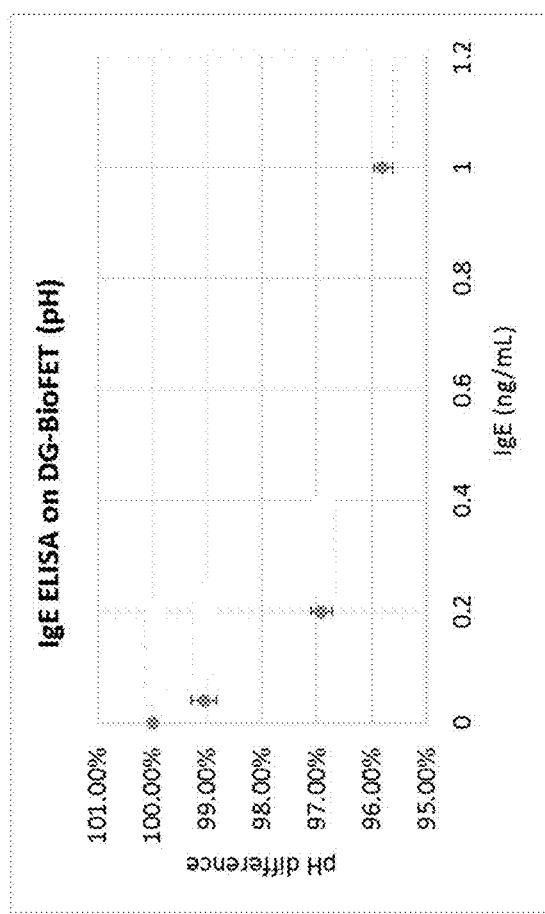
FIG. 42A and FIG. 42B illustrate various detection capabilities of a dual-gate ISFET, such as the dual-gate ISFET depicted in FIG. 41, according to various aspects of the present disclosure.
Figure 42B:
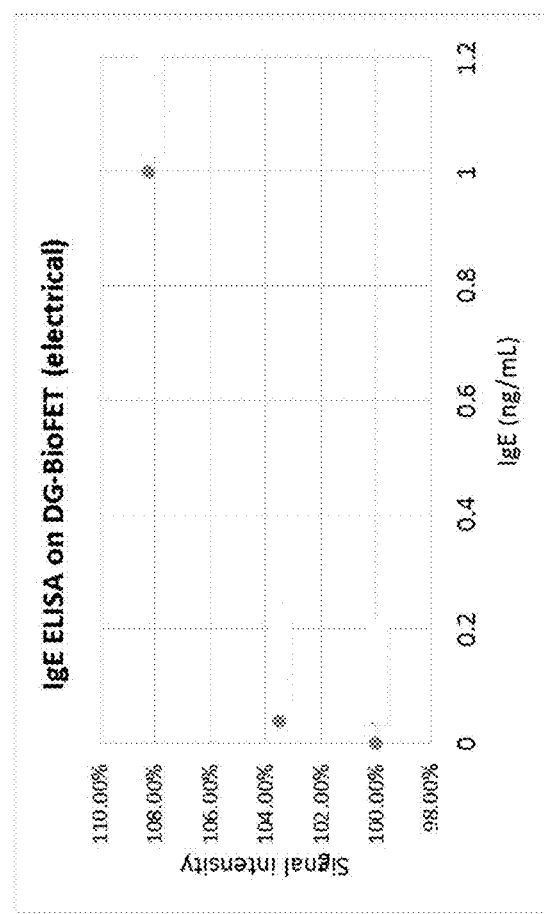

Referring now to FIG. 41, similar to dual-gate ISFET 3000, dual-gate ISFET 4000 can be implemented for enzyme-linked immunosorbent assay (ELISA), which generally refers to an immunological assay for measuring bio-entities in a biological sample. ELISA can include various steps for detection and quantification of the bio-entities, as described above with reference to dual-gate ISFET 3000. When dual-gate ISFET 4000 is configured in an ELISA platform, enzyme-modified detection mechanism 3080 includes capture antibody 3082 and detection antibody 3084, where capture antibody 3082 is immobilized on sensing layer 3065 (for example, via linker 3090). Capture antibodies 3082 may be provided in solution form in fluidic channel 3075, such that the solution fills opening 3060 and capture antibodies 3082 bind with sensing layer 3065 and/or linker 3090. Any excess capture antibodies 3082 that do not bind with sensing layer 3065 and/or linker 3090 can be removed by an appropriate washing process. Then, a biological sample is provided in solution form in fluidic channel 3075. The biological sample fills opening 3060 (thus contacting a surface of sensing layer 3065) and any analytes 3078 from biological sample bind to capture antibodies 3082. Any excess analytes 3078 that do not bind with capture antibodies 3082 can be removed by an appropriate washing process.

Subsequently, enzyme-labeled detection antibodies (for example, detection antibodies 3084 conjugated with enzymes 3086) are added to sensing well 3055. For example, a solution that includes enzyme-labeled detection antibodies is provided in fluidic channel 3075, such that the solution fills opening 3060 and detection antibodies 3084 bind to any analytes 3078 bound to capture antibodies 3082. Any enzyme-labeled detection antibodies that do not bind with analytes 3078 can be removed by an appropriate washing process. Enzyme substrate 3090 is then added to sensing well 3055. For example, enzyme substrate 3090 is introduced into enzyme solution 3070, causing enzymatic reactions. In some implementations, enzyme substrate 3090 binds with active sites of enzymes 3086, generating ions, such as hydrogen ions (H+), that can react with sensing layer 3065, and thus be detected by dual-gate ISFET 4000. To further enhance dual-gate ISFET 4000, electrolyte solution 3070 includes constituents 4010, such as iron-containing constituents (for example, ferrous sulfate), that can react with products from the enzymatic reaction to generate additional ions that can react with sensing layer 3065, and thus be detected by dual-gate ISFET 4000. In some implementations, the enzymatic reaction produces hydrogen peroxide ($H_2O_2$), which reacts with constituents 4010 (such as ferrous sulfate) to produce ions. As described herein, the protons (here, 2H+) generated from the enzymatic reaction increase drain-to-source current $I_{DS}$, improving detectability of analytes 3078. During ELISA, various incubation periods may be implemented for each solution added to fluidic channel 3065 to ensure sufficient time for binding. In the various implementations, temperature sensor 3095 and/or a heater 3098 are used to control a temperature of device substrate 3002, improving efficiency of enzymatic reactions associated with enzyme-modified detection mechanisms 3080 and/or reactions between products of the enzymatic reactions and constituents of electrolyte solution 3070 (for example, by shortening enzymatic reaction time and/or other reaction time required for generating the ions and/or detectable levels of drain-to-source current).

For ELISA platforms, dual-gate ISFET 4000 also includes at least two sources for enhancing its electrical signal: a first ion generated from an enzymatic reaction that corresponds with enzyme-modified detection mechanism 3080 detecting analyte 3078, and a second ion generated when a constituent of electrolyte solution 3070 reacts with a product of the enzymatic reaction. Such is depicted in FIG. 41 as two protons (for example, 2H+), which react with sensing layer 3065 and increase drain-to-source current. I-V curve 4030 and I-V curve 4035 model a drain-to-source current $I_{DS}$ (which correlates with a concentration of hydrogen ions (H+), respectively, in electrolyte solution 3070) as a function of a fluidic gate voltage $V_{FG}$. I-V curve 4030 is generated when electrolyte solution 3070 is constituent free, and I-V curve 4035 is generated when electrolyte solution 3070 includes constituents that can react with the products of the enzymatic reactions (and thus release additional ions). From I-V curve 4030 and I-V curve 4035, it is observed that drain-to-source current $I_{DS}$ detected by dual-gate ISFET 4000 significantly increases when electrolyte solution 3070 includes the constituents (such as iron-containing constituents), providing enhanced detection capabilities for dual-gate ISFET 4000 in ELISA platforms as well as glucose monitoring platforms.

Dual-gate ISFET 4000 can significantly improve ELISA detection limits. For example, traditional sandwich ELISA methods have a minimum detection limit of about 1.56 nanograms/milliliter (ng/ml), whereas implementing dual-gate ISFET 4000 in ELISA platforms has a minimum detection limit of about 0.04 ng/ml. Referring now to FIG. 41A and FIG. 41B, FIG. 41A depicts a pH change (%) detected by a dual gate ISFET, such as dual-gate ISFET 4000, as an immunoglobulin E (IgE) concentration increases in a sample solution; and FIG. 41B depicts a change in drain-to-source current (%) detected by the dual-gate ISFET, such as dual-gate ISFET 4000 as the IgE concentration increases in the sample solution. The pH change and the drain-to-source current change was evaluated at various immunoglobulin E (IgE) concentrations, such as no IgE (0 ng/ml), about 0.04 ng/ml of IgE, about 0.2 ng/ml of IgE, and about 1 ng/ml of IgE. In FIG. 41 and FIG. 41B, the dual-gate ISFET registers a pH change (for example, about a 1% decrease) and a drain-to-source current change (for example, about a 4% increase) when the sample solution has about 0.04 ng/ml of IgE. As the of IgE concentration increases, dual-gate ISFET registers larger pH changes and drain-to-source current changes. For example, the dual-gate ISFET registers a pH change of about a 5% decrease and a drain-to-source current change of about a 8% increase when the sample solution has about 1 ng/ml of IgE. Dual-gate ISFET 4000 in ELISA platforms thus effectively detects minimal IgE concentrations.

Referring now to FIG. 43, a flow chart of a method 4050 for analyzing a biological sample using a dual-gate ISFET, such as dual-gate ISFET 4000, is provided. At block 4055, the biological sample is provided to the dual-gate ISFET. The dual-gate ISFET includes a fluidic gate structure and a gate structure disposed over opposite surfaces of a device substrate. At block 4060, an enzymatic reaction is generated when an enzyme-modified detection mechanism detects a target analyte, such that a first ion and a product are released into an electrolyte solution of the fluidic gate structure. At block 4065, a reaction is generated between the product of the enzymatic reaction and a constituent of the electrolyte solution, such that a second ion is released into the electrolyte solution of the fluidic gate structure. At block 4070, an electrical signal as a sensing layer of the fluidic gate structure reacts with the first ion and the second ion, wherein the electrical signal indicates an ion concentration in the electrolyte solution that correlates with a presence or a quantity of target analytes in the biological sample. Additional steps can be provided before, during, and after method 4050, and some of the steps described can be moved, replaced, or eliminated for additional embodiments of method 4050.

The present disclosure contemplates utilization of dual-gate ISFET 4000 for various disease diagnostic platforms, including any of the disease diagnostic platforms described herein, such as early diagnosis of protein-based diseases (including cardiac, renal, hepatic, and cancer markers), urinary $H_2O_2$ detection for prediction of pathogenesis and/or progression of diseases, and/or other disease diagnostic. The present disclosure further contemplates implementing dual-gate ISFET in a sensor array, such as described with reference to FIG. 36.

It should be understood that any of the advantages above may be present in some embodiments of the disclosure, but are not required of any specific embodiment. Further, it is understood that different embodiments disclosed herein offer different disclosure, and that they may make various changes, substitutions and alterations herein without departing from the spirit and scope of the present disclosure.

Dual-gate ion-sensitive field effect transistors (ISFETs) for disease diagnostics, along with various methods for implementing the dual-gate ISFETs, are disclosed herein according to various embodiments. An exemplary dual-gate ISFET for analyzing a biological sample includes a device substrate having a first surface and a second surface, the first surface opposite the second surface. A gate structure is disposed over the first surface between a source region and a drain region in the device substrate, wherein a channel region is defined in the device substrate between the source region and the drain region. A fluidic gate structure disposed over the second surface, wherein the fluidic gate structure includes a sensing well disposed over the channel region. The sensing well includes a sensing layer and an electrolyte solution. The dual-gate ISFET is configured to generate an electrical signal when the sensing layer reacts with an ion generated from an enzymatic reaction that occurs when an enzyme-modified detection mechanism detects a target analyte and an ion generated from a reaction between a product of the enzymatic reaction and a constituent of the electrolyte solution, the electrical signal indicating an ion concentration in the electrolyte solution that correlates with a presence or a quantity of target analytes in the biological sample.

Another exemplary dual-gate ISFET includes a gate structure and a fluidic gate structure disposed over opposite surfaces of a device substrate. The gate structure is disposed over a channel region defined between a source region and a drain region in the device substrate. The fluidic gate structure includes a sensing well that is disposed over the channel region. The sensing well includes a sensing layer and an electrolyte solution. The electrolyte solution includes a constituent that can react with a product of an enzymatic reaction that occurs when an enzyme-modified detection mechanism detects an analyte. The sensing layer can react with a first ion generated from the enzymatic reaction and a second ion generated from a reaction between the product of the enzymatic reaction and the constituent, such that the dual-gate ISFET generates an enhanced electrical signal.

Another exemplary dual-gate ISFET includes a device substrate having a first surface and a second surface. The first surface is opposite the second surface. A gate structure is disposed over the first surface, and a fluidic gate structure is disposed over the second surface. The gate structure includes a gate dielectric layer and a gate electrode layer disposed between a source region and a drain region in the device substrate. A channel region is defined in the device substrate between the source region and the drain region. The fluidic gate structure includes a sensing well disposed over the channel region. The sensing well includes a sensing layer and an electrolyte solution. The dual-gate ISFET generates an electrical signal when the sensing layer reacts with ions generated from enzyme-modified detection mechanisms, the electrical signal indicating an ion concentration in the electrolyte solution that correlates with a presence and/or a quantity of target analytes in the biological sample.

In some implementations, each enzyme-modified detection mechanism includes a capture antibody for capturing a target analyte, wherein the capture antibody is immobilized on the sensing layer. Each enzyme-modified detection mechanism further includes a detection antibody conjugated with an enzyme, wherein the detection antibody binds with the target analyte and the enzyme generates the ions. The dual-gate ISFET may further include a linker that immobilizes the capture antibody on the sensing layer. In some implementations, each enzyme-modified detection mechanism includes only an enzyme immobilized on the sensing layer, for example, by a linker.

In some implementations, the sensing layer includes a high-k dielectric material, and the gate electrode layer includes polysilicon. In some implementations, the gate structure is substantially aligned with the sensing well of the fluidic gate structure. In some implementations, the device substrate is a silicon-on-insulator (SOI) substrate that includes an insulator layer and a silicon layer. In such implementations, the source/drain regions and the channel region can be defined in the silicon layer, the gate structure can be disposed over a front side surface of the silicon layer, and the fluidic gate structure can extend through the insulator layer, such that the fluidic gate structure is disposed over a backside surface of the silicon layer. In some implementations, the electrolyte solution includes calcium chloride ($CaCl_2$), sodium chloride (NaCl), potassium chloride (KCl), magnesium chloride ($MgCl_2$), or a combination thereof. In some implementations, the dual-gate ISFET further includes a temperature sensor configured to measure a temperature of the device substrate, and/or a heater configured to heat the device substrate.

An exemplary method for analyzing a biological sample using a dual-gate ion-sensitive field effect transistor (ISFET), such as described herein, includes generating enzymatic reactions from enzyme-modified detection mechanisms, such that the enzyme-modified detection mechanisms release ions into an electrolyte solution of the fluidic gate structure. The method further includes generating an electrical signal as a sensing layer of the fluidic gate structure reacts with the ions, wherein the electrical signal indicates an ion concentration in the electrolyte solution that correlates with a presence or a quantity of target analytes in the biological sample. In some implementations, the electrical signal corresponds to a drain-to-source current of the dual-gate ISFET. In some implementations, the method includes biasing the fluidic gate structure with a fluidic gate voltage, wherein the electrical signal is evaluated when the fluidic gate voltage reaches a threshold voltage. The method can further include controlling a temperature of the device substrate to optimize generation of enzymatic reactions from the enzyme-modified detection mechanisms.

In some implementations, the method includes immobilizing capture antibodies of the enzyme-modified detection mechanisms on the sensing layer. In some implementations, the method further includes exposing the sensing layer to the biological sample in solution form, wherein the capture antibodies bind any target analytes in the biological sample. In some implementations, the method further includes exposing the sensing layer to a solution that includes enzyme-labeled detection antibodies of the enzyme-modified detection mechanisms, wherein the enzyme-labeled detection antibodies bind with the target analytes bound to the capture antibodies, and further wherein the enzyme-labeled detection antibodies generate the ions. In some implementations, generating the enzymatic reactions includes exposing the enzyme-labeled detection antibodies to an enzyme substrate.

Another exemplary method for analyzing a biological sample using a dual-gate ISFET includes providing the biological sample to the dual-gate ISFET, wherein the dual-gate ISFET includes a fluidic gate structure and a gate structure, wherein the fluidic gate structure and the gate structure are disposed over opposite surfaces of a device substrate; generating enzymatic reactions from enzyme-modified detection mechanisms, such that the enzyme-modified detection mechanisms release ions into an electrolyte solution of the fluidic gate structure; and biasing the fluidic gate structure and the gate structure to generate an electrical signal as a sensing layer of the fluidic gate structure reacts with the ions, wherein the electrical signal indicates an ion concentration in the electrolyte solution that correlates with a presence or a quantity of target analytes in the biological sample. In some implementations, the method further comprises evaluating the threshold voltage to determine the ion concentration. In some implementations, the electrical signal is a drain-to-source current of the dual-gate ISFET. In some implementations, the fluidic gate structure is biased with a fluidic gate voltage, wherein the electrical signal is evaluated when the fluidic gate voltage reaches a threshold voltage. In some implementations, the gate structure is biased with a gate voltage, such that the dual-gate ISFET uses both the fluidic gate structure and the gate structure for sensing operations. In some implementations, the gate structure is grounded, such that the dual-gate ISFET uses only the fluidic gate structure for sensing operations.

Another exemplary method for analyzing a biological sample using a dual-gate ISFET includes providing the biological sample to the dual-gate ISFET, wherein the dual-gate ISFET includes a fluidic gate structure and a gate structure, wherein the fluidic gate structure and the gate structure are disposed over opposite surfaces of a device substrate, and further wherein the fluidic gate structure includes an electrolyte solution disposed over a sensing layer; biasing the fluidic gate structure and the gate structure to generate an electrical signal as the sensing layer of the fluidic gate structure reacts with ions released into the electrolyte solution by enzyme-modified detection mechanisms; and evaluating a threshold voltage of the fluidic gate structure when the electrical signal is generated, wherein the threshold voltage indicates an ion concentration in the electrolyte solution that correlates with a presence or a quantity of target analytes in the biological sample. In some implementations, the gate structure is biased with a gate voltage, such that the dual-gate ISFET uses both the fluidic gate structure and the gate structure for sensing operations. In some implementations, the gate structure is grounded, such that the dual-gate ISFET uses only the fluidic gate structure for sensing operations. In some implementations, the electrical signal is a drain-to-source current of the fluidic gate structure. In some implementations, the threshold voltage increases as the ion concentration increases.

An exemplary sensor array for analyzing a biological sample can include a plurality of sensors, wherein each sensor includes a dual-gate ion-sensitive field effect transistor (ISFET), such as described herein. The sensor array is configured to individually bias the fluidic gate structures and the gate structures of the dual-gate ISFETs of the plurality of sensors to generate an electrical signal when the sensing layers react with ions generated from enzyme-modified detection mechanisms. The electrical signal indicates an ion concentration in the electrolyte solutions that correlates with a presence or a quantity of target analytes in the biological sample. In some implementations, an individual bias is applied to each gate structure to compensate for variations in dual-gate ISFETs, and a fluidic gate voltage is applied to the fluid gate structures, wherein the electrical signal is a drain-to-source current. In some implementations, the gate structures are grounded. Each sensor can further include a temperature sensor configured to measure a temperature of the device substrate and a heater configured to heat the device substrate. In some implementations, the sensor array further includes a row decoder and a column decoder configured to selectively turn on or off each of the plurality of sensors.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. For example, various embodiments of the present disclosure may include combinations of the specific embodiments and examples provided in detail herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A dual-gate ion-sensitive field effect transistor (ISFET) comprising:
   a device substrate having a first surface and a second surface, the first surface opposite the second surface;
   a gate structure disposed over the first surface between a source region and a drain region in the device substrate, wherein a channel region is defined in the device substrate between the source region and the drain region;
   a fluidic gate structure disposed over the second surface, wherein the fluidic gate structure includes a sensing well disposed over the channel region, the sensing well including a sensing layer; and
   wherein the dual-gate ISFET is configured to generate an electrical signal when the sensing layer reacts with a first ion generated from an enzymatic reaction that occurs when an enzyme-modified detection mechanism detects a target analyte and a second ion generated from a reaction between a product of the enzymatic reaction and a constituent of an electrolyte solution.

2. The dual-gate ISFET of claim 1, wherein the product is hydrogen peroxide.

3. The dual-gate ISFET of claim 1, wherein the constituent is ferrous sulfate.

4. The dual-gate ISFET of claim 1, wherein the enzyme-modified detection mechanism includes glucose oxidase enzyme ($GO_x$).

5. The dual-gate ISFET of claim 1, wherein the enzyme-modified detection mechanism includes an enzyme immobilized on the sensing layer, wherein the enzyme generates the first ion and the product when the enzyme detects the target analyte.

6. The dual-gate ISFET of claim 1, wherein the enzyme-modified detection mechanism includes:
 a capture antibody for capturing the target analyte, wherein the capture antibody is immobilized on the sensing layer; and
 a detection antibody conjugated with an enzyme, wherein the enzyme generates the first ion and the product upon the detection antibody binding with the target analyte.

7. The dual-gate ISFET of claim 1, wherein the sensing layer includes a high-k dielectric material.

8. The dual-gate ISFET of claim 1, further comprising:
 a temperature sensor configured to measure a temperature of the device substrate; and
 a heater configured to heat the device substrate.

9. The dual-gate ISFET of claim 1, further comprising a reference electrode for biasing the fluid gate structure.

10. A dual-gate ion-sensitive field effect transistor (ISFET) comprising:
 a device substrate having a first surface and a second surface, the first surface opposite the second surface;
 a gate structure disposed over the first surface, the gate structure including:
  a gate dielectric layer, and
  a gate electrode layer disposed between a source region and a drain region in the device substrate, wherein a channel region is defined in the device substrate between the source region and the drain region; and
 a fluidic gate structure disposed over the second surface, wherein the fluidic gate structure includes a sensing well disposed over the channel region, the sensing well including:
  a sensing layer configured to react with a first ion generated from an enzymatic reaction that occurs when an enzyme-modified detection mechanism detects a target analyte and a second ion generated from a reaction between a product of the enzymatic reaction and an iron-containing constituent, such that the dual-gate ISFET generates an electrical signal.

11. The dual-gate ISFET of claim 10, wherein:
 the target analyte is glucose;
 the enzyme-modified detection mechanism includes glucose oxidase enzyme ($GO_x$); and
 the iron-containing constituent is ferrous sulfate ($FeSO_4$).

12. The dual-gate ISFET of claim 10, wherein the enzyme-modified detection mechanism includes an enzyme immobilized on the sensing layer, wherein the enzyme generates the first ion and the product when the enzyme reacts with the target analyte.

13. The dual-gate ISFET of claim 12, wherein the product is hydrogen peroxide.

14. The dual-gate ISFET of claim 10, wherein the sensing layer includes a high-k dielectric material, and the gate electrode layer includes polysilicon.

15. A method for analyzing using a dual-gate ion-sensitive field effect transistor (ISFET) wherein the dual-gate ISFET includes a fluidic gate structure and a gate structure, wherein the fluidic gate structure and the gate structure are disposed over the opposite surfaces of a device substrate, the method comprising:
 generating electrical characteristic data based on an an electrical signal generated from a sensing layer of the fluidic gate structure reacting with:
  a first ion generated from an enzymatic reaction when an enzyme-modified detection mechanism detects a target analyte, and
  second ion generated when a product of the enzymatic reaction reacts with a constituent of an electrolyte solution; and determining a presence or a quantity of target analytes based on the electrical characteristic data.

16. The method of claim 15, wherein:
 the target analyte is glucose; and
 the enzyme-modified detection mechanism includes glucose oxidase enzyme, such that the first ion is generated by an enzymatic reaction between glucose and glucose oxidase enzyme.

17. The method of claim 16, wherein:
 the constituent is ferrous sulfate; and
 the enzymatic reaction between glucose and glucose oxidase enzyme produces hydrogen peroxide, such that the second ion is generated by a reaction between the hydrogen peroxide and the ferrous sulfate.

18. The method of claim 16, wherein the constituent is an iron-containing constituent, and the product is hydrogen peroxide.

19. The method of claim 15, wherein the generating the electrical characteristic data includes generating a current-voltage (I-V) curve by biasing the fluidic gate structure with a fluidic gate voltage.

20. The method of claim 19, wherein the determining the presence or the quantity of target analytes based on the electrical characteristic data includes evaluating a drain-to-source current when the fluidic gate voltage reaches a threshold voltage.

* * * * *